(12) United States Patent
Gouble

(10) Patent No.: US 8,426,177 B2
(45) Date of Patent: Apr. 23, 2013

(54) MEGANUCLEASE VARIANTS CLEAVING A DNA TARGET SEQUENCE FROM THE MOUSE ROSA26 LOCUS AND USES THEREOF

(75) Inventor: Agnes Gouble, Paris (FR)

(73) Assignee: Cellectis, Romainville (FR)

( * ) Notice: Subject to any disclaimer, the term of this patent is extended or adjusted under 35 U.S.C. 154(b) by 322 days.

(21) Appl. No.: 12/663,164

(22) PCT Filed: Jun. 6, 2008

(86) PCT No.: PCT/IB2008/002500
§ 371 (c)(1),
(2), (4) Date: Apr. 16, 2010

(87) PCT Pub. No.: WO2008/152523
PCT Pub. Date: Dec. 18, 2008

(65) Prior Publication Data
US 2010/0325745 A1    Dec. 23, 2010

(30) Foreign Application Priority Data

Jun. 6, 2007   (WO) .................. PCT/IB07/02830

(51) Int. Cl.
*C12N 9/00*   (2006.01)
(52) U.S. Cl.
USPC ........................................ 435/183; 536/23.2
(58) Field of Classification Search .................. 435/183; 536/23.2
See application file for complete search history.

(56) References Cited

FOREIGN PATENT DOCUMENTS

| WO | 2007 014275 | 2/2007 |
|---|---|---|
| WO | 2007 049156 | 5/2007 |

OTHER PUBLICATIONS

U.S. Appl. No. 12/671,853, filed Feb. 2, 2010, Gouble, et al.
Smith, Julianne et al., "A combinatorial approach to create artificial homing endonucleases cleaving chosen sequences", Nucleic Acids Research, vol. 34, No. 22, pp. 1-12, (Nov. 27, 2006).
Kisseberth, William C. et al., "Ubiquitous Expression of Marker Transgenes in Mice and Rats", Developmental Biology, vol. 214, No. 1, pp. 128-138, (Oct. 1, 1999).
Arnould, Sylvain et al., "Engineering of Large Numbers of Highly Specific Homing Endonucleases that Induce Recombination on Novel DNA Targets", J. Mol. Biol., Elsevier, vol. 355, No. 3, pp. 443-458, (Jan. 20, 2006).
Stoddard, Barry L. "Homing endonuclease structure and function", Quaterly Reviews of Biophysics, vol. 38, No. 1, pp. 49-95, (Feb. 2006).

*Primary Examiner* — Tekchand Saidha
(74) *Attorney, Agent, or Firm* — Oblon, Spivak, McClelland, Maier & Neustadt, L.L.P.

(57) ABSTRACT

An I-CreI variant, wherein one of the two I-CreI monomers has at least two substitutions, one in each of the two functional subdomains of the LAGLIDADG (SEQ ID NO: 150) core domain situated respectively from positions 26 to 40 and 44 to 77 of I-CreI, said variant being able to cleave a DNA target sequence from the mouse ROSA26 locus. Use of said variant and derived products for the engineering of transgenic mice and recombinant mouse cell lines expressing an heterologous protein of interest.

1 Claim, 21 Drawing Sheets

```
                        -12  -11 -10 -9 -8 -7 -6 -5 -4 -3 -2 -1  1  2  3  4  5  6  7  8  9 10 11  12
C1221               (T) C  A  A  A  A  C  G  T  C  G  T  A  C  G  A  C  G  T  T  T  T  G (A)
(SEQ ID NO: 2)
10GGG   P           (T) C  GGG  A  C  G  T  C  G  T  A  C  G  A  C  G  T  CCC  G (A)
(SEQ ID NO: 31)
5GAT    P           (T) C  A  A  A  A  C  GAT  G  T  A  C  ATC  G  T  T  T  T  G (A)
(SEQ ID NO: 32)
5TAT    P           (T) C  A  A  A  A  C  TAT  G  T  A  C  ATA  G  T  T  T  T  G (A)
(SEQ ID NO: 33)
rosa1                   C  A  A  C  A  T  GAT  G  T  T  C  ATA  A  T  CCC  A
(SEQ ID NO: 15)
rosa1.2                 C  A  A  C  A  T  GAT  G  T  A  C  ATA  A  T  CCC  A
(SEQ ID NO: 34)
rosa1.3                 C  A  A  C  A  T  GAT  G  T  A  C  ATC  A  T  G  T  T  G
(SEQ ID NO: 35)
rosa1.4                 T  GGG  A  T  TAT  G  T  A  C  ATA  A  T  CCC  A
(SEQ ID NO: 36)
```

FIGURE 5

| Target sequence (SEQ ID No : 5 to 30) | Target position | First I-CreI variant (SEQ ID NO :82 to 91, 51 and 92 to 106 ) | Second I-CreI variant (SEQ ID NO : 107 to 116, 60, 4, 117 to 130) | minimal repair matrix start | minimal repair matrix end |
|---|---|---|---|---|---|
| cgccctgcgcaacgtggcagg | 3220 | 28K30H32S33S38Q40S44E68C70S75N77I | 28K30D32S33R38T40S44K68E70S75D77R | 3131 | 3330 |
| ccgcaccctctccggagggg | 3490 | 28K30N32N33G38Q40S44K68R70E75N77I | 28K30N32T33Y38W40S44K68E70S75D77R | 3401 | 3600 |
| tggactggctgactcatgca | 4717 | 28K30N32S33R38N40Q44N68R70S75R77D | 28K30H32Y38W40S44Q40S44R68R70S75Q77E | 4628 | 4827 |
| ccagcctggtctacacatcaag | 5584 | 28S30N32S33Y38R40K44D68Y70S75S77R | 28K30N32S33C38A40S44Q68A70K75N77I | 5495 | 5694 |
| ctatctaggatagccaggaata | 5608 | 28K30N32S33C38Q40S44T68R70S75Y77I | 28K30N32D33Y38C40S44D68Y70S75S77R | 5519 | 5718 |
| cagcctgatttccaggggtggg | 5906 | 28K30N32T33C38Q40S44Q68T70N75N77I | 28K30N32T33Y38W40S44R68R70E75N77I | 5817 | 6016 |
| taaacctcataaaatagttag | 5992 | 28K30N32S33Y38Q40S44Q68R70S75R77Y | 28K30N32S33R38A40Q44A68R70S75N77I | 5903 | 6102 |
| tcagattcttatagggaca | 6409 | 28S30N32S33Y38R40K44T68N70N75N77I | 28K30N32S33H38S40S44R68Y70S75Q77N | 6320 | 6519 |
| ttgtatatctcaaataatgctg | 7394 | 28A30N32S33S38R40K44N68Y70S75R77V | 28K30N32T33C38Q40S44A68R70S75N77I | 7305 | 7504 |
| tgagccactgagaatggtctca | 8070 | 28K30N32D33H38Q40S44K68E70S75D77R | 28K30N32D33H38Q40S44D68N70S75N77I | 7981 | 8180 |
| caacatgatgttcataatccca | 8304 | 24V28K30N32S33Y38Q40S44Y68R70S75Q77I | 28E30N32S33Y38R38R40R44A68H70Q75N77I | 8215 | 8414 |
| ttaaatgttgctatgcagttg | 8394 | 28K30R32D33Y38Q40S44Q68S70K75N77I | 28K30N32S33Y38Q40S44Q68R70R75N77I | 8305 | 8504 |
| ttccccaaagttcaaattata | 8583 | 28R30N32S33A38Y40Q44Q68Y70S75R77Q | 28K30N32S33R38A40Q44Q68R70S75D77K | 8494 | 8693 |
| taaacacgtttgtgttataaata | 8678 | 28R30N32S33Y38Q40S44Q68R70R75E77R | 28K30N32D33Y38C40S44R68R70S75R77Y | 8589 | 8788 |
| tatactgtctttagagagtta | 8749 | 28K30N32S33R38A40Q44Q68R70S75N77I | 28K30N32S33Y38Q40S44Q68R70S75Y77R | 8660 | 8859 |
| tgtaatagcttagaaaattaa | 9010 | 28K30N32S33R38A40N40Q44K68Y70S75R77V | 28K30R32D33Y38Q40S44T68H70H75N77I | 8921 | 9120 |
| tttaatctatttggtttgtctag | 9280 | 28K30N32S33P38Q40Q44K68Y70S75Q77N | 28K30N32A33C38Q40S44Q68Y70S75R77Q | 9191 | 9390 |
| ttgtacattgttaggagtgtga | 9556 | 28A30N32S33S38R40K44Q68N70S75N77R | 28K30N32N33G38Q40S44A68A70K75N77I | 9467 | 9666 |
| tgcacttggtacacataattca | 10263 | 28K30H32S33S38Q40S44Y68R70S75D77V | 28K30N32S33R38Q40Q44A68R70S75N77I | 10174 | 10373 |
| tgagatgatacaaagaatttag | 11558 | 28K30N32D33H38Q40S44Q68T70N75N77I | 28K30R32D33Y38Q40S44T68N70N75N77I | 11469 | 11668 |
| ccatcctaaaagaggtcaa | 12391 | 28K30N32R32R33D38Q40S44A68R70S75N77I | 28K30N32S33S38R40H44Q68H70H75N77I | 12302 | 12501 |
| tttaatctattgcaaaggtaa | 12414 | 28K30N32S33P38Q40Q44K68Y70S75Q77N | 28K30N32S33A38Y40Q44T68H70H75N77I | 12325 | 12524 |
| tagtcagtgttatagagttag | 12535 | 28Q30N32S33Y38R40K44A68R70S75E77R | 28K30R32D33Y38Y40Q44S44K68Y70S75Q77N | 12446 | 12645 |
| ttctacgtttcaaatgca | 12791 | 28K30N32S33T38A40S44Q68H70H75N77I | 28K30H32S33S33S38Q40S44Q68R70S75D77R | 12702 | 12901 |
| tttctgtggagacaaaggtaa | 12904 | 28K30N32S33T38Q40T44Q68A70K75N77I | 28R30N32S33A38Y40Q44Q68R70S75D77K | 12815 | 13014 |
| tgagatggctcagcaaataatg | 12954 | 28K30N32D33H38Q40S44N68R70S75R77D | 28K30N32D33Y38C40S44R68R70S75D77K | 12865 | 13064 |

FIGURE 17

MEGANUCLEASE VARIANTS CLEAVING A DNA TARGET SEQUENCE FROM THE MOUSE ROSA26 LOCUS AND USES THEREOF

CROSS-REFERENCE TO RELATED APPLICATIONS

The present application is a 35 U.S.C. §371 National Stage patent application of International patent application PCT/IB2008/002500, filed on Jun. 6, 2008, which claims priority to International patent application PCT/IB2007/002830, filed on Jun. 6, 2007.

The invention relates to a meganuclease variant cleaving a DNA target sequence from the mouse ROSA26 locus, to a vector encoding said variant, to a cell, an animal or a plant modified by said vector and to the use of said meganuclease variant and derived products for mouse genome engineering (recombinant protein production, construction of transgenic mice and recombinant mouse cell lines).

The mouse ROSA26 locus has been discovered by Friedrich and Soriano in 1991 by gene trap experiment using embryonic stem (ES) cells infected with a retrovirus (Friedrich, G. and P. Soriano, Genes & Development, 1991, 5, 1513-1523). The ROSA26 mouse gene trap line, where insertion occurs in intron 1 of the ROSA26 locus; a non-essential site, displays ubiquitous expression of the reporter gene during embryonic development, in newborn (Friedrich and Soriano, 1991, precited) and in hematopoietic cells (Zambrowicz et al., Proc. Natl. Acad. Sci. USA, 1997, 94, 3789-3794). The ROSA26 locus, located in mouse chromosome 6, produces three transcripts (FIG. 1). Two transcripts originate from a common promoter share identical 5' ends (exon 1 and start exon 2), but neither contains a significant ORF. And a third one originated from the reverse strand (Zambrowicz et al., 1997, precited). Transgenes under the control of the mouse ROSA26 promoter show ubiquitous expression in embryo and adult mouse (Soriano, P., Nature Genetics, 1999, 21, 70-71). Targeting the ROSA26 locus in mouse ES cells has been largely used to construct transgenic mouse models (Kisseberth et al., Developmental Biology, 1999, 214, 128-138; Mao X. et al., Proc. Natl. Acad. Sci. USA, 1999, 96, 5037-5042; Soriano, 1999, precited; Awatramani et al., Nature Genetics, 2001, 29, 257-259; Mao X. et al., Blood, 2001, 97, 324-326; Possemato et al., Genesis, 2002, 32, 184-186; Mao, J. et al., Nucleic Acids Res., 2005, 33, e155; Yu et al., Proc. Natl. Acad. Sci. USA, 2005, 102, 8615-8620; International PCT Applications WO 99/53017, WO 02/098217, WO 03/020743, WO 2004/063381 and WO 2005/116070)).

However, the efficacy of homologous recombination in mouse cells is very low (frequency: $10^{-6}$ to $10^{-9}$).

This efficiency can be enhanced by a DNA double-strand break (DSB) in the targeted locus. Such DSBs can be created by Meganucleases, which are by definition sequence-specific endonucleases recognizing large sequences (Thierry, A. and B. Dujon, Nucleic Acids Res., 1992, 20, 5625-5631). These proteins can cleave unique sites in living cells, thereby enhancing gene targeting by 1000-fold or more in the vicinity of the cleavage site (Puchta et al., Nucleic Acids Res., 1993, 21, 5034-5040; Rouet et al., Mol. Cell. Biol., 1994, 14, 8096-8106; Choulika et al., Mol. Cell. Biol., 1995, 15, 1968-1973; Puchta et al., Proc. Natl. Acad. Sci. U.S.A., 1996, 93, 5055-5060; Sargent et al., Mol. Cell. Biol., 1997, 17, 267-277; Cohen-Tannoudji et al., Mol. Cell. Biol., 1998, 18, 1444-1448; Donoho, et al., Mol. Cell. Biol., 1998, 18, 4070-4078; Elliott et al., Mol. Cell. Biol., 1998, 18, 93-101).

However, although several hundreds of natural meganucleases, also referred to as "homing endonucleases" have been identified (Chevalier, B. S. and B. L. Stoddard, Nucleic Acids Res., 2001, 29, 3757-3774), the repertoire of cleavable sequences is too limited to address the complexity of the genomes, and there is usually no cleavable site in a chosen gene. Theoretically, the making of artificial sequence specific endonucleases with chosen specificities could alleviate this limit. Therefore, the making of meganucleases with tailored specificities is under intense investigation.

Recently, fusion of Zinc-Finger Proteins with the catalytic domain of the FokI, a class IIS restriction endonuclease, were used to make functional sequence-specific endonucleases (Smith et al., Nucleic Acids Res., 1999, 27, 674-681; Bibikova et al., Mol. Cell. Biol., 2001, 21, 289-297; Bibikova et al., Genetics, 2002, 161, 1169-1175; Bibikova et al., Science, 2003, 300, 764; Porteus, M. H. and D. Baltimore, Science, 2003, 300, 763-; Alwin et al., Mol. Ther., 2005, 12, 610-617; Urnov et al., Nature, 2005, 435, 646-651; Porteus, M. H., Mol. Ther., 2006, 13, 438-446; International PCT Application WO 2007/014275). Such nucleases could recently be used for the engineering of the ILR2G gene in human cells from the lymphoid lineage (Urnov et al., Nature, 2005, 435, 646-651).

The binding specificity of Cys2-His2 type Zinc-Finger Proteins (ZFP), is easy to manipulate, probably because they represent a simple (specificity driven by essentially four residues per finger), and modular system (Pabo et al., Annu. Rev. Biochem., 2001, 70, 313-340; Jamieson et al., Nat. Rev. Drug Discov., 2003, 2, 361-368. Studies from the Pabo (Rebar, E. J. and C. O. Pabo, Science, 1994, 263, 671-673; Kim, J. S. and C. O. Pabo, Proc. Natl. Acad. Sci. USA, 1998, 95, 2812-2817), Klug (Choo, Y. and A. Klug, Proc. Natl. Acad. Sci. USA, 1994, 91, 11163-11167; Isalan M. and A. Klug, Nat. Biotechnol., 2001, 19, 656-660) and Barbas (Choo, Y. and A. Klug, Proc. Natl. Acad. Sci. USA, 1994, 91, 11163-11167; Isalan M. and A. Klug, Nat. Biotechnol., 2001, 19, 656-660) laboratories resulted in a large repertoire of novel artificial ZFPs, able to bind most G/ANNG/ANNG/ANN sequences.

Nevertheless, ZFPs might have their limitations, especially for applications requiring a very high level of specificity, such as therapeutic applications. It was recently shown that FokI nuclease activity in fusion acts with either one recognition site or with two sites separated by varied distances via a DNA loop including in the presence of some DNA-binding defective mutants of FokI (Catto et al., Nucleic Acids Res., 2006, 34, 1711-1720). Thus, specificity might be very degenerate, as illustrated by toxicity in mammalian cells and *Drosophila* (Bibikova et al., Genetics, 2002, 161, 1169-1175; Bibikova et al., Science, 2003, 300, 764-).

In the wild, meganucleases are essentially represented by homing endonucleases. Homing Endonucleases (HEs) are a widespread family of natural meganucleases including hundreds of proteins families (Chevalier, B. S. and B. L. Stoddard, Nucleic Acids Res., 2001, 29, 3757-3774). These proteins are encoded by mobile genetic elements which propagate by a process called "homing": the endonuclease cleaves a cognate allele from which the mobile element is absent, thereby stimulating a homologous recombination event that duplicates the mobile DNA into the recipient locus. Given their exceptional cleavage properties in terms of efficacy and specificity, they could represent ideal scaffold to derive novel, highly specific endonucleases.

HEs belong to four major families. The LAGLIDADG (SEQ ID NO: 150) family, named after a conserved peptidic motif involved in the catalytic center, is the most widespread and the best characterized group. Seven structures are now available. Whereas most proteins from this family are monomeric and display two LAGLIDADG (SEQ ID NO: 150) motifs, a few ones have only one motif, but dimerize to cleave palindromic or pseudo-palindromic target sequences.

Although the LAGLIDADG (SEQ ID NO: 150) peptide is the only conserved region among members of the family, these proteins share a very similar architecture (FIG. 2). The catalytic core is flanked by two DNA-binding domains with a perfect two-fold symmetry for homodimers such as I-CreI (Chevalier, et al., Nat. Struct. Biol., 2001, 8, 312-316) and I-MsoI (Chevalier et al., J. Mol. Biol., 2003, 329, 253-269) and with a pseudo-symmetry fo monomers such as I-SceI (Moure et al., J. Mol. Biol., 2003, 334, 685-69, I-DmoI (Silva et al., J. Mol. Biol., 1999, 286, 1123-1136) or I-AniI (Bolduc et al., Genes Dev., 2003, 17, 2875-2888). Both monomers, or both domains (for monomeric proteins) contribute to the catalytic core, organized around divalent cations. Just above the catalytic core, the two LAGLIDADG (SEQ ID NO: 150) peptides play also an essential role in the dimerization interface. DNA binding depends on two typical saddle-shaped $\beta\beta\alpha\beta\beta$ folds, sitting on the DNA major groove. Other domains can be found, for example in inteins such as PI-PfuI (Ichiyanagi et al., J. Mol. Biol., 2000, 300, 889-901) and PI-SceI (Moure et al., Nat. Struct. Biol., 2002, 9, 764-770), which protein splicing domain is also involved in DNA binding.

The making of functional chimeric meganucleases, by fusing the N-terminal I-DmoI domain with an I-CreI monomer (Chevalier et al., Mol. Cell., 2002, 10, 895-905 ; Epinat et al., Nucleic Acids Res, 2003, 31, 2952-62; International PCT Applications WO 03/078619 and WO 2004/031346) have demonstrasted the plasticity of LAGLIDADG (SEQ ID NO: 150) proteins.

Besides, different groups have used a rational approach to locally alter the specificity of the I-CreI (Seligman et al., Genetics, 1997, 147, 1653-1664; Sussman et al., J. Mol. Biol., 2004, 342, 31-41; International PCT Applications WO 2006/097784, WO 2006/097853 and WO 2007/049156; Arnould et al., J. Mol. Biol., 2006, 355, 443-458; Rosen et al., Nucleic Acids Res., 2006, 34, 4791-4800; Smith et al., Nucleic Acids Res., Epub 27 Nov. 2006), I-SceI (Doyon et al., J. Am. Chem. Soc., 2006, 128, 2477-2484), PI-SceI (Gimble et al., J. Mol. Biol., 2003, 334, 993-1008) and I-MsoI (Ashworth et al., Nature, 2006, 441, 656-659).

In addition, hundreds of I-CreI derivatives with locally altered specificity were engineered by combining the semi-rational approach and High Throughput Screening:

Residues Q44, R68 and R70 or Q44, R68, D75 and I77 of I-CreI were mutagenized and a collection of variants with altered specificity towards the nucleotides at positions ±3 to 5 of the DNA target (5NNN DNA target) were identified by screening (International PCT Applications WO 2006/097784 and WO 2006/097853; Arnould et al., J. Mol. Biol., 2006, 355, 443-458; Smith et al., Nucleic Acids Res., Epub 27 Nov. 2006).

Residues K28, N30 and Q38, N30, Y33 and Q38 or K28, Y33, Q38 and S40 of I-CreI were mutagenized and a collection of variants with altered specificity towards the nucleotides at positions ±8 to 10 of the DNA target (10NNN DNA target) were identified by screening (Smith et al., Nucleic Acids Res., Epub 27 Nov. 2006; International PCT Application WO 2007/049156).

Residues 28 to 40 and 44 to 77 of I-CreI were shown to form two separable functional subdomains, able to bind distinct parts of a homing endonuclease half-site (Smith et al. Nucleic Acids Res., Epub 27 Nov. 2006; International PCT Application WO 2007/049095).

The combination of mutations from the two subdomains of I-CreI within the same monomer allowed the design of novel chimeric molecules (homodimers) able to cleave a palindromic combined DNA target sequence comprising the nucleotides at positions ±3 to 5 and ±8 to 10 which are bound by each subdomain (Smith et al., Nucleic Acids Res., Epub 27 Nov. 2006; International PCT Application WO 2007/049156).

Two different variants were combined and assembled in a functional heterodimeric endonuclease able to cleave a chimeric target resulting from the fusion of a different half of each variant DNA target sequence (Arnould et al., precited; International PCT Application WO 2006/097854). Interestingly, the novel proteins had kept proper folding and stability, high activity, and a narrow specificity The combination of the two former steps allows a larger combinatorial approach, involving four different subdomains. The different subdomains can be modified separately and combined to obtain an entirely redesigned meganuclease variant (heterodimer or single-chain molecule) with chosen specificity, as illustrated on FIG. 3. In a first step, couples of novel meganucleases are combined in new molecules ("half-meganucleases") cleaving palindromic targets derived from the target one wants to cleave. Then, the combination of such "half-meganuclease" can result in a heterodimeric species cleaving the target of interest. The assembly of four set of mutations into heterodimeric endonucleases cleaving a model target sequence or a sequence from the human RAG1 gene has been described in Smith et al. (Nucleic Acids Res., Epub 27 Nov. 2006).

However, the targets tested in this report were identical to the original sequence of the palindromic I-CreI site (C1221; FIG. 5) at the positions ±2 and ±1. Even though the base-pairs ±1 and ±2 do not display any contact with the protein, it has been shown that these positions are not devoid of content information (Chevalier et al., J. Mol. Biol., 2003, 329, 253-269), especially for the base-pair ±1 and could be a source of additional substrate specificity (Argast et al., J. Mol. Biol., 1998, 280, 345-353; Jurica et al., Mol. Cell., 1998, 2, 469-476; Chevalier, B. S. and B. L. Stoddard, Nucleic Acids Res., 2001, 29, 3757-3774). In vitro selection of cleavable I-CreI target (Argast et al., precited) randomly mutagenized, revealed the importance of these four base-pairs on protein binding and cleavage activity. It has been suggested that the network of ordered water molecules found in the active site was important for positioning the DNA target (Chevalier et al., Biochemistry, 2004, 43, 14015-14026). In addition, the extensive conformational changes that appear in this region upon I-CreI binding suggest that the four central nucleotides could contribute to the substrate specificity, possibly by sequence dependent conformational preferences (Chevalier et al., 2003, precited).

Thus, it was not clear if mutants identified on 10NNN and 5NNN DNA targets as homodimers cleaving a palindromic sequence with the four central nucleotides being gtac, would allow the design of new endonucleases that would cleave targets containing changes in the four central nucleotides.

The Inventors have identified a series of DNA targets in the mouse ROSA26 locus that could be cleaved by I-CreI variants (FIG. 17). The combinatorial approach described in FIG. 3 was used to entirely redesign the DNA binding domain of the I-CreI protein and thereby engineer novel meganucleases with fully engineered specificity, to cleave a DNA target from the mouse ROSA26 locus (rosa1) which differs from the I-CreI C1221 22 bp palindromic site by 13 nucleotides including one (position +1) of the four central nucleotides (FIG. 5).

Even though the combined variants were initially identified towards nucleotides 10NNN and 5NNN respectively, and a strong impact of the four central nucleotides of the target on the activity of the engineered meganuclease was observed, functional meganucleases with a profound change in specificity were selected. Furthermore, the activity of the engineered protein could be significantly improved by two successive rounds of random mutagenesis and screening, to compare with the activity of the I-CreI protein.

The ability to generate a double-strand break at the ROSA26 locus provides a means to significantly enhance homologous recombination at the locus. Thus, a meganuclease targeting the ROSA26 locus will allow efficient gene insertions in mouse cells (FIG. 4). The ability to efficiently insert genes (knock-in) at this locus has the advantage of allowing reproducible expression levels as well as predictable time lines for generating insertions. Potential applications include the production of recombinant proteins in mouse cells and the engineering of transgenic mice and recombinant mouse cell lines, that can be used, for example, for protein production, gene function studies, drug screening, or as disease model.

The invention relates to an I-CreI variant wherein at least one of the two I-CreI monomers has at least two substitutions one in each of the two functional subdomains of the LAGLIDADG (SEQ ID NO: 150) core domain situated respectively from positions 26 to 40 and 44 to 77 of I-CreI and is able to cleave a DNA target sequence from the mouse ROSA26 locus.

The cleavage activity of the variant according to the invention may be measured by any well-known, in vitro or in vivo cleavage assay, such as those described in the International PCT Application WO 2004/067736; Epinat et al., Nucleic Acids Res., 2003, 31, 2952-2962; Chames et al., Nucleic Acids Res., 2005, 33, e178 and Arnould et al., J. Mol. Biol., 2006, 355, 443-458. For example, the cleavage activity of the variant of the invention may be measured by a direct repeat recombination assay, in yeast or mammalian cells, using a reporter vector. The reporter vector comprises two truncated, non-functional copies of a reporter gene (direct repeats) and the genomic DNA target sequence within the intervening sequence, cloned in a yeast or a mammalian expression vector. Expression of the variant results in a functional endonuclease which is able to cleave the genomic DNA target sequence. This cleavage induces homologous recombination between the direct repeats, resulting in a functional reporter gene, whose expression can be monitored by appropriate assay.

Definitions

Amino acid refers to a natural or synthetic amino acid including enantiomers and stereoisomers of the preceding amino acids.

Amino acid residues in a polypeptide sequence are designated herein according to the one-letter code, in which, for example, Q means Gln or Glutamine residue, R means Arg or Arginine residue and D means Asp or Aspartic acid residue.

Acidic amino acid refers to aspartic acid (D) and Glutamic acid (E).

Basic amino acid refers to lysine (K), arginine (R) and histidine (H).

Small amino acid refers to glycine (G) and alanine (A).

Aromatic amino acid refers to phenylalanine (F), tryptophane (W) and tyrosine (Y).

Nucleotides are designated as follows: one-letter code is used for designating the base of a nucleoside: a is adenine, t is thymine, c is cytosine, and g is guanine. For the degenerated nucleotides, r represents g or a (purine nucleotides), k represents g or t, s represents g or c, w represents a or t, m represents a or c, y represents t or c (pyrimidine nucleotides), d represents g, a or t, v represents g, a or c, b represents g, t or c, h represents a, t or c, and n represents g, a, t or c.

by "meganuclease", is intended an endonuclease having a double-stranded DNA target sequence of 12 to 45 bp. Said meganuclease is either a dimeric enzyme, wherein each domain is on a monomer or a monomeric enzyme comprising the two domains on a single polypeptide.

by "meganuclease domain" is intended the region which interacts with one half of the DNA target of a meganuclease and is able to associate with the other domain of the same meganuclease which interacts with the other half of the DNA target to form a functional meganuclease able to cleave said DNA target.

by "meganuclease variant" or "variant" is intended a meganuclease obtained by replacement of at least one residue in the amino acid sequence of the wild-type meganuclease (natural meganuclease) with a different amino acid.

by "functional variant" is intended a variant which is able to cleave a DNA target sequence, preferably said target is a new target which is not cleaved by the parent meganuclease. For example, such variants have amino acid variation at positions contacting the DNA target sequence or interacting directly or indirectly with said DNA target.

by "meganuclease variant with novel specificity" is intended a variant having a pattern of cleaved targets different from that of the parent meganuclease. The terms "novel specificity", "modified specificity", "novel cleavage specificity", "novel substrate specificity" which are equivalent and used indifferently, refer to the specificity of the variant towards the nucleotides of the DNA target sequence.

by "I-CreI" is intended the wild-type I-CreI having the sequence SWISSPROT P05725, corresponding to the sequence SEQ ID NO: 1 in the sequence listing or the sequence pdb accession code 1g9y, corresponding to the sequence SEQ ID NO: 133 in the sequence listing.

by "domain" or "core domain" is intended the "LAGLIDADG (SEQ ID NO: 150) homing endonuclease core domain" which is the characteristic $\alpha_1\beta_1\beta_2\alpha_2\beta_3\beta_4\alpha_3$ fold of the homing endonucleases of the LAGLIDADG (SEQ ID NO: 150) family, corresponding to a sequence of about one hundred amino acid residues. Said domain comprises four beta-strands ($\beta_1\beta_2\beta_3\beta_4$) folded in an antiparallel beta-sheet which interacts with one half of the DNA target. This domain is able to associate with another LAGLIDADG (SEQ ID NO: 150) homing endonuclease core domain which interacts with the other half of the DNA target to form a functional endonuclease able to cleave said DNA target. For example, in the case of the dimeric homing endonuclease I-CreI (163 amino acids), the LAGLIDADG (SEQ ID NO: 150) homing endonuclease core domain corresponds to the residues 6 to 94.

by "single-chain meganuclease" is intended a meganuclease comprising two LAGLIDADG (SEQ ID NO: 150) homing endonuclease domains or core domains linked by a peptidic spacer. The single-chain meganuclease is able to cleave a chimeric DNA target sequence comprising one different half of each parent meganuclease target sequence.

by "subdomain" is intended the region of a LAGLIDADG (SEQ ID NO: 150) homing endonuclease core domain which interacts with a distinct part of a homing endonuclease DNA target half-site. Two different subdomains behave independently and the mutation in one subdomain does not alter the binding and cleavage properties of the other subdomain. Therefore, two subdomains bind distinct part of a homing endonuclease DNA target half-site.

by "beta-hairpin" is intended two consecutive beta-strands of the antiparallel beta-sheet of a LAGLIDADG (SEQ ID NO: 150) homing endonuclease core domain (($\beta_1\beta_2$ or, $\beta_3\beta_4$) which are connected by a loop or a turn.

by "I-CreI site" is intended a 22 to 24 bp double-stranded DNA sequence which is cleaved by I-CreI. I-CreI sites include the wild-type (natural) non-palindromic I-CreI homing site and the derived palindromic sequences such as the sequence 5'-$t_{-12}c_{-11}a_{-10}a_{-9}a_{-8}a_{-7}c_{-6}g_{-5}t_{-4}c_{-3}g_{-2}t_{-1}a_{+1}c_{+2}g_{+3}a_{+4}c_{+5}g_{+6}t_{+7}t_{+8}t_{+9}t_{+10}g_{+11}a_{+12}$ also called C1221 (SEQ ID NO:2; FIG. 5).

by "DNA target", "DNA target sequence", "target sequence", "target-site", "target", "site"; "site of interest"; "recognition site", "recognition sequence", "homing recognition site", "homing site", "cleavage site" is intended a 20 to 24 by double-stranded palindromic, partially palindromic (pseudo-palindromic) or non-palindromic polynucleotide sequence that is recognized and cleaved by a LAGLIDADG (SEQ ID NO: 150) homing endonuclease such as I-CreI, or a variant, or a single-chain chimeric meganuclease derived from I-CreI. These terms refer to a distinct DNA location, preferably a genomic location, at which a double stranded break (cleavage) is to be induced by the meganuclease. The DNA target is defined by the 5' to 3' sequence of one strand of the double-stranded polynucleotide, as indicate above for C1221. Cleavage of the DNA target occurs at the nucleotides at positions +2 and −2, respectively for the sense and the antisense strand. Unless otherwiwe indicated, the position at which cleavage of the DNA target by an I-CreI meganuclease variant occurs, corresponds to the cleavage site on the sense strand of the DNA target.

by "DNA target half-site", "half cleavage site" or half-site" is intended the portion of the DNA target which is bound by each LAGLIDADG (SEQ ID NO: 150) homing endonuclease core domain.

by "chimeric DNA target" or "hybrid DNA target" is intended the fusion of a different half of two parent meganuclease target sequences. In addition at least one half of said target may comprise the combination of nucleotides which are bound by at least two separate subdomains (combined DNA target).

by "mouse ROSA26 locus" is intended the locus located in mouse chromosome 6 and having the sequence corresponding to EMBL accession number CQ880114 (SEQ ID NO: 3; 13139 bp). The ROSA26 produces three transcripts (FIG. 1): two transcripts originate from a common promoter share identical 5' ends (exon 1 and exon 2 start), but neither contains a significant ORF. And a third one originated from the reverse strand.

by "DNA target sequence from the mouse ROSA26 locus", "genomic DNA target sequence", "genomic DNA cleavage site", "genomic DNA target" or "genomic target" is intended a 20 to 24 bp sequence of the mouse ROSA26 locus which is recognized and cleaved by a meganuclease variant.

by "vector" is intended a nucleic acid molecule capable of transporting another nucleic acid to which it has been linked.

by "homologous" is intended a sequence with enough identity to another one to lead to a homologous recombination between sequences, more particularly having at least 95% identity, preferably 97% identity and more preferably 99%.

"identity" refers to sequence identity between two nucleic acid molecules or polypeptides. Identity can be determined by comparing a position in each sequence which may be aligned for purposes of comparison. When a position in the compared sequence is occupied by the same base, then the molecules are identical at that position. A degree of similarity or identity between nucleic acid or amino acid sequences is a function of the number of identical or matching nucleotides at positions shared by the nucleic acid sequences. Various alignment algorithms and/or programs may be used to calculate the identity between two sequences, including FASTA, or BLAST which are available as a part of the GCG sequence analysis package (University of Wisconsin, Madison, Wis.), and can be used with, e.g., default settings.

"individual" includes mammals, as well as other vertebrates (e.g., birds, fish and reptiles). The terms "mammal" and "mammalian", as used herein, refer to any vertebrate animal, including monotremes, marsupials and placental, that suckle their young and either give birth to living young (eutharian or placental mammals) or are egg-laying (metatharian or nonplacental mammals). Examples of mammalian species include humans and other primates (e.g., monkeys, chimpanzees), rodents (e.g., rats, mice, guinea pigs) and others such as for example: cows, pigs and horses.

by mutation is intended the substitution, deletion, insertion of one or more nucleotides/amino acids in a polynucleotide (cDNA, gene) or a polypeptide sequence. Said mutation can affect the coding sequence of a gene or its regulatory sequence. It may also affect the structure of the genomic sequence or the structure/stability of the encoded mRNA.

The variant according to the present invention may be a homodimer or a heterodimer. Preferably, both monomers of the heterodimer are mutated at positions 26 to 40 and/or 44 to 77. More preferably, both monomers have different substitutions both at positions 26 to 40 and 44 to 77 of I-CreI In a preferred embodiment of said variant, said substitution(s) in the subdomain situated from positions 44 to 77 of I-CreI are at positions 44, 68, 70, 75 and/or 77.

In another preferred embodiment of said variant, said substitution(s) in the subdomain situated from positions 26 to 40 of I-CreI are at positions 26, 28, 30, 32, 33, 38 and/or 40.

In another preferred embodiment of said variant, said substitutions are replacement of the initial amino acids with amino acids selected from the group consisting of: A, D, E, G, H, K, N, P, Q, R, S, T, Y, C, V, L and W.

In another preferred embodiment of said variant, it comprises one or more mutations at positions of other amino acid residues which contact the DNA target sequence or interact with the DNA backbone or with the nucleotide bases, directly or via a water molecule; these residues are well-known in the art (Jurica et al., Molecular Cell., 1998, 2, 469-476; Chevalier et al., J. Mol. Biol., 2003, 329, 253-269).

In particular, additional substitutions may be introduced at positions contacting the phosphate backbone, for example in the final C-terminal loop (positions 137 to 143; Prieto et al., Nucleic Acids Res., Epub 22 Apr. 2007). Preferably said residues are involved in binding and cleavage of said DNA cleavage site. More preferably, said residues are at positions 138, 139, 142 or 143 of I-CreI. Two residues may be mutated in one variant provided that each mutation is in a different pair of residues chosen from the pair of residues at positions 138 and 139 and the pair of residues at positions 142 and 143. The mutations which are introduced modify the interaction(s) of said amino acid(s) of the final C-terminal loop with the phosphate backbone of the I-CreI site. Preferably, the residue at position 138 or 139 is substituted by an hydrophobic amino acid to avoid the formation of hydrogen bonds with the phosphate backbone of the DNA cleavage site. For example, the residue at position 138 is substituted by an alanine or the residue at position 139 is substituted by a methionine. The residue at position 142 or 143 is advantageously substituted by a small amino acid, for example a glycine, to decrease the size of the side chains of these amino acid residues. More, preferably, said substitution in the final C-terminal loop modify the specificity of the variant towards the nucleotide at positions ±1 to 2, ±6 to 7 and/or ±11 to 12 of the I-CreI site.

In another preferred embodiment of said variant, it comprises one or more additional mutations that improve the binding and/or the cleavage properties of the variant towards the DNA target sequence from the mouse ROSA26 locus.

The additional residues which are mutated may be on the entire I-CreI sequence, and in particular in the C-terminal half of I-CreI (positions 80 to 163). For example, the variant comprises one or more additional substitution at positions 19, 24, 79, 105, 107, 151, 153, 158. Said substitutions are advantageously selected from the group consisting of: G19S, I24V, S79G, V105A, K107R, V151A, D153G and K158E.

The variant of the invention may be derived from the wild-type I-CreI (SEQ ID NO: 1 or 133) or an I-CreI scaffold protein having at least 85% identity, preferably at least 90% identity, more preferably at least 95% identity with SEQ ID NO: 133, such as the scaffold of SEQ ID NO: 4 (167 amino acids) having the insertion of an alanine at position 2, the substitution D75N, and the insertion of AAD at the C-terminus (positions 164 to 166) of the I-CreI sequence.

In addition, the variants of the invention may include one or more residues inserted at the $NH_2$ terminus and/or COOH terminus of the sequence. For example, a tag (epitope (HA-tag (YPYDVPDYA; SEQ ID NO: 135) or S-tag (KETAAAK-FERQHMDS; SEQ ID NO: 136) or polyhistidine sequence) is introduced at the $NH_2$ terminus and/or COOH terminus; said tag is useful for the detection and/or the purification of said variant. When the tag is introduced at the $NH_2$ terminus, the sequence of the tag may either replace the first amino acids of the variant (at least the first methionine and eventually the second amino acid of the variant; tag starting with a methionine) or be inserted between the first (methionine) and the second amino acids or the first and the third amino acids of the variant (tag with no methionine).

The variant may also comprise a nuclear localization signal (NLS); said NLS is useful for the importation of said variant into the cell nucleus. An example of NLS is KKKRK (SEQ ID NO: 134). The NLS may be inserted just after the first methionine of the variant or just after an N-terminal tag.

The variant according to the present invention may be a homodimer which is able to cleave a palindromic or pseudo-palindromic DNA target sequence.

Alternatively, said variant is a heterodimer, resulting from the association of a first and a second monomer having different substitutions at positions 26 to 40 and/or 44 to 77 of I-CreI, said heterodimer being able to cleave a non-palindromic DNA target sequence from the mouse ROSA26 locus.

The DNA target sequence which is cleaved by said variant may be in an exon or in an intron of the mouse ROSA26 locus.

In another preferred embodiment of said variant, said DNA target is selected from the group consisting of the sequences SEQ ID NO: 5 to 30 (FIG. 17) which cover all of the mouse ROSA26 locus.

TABLE I

ROSA26 locus target sequences

| SEQ ID NO: | Target sequence | Target position* | Target location |
|---|---|---|---|
| 5 | cgccctgcgcaacgtggcagg | 3220 | Intron 1 |
| 6 | ccgcaccttctccggaggggg | 3490 | Intron 1 |
| 7 | tggactggcttgactcatggca | 4717 | Intron 1 |
| 8 | ccagcctggtctacacatcaag | 5584 | Intron 1 |
| 9 | ctatctaggatagccaggaata | 5608 | Intron 1 |
| 10 | cagcctgatttccagggtgggg | 5906 | Intron 1 |
| 11 | taaacctcataaaatagttatg | 5992 | Intron 1 |
| 12 | tcagattcttttataggggaca | 6409 | Intron 1 |
| 13 | ttgtatatctcaaataatgctg | 7394 | Intron 1 |
| 14 | tgagccactgagaatggtctca | 8070 | Intron 1 |
| 15 | caacatgatgttcataatccca | 8304 | Exon 2 |
| 16 | ttaaatgttgctatgcagtttg | 8394 | Exon 2 |
| 17 | ttccccaaagttccaaattata | 8583 | Exon 2 |
| 18 | taacaccgtttgtgttataata | 8678 | Exon 2 |
| 19 | tatactgtcttagagagttta | 8749 | Exon 2 |
| 20 | tgtaatagcttagaaaatttaa | 9010 | Exon 2 |
| 21 | tttaatctattggtttgtctag | 9280 | Intron 2 |
| 22 | ttgtacattgttaggagtgtga | 9556 | Intron 2 |
| 23 | tgcactggtacacataatttca | 10263 | Intron 2 |
| 24 | tgagatgatacaaagaatttag | 11558 | Intron 2 and antisense transcript |
| 25 | ccatcctataaaagaaggtcaa | 12391 | Exon 3 or antisense transcript |
| 26 | tttaatctattgcaaaaggtaa | 12414 | Exon 3 or antisense transcript |
| 27 | tagtccagtgttatagagttag | 12535 | Exon 3 or antisense transcript |
| 28 | ttctaccttttccaaatggca | 12791 | Exon 3 or antisense transcript |
| 29 | ttttctgtggagacaaaggtaa | 12904 | Exon 3 or antisense transcript |

TABLE I-continued

ROSA26 locus target sequences

| SEQ ID NO: | Target sequence | Target position* | Target location |
|---|---|---|---|
| 30 | tgagatggctcagcaaataatg | 12954 | Exon 3 or antisense transcript |

*the indicated position is that of the first nucleotide of the target

More preferably, the monomers of the variant have at least the following substitutions, respectively for the first and the second monomer:

N30H, Y33S, Q44E, R68C, R70S and D75N (first monomer), and N30D, Y33R, Q38T, Q44K, R68E, R70S, and I77R (second monomer); this variant cleaves the ROSA26 target SEQ ID NO: 5 which is located in the first intron (FIGS. 1 and 17; Table I), S32N, Y33G, Q44K, R70E and D75N (first monomer), and S32T, Q38W, Q44K, R68E, R70S and I77R (second monomer); this variant cleaves the ROSA26 target SEQ ID NO: 6 which is located in the first intron (FIGS. 1 and 17; Table I), Y33R, Q38N, S40Q, Q44N, R70S, D75R and I77D (first monomer), and N30H, Y33S, Q44A, R70S, D75Q and I77E (second monomer); this variant cleaves the ROSA26 target SEQ ID NO: 7 which is located in the first intron (FIGS. 1 and 17; Table I), K28S, Q38R, S40K, Q44D, R68Y, R70S, D75S and I77R (first monomer), and Y33C, Q38A, R68A, R70K and D75N (second monomer); this variant cleaves the ROSA26 target SEQ ID NO: 8 which is located in the first intron (FIGS. 1 and 17; Table I), Y33C, Q44T, R70S and D75Y (first monomer), and S32D, Q38C, Q44D, R68Y, R70S, D75S and I77R (second monomer); this variant cleaves the ROSA26 target SEQ ID NO: 9 which is located in the first intron (FIGS. 1 and 17; Table I), S32T, Y33C, R68T, R70N and D75N (first monomer), and S32T, Q38W, Q44K, R70E and D75N (second monomer); this variant cleaves the ROSA26 target SEQ ID NO: 10 which is located in the first intron (FIGS. 1 and 17; Table I), R70S, D75R and I77Y ((first monomer), and Y33R, Q38A, S40Q, Q44A, R70S and D75N (second monomer); this variant cleaves the ROSA26 target SEQ ID NO: 11 which is located in the first intron (FIGS. 1 and 17; Table I), K28S, Q38R, S40K, Q44T, R68N, R70N and D75N (first monomer), and Y33H, Q38S, Q44K, R68Y, R70S, D75Q and I77N (second monomer); this variant cleaves the ROSA26 target SEQ ID NO: 12 which is located in the first intron (FIGS. 1 and 17; Table I), K28A, Y33S, Q38R, S40K, Q44N, R68Y, R70S, D75R, I77V (first monomer), and S32T, Y33C, Q44A, R70S and D75N (second monomer); this variant cleaves the ROSA26 target SEQ ID NO: 13 which is located in the first intron (FIGS. 1 and 17; Table I), S32D, Y33H, Q44K, R68E, R70S and I77R (first monomer), and S32D, Y33H, Q44D, R68N, R70S and D75N (second monomer); this variant cleaves the ROSA26 target SEQ ID NO: 14 which is located in the first intron (FIGS. 1 and 17; Table I), N30R, S32D, R68S, R70K and D75N (first monomer), and D75N (second monomer); this variant cleaves the ROSA26 target SEQ ID NO: 16 which is located in the second exon (FIGS. 1 and 17; Table I), K28R, Y33A, Q38Y, S40Q, R68Y, R70S, D75T and I77Q (first monomer), and Y33R, Q38A, S40Q, R70S and I77K (second monomer); this variant cleaves the ROSA26 target SEQ ID NO: 17 which is located in the second exon (FIGS. 1 and 17; Table I), K28R, N30D, D75E and I77R (first monomer), and S32D, Q38C, Q44A, R70S, D75R and I77Y (second monomer); this variant cleaves the ROSA26 target SEQ ID NO: 18 which is located in the second exon (FIGS. 1 and 17; Table I), Y33R, Q38A; S40Q, R70S, and D75N (first monomer), and R70S, D75Y and I77R (second monomer); this variant cleaves the ROSA26 target SEQ ID NO: 19 which is located in the second exon (FIGS. 1 and 17; Table I), Y33R, Q38A, S40Q, Q44N, R68Y, R70S, D75R and I77V (first monomer), and N30R, S32D, Q44T, R68H, R70H and D75N (second monomer); this variant cleaves the ROSA26 target SEQ ID NO: 20 which is located in the second exon (FIGS. 1 and 17; Table I), Y33P, S40Q, Q44K, R68Y, R70S, D75Q and I77N (first monomer), and S32A, Y33C, R68Y, R70S, D75R and I77Q (second monomer); this variant cleaves the ROSA26 target SEQ ID NO: 21 which is located in the second intron (FIGS. 1 and 17; Table I), K28A, Y33S, Q38R, S40K, R68N, R70S, D75N and I77R (first monomer), and S32N, Y33G, Q44A, R68A, R70K and D75N (second monomer); this variant cleaves the ROSA26 target SEQ ID NO: 22 which is located in the second intron (FIGS. 1 and 17; Table I), N30H, Y33S, Q44Y, R70S and I77V (first monomer), and Y33R, S40Q, Q44A, R70S and D75N (second monomer); this variant cleaves the ROSA26 target SEQ ID NO: 23 which is located in the second intron (FIGS. 1 and 17; Table I), S32D, Y33H, R68T, R70N and D75N (first monomer), and N30R, S32D, Q44T, R68N, R70N and D75N (second monomer); this variant cleaves the ROSA26 target SEQ ID NO: 24 which is located in the second intron and in the antisense transcript (FIGS. 1 and 17; Table I), S32R, Y33D, Q44A, R70S and D75N (first monomer), and Y33S, Q38R, S40H, R68H, R70H and D75N (second monomer); this variant cleaves the ROSA26 target SEQ ID NO: 25 which is located in the third exon or the antisense transcript (FIGS. 1 and 17; Table I), Y33P, S40Q, Q44K, R68Y, R70S, D75Q and I77N (first monomer), and K28R, Y33A, Q38Y, S40Q, Q44T, R68H, R70H and D75N (second monomer); this variant cleaves the ROSA26 target SEQ ID NO: 26 which is located in the third exon or the antisense transcript (FIGS. 1 and 17; Table I), K28Q, Q38R, S40K, Q44A, R70S, D75E and I77R (first monomer), and N30R, S32D, Q44K, R68Y, R70S, D75Q and I77N (second monomer); this variant cleaves the ROSA26 target SEQ ID NO: 27 which is located in the third exon or the antisense transcript (FIGS. 1 and 17; Table I), Y33T, Q38A, R68H, R70H and D75N (first monomer), and N30H, Y33S, R70S and I77K (second monomer); this variant cleaves the ROSA26 target SEQ ID NO: 28 which is located in the third exon or the antisense transcript (FIGS. 1 and 17; Table I), Y33T, S40T, R68A, R70K and D75N (first monomer), and K28R, Y33A, Q38Y, S40Q, R70S and I77K (second monomer); this variant cleaves the ROSA26 target SEQ ID NO: 29 which is located in the third exon or the antisense transcript (FIGS. 1 and 17; Table I), and S32D, Y33H, Q44N, R70S, D75R and I77D (first monomer), and S32D, Q38C, R70S and I77K (second monomer); this variant cleaves the ROSA26 target SEQ ID NO: 30 which is located in the third exon or the antisense transcript (FIGS. 1 and 17; Table I).

Examples of said variants cleaving the ROSA26 DNA targets of Table I (nucleotide sequences SEQ ID NO: 5 to 14 and 16 to 30) include the variants having a first monomer of any of the amino acid sequences SEQ ID NO: 82 to 106 and a second monomer of any of the amino acid sequences SEQ ID NO: 107 to 116, 4, 117 to 130, respectively (FIG. 17).

In addition, the following variants are able to cleave the ROSA26 DNA target, named rosa1, which is located in the second exon (FIGS. 1 and 17; Table I):

the forty variants having a first monomer selected from the group consisting of: I24V, Q44Y, R70S and D75N; I24V, Q44Y, R68Y, R70S, D75Y and I77R; I24V, Q44Y, R70S, D75N and I77V; I24V, Q44Y, R68N, R70S and D75R; I24V, Q44Y, R68S, R70S and D75R; I24V, Q44Y, R70S and D75Q; I24V, Q44Y, R68Y, R70S, D75R and I77V; I24V, Q44Y, R70S, D75Y and I77T, and a second monomer selected in the group consisting of: K28E, Y33R, Q38R, S40R, Q44A, R68H, R70Q and D75N; K28E, Y33R, Q38R, S40R, Q44A, R68N and D75N; K28E, Y33R, Q38R, S40K, Q44A, R68H, R70Q and D75N; K28E, Y33R, Q38R, S40K, Q44V, R70A and D75N; K28E, Y33R, Q38R, S40K, Q44A, R70G and D75N; examples of these variants are presented in Table V (first monomer: m2, m6, m8, m12, m13, m14, m16 or m17 (SEQ ID NO: 39, 43, 45, 49, 50, 51, 53 and 54); second monomer any of the SEQ ID NO: 60, 61, 63, 65 and 66)

the variant having a first monomer comprising I24V, Q44Y, R70S, D75Y and I77T and K28E, Y33R, Q38R, S40R, Q44A, R68S, R70Q and D75N (second monomer); an example of this variant is presented in Table V (first monomer m17 (SEQ ID NO:54) and second monomer SEQ ID NO: 62).

the ten variants having a first monomer selected from the group consisting of I24V, Q44Y, R68N, R70S and D75R; I24V, Q44Y, R68S, R70S and D75R; I24V, Q44Y, R70S and D75Q; I24V, Q44Y, R68Y, R70S, D75R and I77V; I24V, Q44Y, R70S, D75Y and I77T, and a second monomer selected in the group consisting of: K28E, Y33R, Q38R, S40K, Q44A, R70S and D75N and K28E, Y33R, Q38R, S40K, Q44A, R68T, R70N and D75N; examples of these variants are presented in Table V (first monomer: m12, m13, m14, m16 or m17 (SEQ ID NO: 49, 50, 51, 53 and 54); second monomer any of the SEQ ID NO: 64 and 67).

the variants having a first monomer consisting of the sequence SEQ ID NO: 72 (MO_1; Tables VI and VII) or SEQ ID NO: 73 (MO_2; Tables VI and VII) and a second monomer consisting of any of the sequences SEQ ID NO: 74 to 77 (mO_1 to mO_4; Table VII); these eight variants have additional substitutions that increase the cleavage activity of the variants for the rosa1 target.

The invention encompasses I-CreI variants having at least 85% identity, preferably at least 90% identity, more preferably at least 95% (96%, 97%, 98%, 99%) identity with the sequences as defined above, said variant being able to cleave a DNA target from the mouse ROSA26 locus.

For example, the invention encompasses the I-CreI variants derived from MO_1 and mO_2 bp insertion of a NLS, a tag or both, which are selected from the group consisting of the sequences SEQ ID NO: 140 to 145.

The heterodimeric variant is advantageously an obligate heterodimer variant having at least one pair of mutations interesting corresponding residues of the first and the second monomers which make an intermolecular interaction between the two I-CreI monomers, wherein the first mutation of said pair(s) is in the first monomer and the second mutation of said pair(s) is in the second monomer and said pair(s) of mutations prevent the formation of functional homodimers from each monomer and allow the formation of a functional heterodimer, able to cleave the genomic DNA target from the mouse ROSA26 locus.

To form an obligate heterodimer, the monomers have advantageously at least one of the following pairs of mutations, respectively for the first and the second monomer:

a) the substitution of the glutamic acid at position 8 with a basic amino acid, preferably an arginine (first monomer) and the substitution of the lysine at position 7 with an acidic amino acid, preferably a glutamic acid (second monomer); the first monomer may further comprise the substitution of at least one of the lysine residues at positions 7 and 96, by an arginine.

b) the substitution of the glutamic acid at position 61 with a basic amino acid, preferably an arginine (first monomer) and the substitution of the lysine at position 96 with an acidic amino acid, preferably a glutamic acid (second monomer); the first monomer may further comprise the substitution of at least one of the lysine residues at positions 7 and 96, by an arginine c) the substitution of the leucine at position 97 with an aromatic amino acid, preferably a phenylalanine (first monomer) and the substitution of the phenylalanine at position 54 with a small amino acid, preferably a glycine (second monomer); the first monomer may further comprise the substitution of the phenylalanine at position 54 by a tryptophane and the second monomer may further comprise the substitution of the leucine at position 58 or lysine at position 57, by a methionine, and d) the substitution of the aspartic acid at position 137 with a basic amino acid, preferably an arginine (first monomer) and the substitution of the arginine at position 51 with an acidic amino acid, preferably a glutamic acid (second monomer).

For example, the first monomer may have the mutation D137R and the second monomer, the mutation R51D. The obligate heterodimer meganuclease comprises advantageously, at least two pairs of mutations as defined in a), b) c) or d), above; one of the pairs of mutation is advantageously as defined in c) or d). Preferably, one monomer comprises the substitution of the lysine residues at positions 7 and 96 by an acidic amino acid (aspartic acid (D) or glutamic acid (E)), preferably an aspartic acid (K7E and K96E) and the other monomer comprises the substitution of the glutamic acid residues at positions 8 and 61 by a basic amino acid (arginine (R) or lysine (K); for example, E8K and E61R). More preferably, the obligate heterodimer meganuclease, comprises three pairs of mutations as defined in a), b) and c), above. The obligate heterodimer meganuclease consists advantageously of (i) E8R, E8K or E8H, E61R, E61K or E61H and L97F, L97W or L97Y; (ii) K7R, E8R, E61R, K96R and L97F, or (iii) K7R, E8R, F54W, E61R, K96R and L97F and a second monomer (B) having at least the mutations (iv) K7E or K7D, F54G or F54A and K96D or K96E; (v) K7E, F54G, L58M and K96E, or (vi) K7E, F54G, K57M and K96E. For example, the first monomer may have the mutations K7R, E8R or E8K, E61R, K96R and L97F or K7R, E8R or E8K, F54W, E61R, K96R and L97F and the second monomer, the mutations K7E, F54G, L58M and K96E or K7E, F54G, K57M and K96E. An example of heterodimer is SEQ ID NO: 147 and SEQ ID NO: 148. The obligate heterodimer may comprise at least one NLS and/or one tag as defined above; said NLS and/or tag may be in the first and/or the second monomer.

The subject-matter of the present invention is also a single-chain chimeric meganuclease (fusion protein) derived from an I-CreI variant as defined above. The single-chain meganuclease may comprise two I-CreI monomers, two I-CreI core domains (positions 6 to 94 of I-CreI) or a combination of both. Preferably, the two monomers/core domains or the combination of both, are connected by a peptidic linker. An example of peptidic linker is SEQ ID NO: 149. An example of single-chain chimeric meganuclease is SEQ ID NO: 146. The single-chain chimeric meganuclease may further comprise at least one NLS and/or one tag as defined above; said NLS and/or tag may be in the first and/or the second monomer.

The subject-matter of the present invention is also a polynucleotide fragment encoding a variant or a single-chain chimeric meganuclease as defined above; said polynucleotide may encode one monomer of a homodimeric or heterodimeric variant, or two domains/monomers of a single-chain chimeric meganuclease.

The subject-matter of the present invention is also a recombinant vector for the expression of a variant or a single-chain meganuclease according to the invention. The recombinant vector comprises at least one polynucleotide fragment encoding a variant or a single-chain meganuclease, as defined above. In a preferred embodiment, said vector comprises two different polynucleotide fragments, each encoding one of the monomers of a heterodimeric variant.

A vector which can be used in the present invention includes, but is not limited to, a viral vector, a plasmid, a RNA vector or a linear or circular DNA or RNA molecule which may consists of a chromosomal, non chromosomal, semi-synthetic or synthetic nucleic acids. Preferred vectors are those capable of autonomous replication (episomal vector) and/or expression of nucleic acids to which they are linked (expression vectors). Large numbers of suitable vectors are known to those of skill in the art and commercially available.

Viral vectors include retrovirus, adenovirus, parvovirus (e.g. adeno-associated viruses), coronavirus, negative strand RNA viruses such as orthomyxovirus (e.g., influenza virus), rhabdovirus (e.g., rabies and vesicular stomatitis virus), paramyxovirus (e.g. measles and Sendai), positive strand RNA viruses such as picornavirus and alphavirus, and double-stranded DNA viruses including adenovirus, herpesvirus (e.g., Herpes Simplex virus types 1 and 2, Epstein-Barr virus, cytomegalovirus), and poxvirus (e.g., vaccinia, fowlpox and canarypox). Other viruses include Norwalk virus, togavirus, flavivirus, reoviruses, papovavirus, hepadnavirus, and hepatitis virus, for example. Examples of retroviruses include: avian leukosis-sarcoma, mammalian C-type, B-type viruses, D type viruses, HTLV-BLV group, lentivirus, spumavirus (Coffin, J. M., Retroviridae: The viruses and their replication, In Fundamental Virology, Third Edition, B. N. Fields, et al., Eds., Lippincott-Raven Publishers, Philadelphia, 1996).

Preferred vectors include lentiviral vectors, and particularly self inactivating lentiviral vectors.

Vectors can comprise selectable markers, for example: neomycin phosphotransferase, histidinol dehydrogenase, dihydrofolate reductase, hygromycin phosphotransferase, herpes simplex virus thymidine kinase, adenosine deaminase, glutamine synthetase, and hypoxanthine-guanine phosphoribosyl transferase for eukaryotic cell culture; TRP1 for *S. cerevisiae*; tetracycline, rifampicin or ampicillin resistance in *E. coli*.

Preferably said vectors are expression vectors, wherein the sequence(s) encoding the variant/single-chain meganuclease of the invention is placed under control of appropriate transcriptional and translational control elements to permit production or synthesis of said variant. Therefore, said polynucleotide is comprised in an expression cassette. More particularly, the vector comprises a replication origin, a promoter operatively linked to said encoding polynucleotide, a ribosome-binding site, an RNA-splicing site (when genomic DNA is used), a polyadenylation site and a transcription termination site. It also can comprise an enhancer. Selection of the promoter will depend upon the cell in which the polypeptide is expressed. Preferably, when said variant is a heterodimer, the two polynucleotides encoding each of the monomers are included in one vector which is able to drive the expression of both polynucleotides, simultaneously. Suitable promoters include tissue specific and/or inducible promoters. Examples of inducible promoters are: eukaryotic metallothionine promoter which is induced by increased levels of heavy metals, prokaryotic lacZ promoter which is induced in response to isopropyl-β-D-thiogalacto-pyranoside (IPTG) and eukaryotic heat shock promoter which is induced by increased temperature. Examples of tissue specific promoters are skeletal muscle creatine kinase, prostate-specific antigen (PSA), α-antitrypsin protease, human surfactant (SP) A and B proteins, β-casein and acidic whey protein genes.

According to another advantageous embodiment of said vector, it includes a targeting construct comprising sequences sharing homologies with the region surrounding the genomic DNA cleavage site as defined above.

Alternatively, the vector coding for an I-CreI variant/single-chain meganuclease and the vector comprising the targeting construct are different vectors.

More preferably, the targeting DNA construct comprises:
 a) sequences sharing homologies with the region surrounding the genomic DNA cleavage site as defined above, and
 b) a sequence to be introduced flanked by sequences as in a).

For gene knock-in at the mouse the ROSA26 locus, the sequence to be introduced comprises an exogenous gene expression cassette or part thereof and eventually a selection marker, such as the HPRT gene.

Alternatively, the sequence to be introduced can be any other sequence used to alter the mouse ROSA26 locus in some specific way including a sequence used to modify a specific sequence in the mouse ROSA26 locus, to attenuate or activate the mouse ROSA26 locus or part thereof, to introduce a mutation into a site of interest of the mouse ROSA26 locus, or to inactivate or delete the mouse ROSA26 locus or a part thereof.

Preferably, homologous sequences of at least 50 bp, preferably more than 100 bp and more preferably more than 200 bp are used for repairing the cleavage site. Indeed, shared DNA homologies are located in regions flanking upstream and downstream the site of the break and the DNA sequence to be introduced should be located between the two arms.

Therefore, the targeting construct is preferably from 200 pb to 6000 pb, more preferably from 1000 pb to 2000 pb.

For the insertion of a sequence, DNA homologies are generally located in regions directly upstream and downstream to the site of the break (sequences immediately adjacent to the break; minimal repair matrix). However, when the insertion is associated with a deletion of sequences flanking the cleavage site, shared DNA homologies are located in regions upstream and downstream the region of the deletion.

For example, the mouse ROSA 26 DNA targets which are cleaved by the variants as defined above and the minimal matrix for repairing each of the cleavage generated by each variant, are indicated in FIG. 17.

The subject-matter of the present invention is also a composition characterized in that it comprises at least one meganuclease as defined above (variant or single-chain derived chimeric meganuclease) and/or at least one expression vector encoding said meganuclease, as defined above.

In a preferred embodiment of said composition, it comprises a targeting DNA construct as defined above.

Preferably, said targeting DNA construct is either included in a recombinant vector or it is included in an expression vector comprising the polynucleotide(s) encoding the meganuclease according to the invention.

The subject-matter of the present invention is further the use of a meganuclease as defined above, one or two polynucleotide(s), preferably included in expression vector(s), for genome engineering at the mouse ROSA26 locus, for non-therapeutic purposes.

According to an advantageous embodiment of said use, it is for inducing a double-strand break in a site of interest of the mouse ROSA26 locus comprising a genomic DNA target sequence, thereby inducing a DNA recombination event, a DNA loss or cell death.

According to the invention, said double-strand break is for: modifying a specific sequence in the ROSA26 locus, attenuating or activating the endogenous ROSA26 locus, introducing a mutation into a site of interest of the ROSA26 locus, introducing an exogenous gene or a part thereof, inactivating or deleting the endogenous ROSA26 locus or a part thereof, translocating a chromosomal arm, or leaving the DNA unrepaired and degraded.

According to another advantageous embodiment of said use, said variant, polynucleotide(s), vector, are associated with a targeting DNA construct as defined above.

In a preferred embodiment of the use of the meganuclease according to the present invention, it comprises at least the following steps: 1) introducing a double-strand break at a site of interest of the mouse ROSA26 locus comprising at least one recognition and cleavage site of said meganuclease, by contacting said cleavage site with said meganuclease; 2) providing a targeting DNA construct comprising the sequence to be introduced flanked by sequences sharing homologies to the targeted locus. Said meganuclease can be provided directly to the cell or through an expression vector comprising the polynucleotide sequence encoding said meganuclease and suitable for its expression in the used cell. This strategy is used to introduce a DNA sequence at the target site, for example to generate knock-in transgenic mice or recombinant mouse cell lines that can be used for protein production, gene function studies, drug development (drug screening) or as disease model.

The subject-matter of the present invention is also a method for making a transgenic mouse expressing a product of interest, comprising at least the step of (a) introducing into a mouse pluripotent precursor cell or a mouse embryo, a meganuclease, as defined above, so as to into induce a double stranded cleavage at a site of interest of the ROSA26 locus comprising a DNA recognition and cleavage site of said meganuclease; simultaneously or consecutively, (b) introducing into the mouse precursor cell or embryo of step (a) a targeting DNA, comprising at least a sequence encoding a product of interest flanked by sequences sharing homologies to the region surrounding the cleavage site, so as to generate a genomically modified mouse precursor cell or embryo having inserted the sequence of interest by homologous recombination between the targeting DNA and the chromosomal DNA, (c) developing the genomically modified mouse precursor cell or embryo of step (b) into a chimeric mouse, and (d) deriving a transgenic mouse from the chimeric mouse of step (c).

Preferably, step (c) comprises the introduction of the genomically modified precursor cell generated in step (b) into blastocysts so as to generate chimeric mice.

According to a preferred embodiment of said method, it comprises a further step (e) of recovering the product of interest from the transgenic mouse, by any means.

The subject-matter of the present invention is also a method for making a recombinant mouse cell expressing a product of interest, comprising at least the step of:

(a) introducing into a mouse cell, a meganuclease, as defined above, so as to into induce a double stranded cleavage at a site of interest of the ROSA26 locus comprising a DNA recognition and cleavage site for said meganuclease, simultaneously or consecutively, (b) introducing into the cell of step (a), a targeting DNA, wherein said targeting DNA comprising at least a sequence encoding a product of interest flanked by sequences sharing homologies to the region surrounding the cleavage site, so as to generate a recombinant mouse cell having inserted the sequence of interest by homologous recombination between the targeting DNA and the chromosomal DNA, (c) isolating the recombinant mouse cell of step (b), by any appropriate mean.

According to a preferred embodiment of said method, it comprises a further step (d) of recovering the product of interest from the recombinant mouse cell, by any means.

The targeting DNA is introduced into the cell under conditions appropriate for introduction of the targeting DNA into the site of interest.

In a preferred embodiment, said targeting DNA construct is inserted in a vector.

The cell which is modified may be any cell of interest. For making transgenic mice, the cells are pluripotent precursor cells such as embryo-derived stem (ES) cells, which are well-known in the art. For making recombinant mouse cell lines, the cells may advantageously be NSO, SP2/0 (BALB/c myeloma; ECACC # 85110503 and # 85072401), or L (ATCC # CRL-2648) cells. Said meganuclease can be provided directly to the cell or through an expression vector comprising the polynucleotide sequence encoding said meganuclease and suitable for its expression in the used cell.

For making transgenic animals/recombinant cell lines expressing a product of interest, the targeting DNA comprises a sequence encoding the product of interest (protein or RNA), and eventually a selectable marker gene, flanked by sequences upstream and downstream the meganuclease site in the mouse ROSA26 locus, as defined above, so as to generate genomically modified cells (animal precursor cell or embryo/animal or human cell) having integrated the exogenous sequence of interest at the meganuclease site in the ROSA26 locus, by homologous recombination.

The sequence of interest may be any gene coding for a certain protein/peptide of interest, included but not limited to: reporter genes, receptors, signaling molecules, transcription factors, pharmaceutically active proteins and peptides, disease causing gene products and toxins. The sequence may also encode an RNA molecule of interest including for example a siRNA.

The expression of the exogenous sequence may be driven, either by the endogenous ROSA26 promoter or by an heterologous promoter, preferably a ubiquitous or tissue specific promoter, either constitutive or inducible, as defined above. In addition, the expression of the sequence of interest may be conditional; the expression may be induced by a site-specific recombinase (Cre, FLP . . . ).

Thus, the sequence of interest is inserted in an appropriate cassette that may comprise an heterologous promoter operatively linked to said gene of interest and one or more functional sequences including but mot limited to (selectable) marker genes, recombinase recognition sites, polyadenylation signals, splice acceptor sequences, introns, tags for protein detection and enhancers.

Alternatively, the appropriate cassette may comprise an Internal Ribosomal Entry site (IRES) operatively linked to said gene of interest and one or more functional sequences including but n events with the IRES-Hygro matrix (pCLS1675).ot limited to (selectable) marker genes, recombinase recognition sites, polyadenylation signals, splice acceptor sequences, introns, tags for protein detection and enhancers.

The meganuclease can be used either as a polypeptide or as a polynucleotide construct encoding said polypeptide. It is introduced into mouse cells, by any convenient means well-known to those in the art, which are appropriate for the particular cell type, alone or in association with either at least an appropriate vehicle or carrier and/or with the targeting DNA.

According to an advantageous embodiment of the uses according to the invention, the meganuclease (polypeptide) is associated with:
- liposomes, polyethyleneimine (PEI); in such a case said association is administered and therefore introduced into somatic target cells.
- membrane translocating peptides (Bonetta, The Scientist, 2002, 16, 38; Ford et al., Gene Ther., 2001, 8, 1-4; Wadia and Dowdy, Curr. Opin. Biotechnol., 2002, 13, 52-56); in such a case, the sequence of the variant/single-chain meganuclease is fused with the sequence of a membrane translocating peptide (fusion protein).

According to another advantageous embodiment of the uses according to the invention, the meganuclease (polynucleotide encoding said meganuclease) and/or the targeting DNA is inserted in a vector. Vectors comprising targeting DNA and/or nucleic acid encoding a meganuclease can be introduced into a cell by a variety of methods (e.g., injection, direct uptake, projectile bombardment, liposomes, electroporation). Meganucleases can be stably or transiently expressed into cells using expression vectors. Techniques of expression in eukaryotic cells are well known to those in the art. (See Current Protocols in Human Genetics: Chapter 12 "Vectors For Gene Therapy" & Chapter 13 "Delivery Systems for Gene Therapy"). Optionally, it may be preferable to incorporate a nuclear localization signal into the recombinant protein to be sure that it is expressed within the nucleus.

Once in a cell, the meganuclease and if present, the vector comprising targeting DNA and/or nucleic acid encoding a meganuclease are imported or translocated by the cell from the cytoplasm to the site of action in the nucleus.

In one embodiment of the uses according to the present invention, the meganuclease is substantially non-immunogenic, i.e., engender little or no adverse immunological response. A variety of methods for ameliorating or eliminating deleterious immunological reactions of this sort can be used in accordance with the invention. In a preferred embodiment, the meganuclease is substantially free of N-formyl methionine. Another way to avoid unwanted immunological reactions is to conjugate meganucleases to polyethylene glycol ("PEG") or polypropylene glycol ("PPG") (preferably of 500 to 20,000 daltons average molecular weight (MW)). Conjugation with PEG or PPG, as described by Davis et al. (U.S. Pat. No. 4,179,337) for example, can provide non-immunogenic, physiologically active, water soluble endonuclease conjugates with anti-viral activity. Similar methods also using a polyethylene-polypropylene glycol copolymer are described in Saifer et al. (U.S. Pat. No. 5,006,333).

The invention also concerns a prokaryotic or eukaryotic host cell which is modified by a polynucleotide or a vector as defined above, preferably an expression vector.

The invention also concerns a non-human transgenic animal or a transgenic plant, characterized in that all or parts of their cells are modified by a polynucleotide or a vector as defined above.

As used herein, a cell refers to a prokaryotic cell, such as a bacterial cell, or an eukaryotic cell, such as an animal, plant or yeast cell.

The subject-matter of the present invention is also the use of at least one meganuclease variant, as defined above, as a scaffold for making other meganucleases. For example a third round of mutagenesis and selection/screening can be performed on said variants, for the purpose of making novel, third generation meganucleases.

The different uses of the meganuclease and the methods of using said meganuclease according to the present invention include the use of the I-CreI variant, the single-chain chimeric meganuclease derived from said variant, the polynucleotide(s), vector, cell, transgenic plant or non-human transgenic mammal encoding said variant or single-chain chimeric meganuclease, as defined above.

The I-CreI variant according to the invention may be obtained by a method for engineering I-CreI variants able to cleave a genomic DNA target sequence from the mouse ROSA26 locus, comprising at least the steps of:

(a) constructing a first series of I-CreI variants having at least one substitution in a first functional subdomain of the LAGLIDADG (SEQ ID NO: 150) core domain situated from positions 26 to 40 of I-CreI, (b) constructing a second series of I-CreI variants having at least one substitution in a second functional subdomain of the LAGLIDADG (SEQ ID NO: 150) core domain situated from positions 44 to 77 of I-CreI, (c) selecting and/or screening the variants from the first series of step (a) which are able to cleave a mutant I-CreI site wherein at least (i) the nucleotide triplet at positions −10 to −8 of the I-CreI site has been replaced with the nucleotide triplet which is present at positions −10 to −8 of said genomic target and (ii) the nucleotide triplet at positions +8 to +10 has been replaced with the reverse complementary sequence of the nucleotide triplet which is present at positions −10 to −8 of said genomic target, (d) selecting and/or screening the variants from the second series of step (b) which are able to cleave a mutant I-CreI site wherein at least (i) the nucleotide triplet at positions −5 to −3 of the I-CreI site has been replaced with the nucleotide triplet which is present at positions −5 to −3 of said genomic target and (ii) the nucleotide triplet at positions +3 to +5 has been replaced with the reverse complementary sequence of the nucleotide triplet which is present at positions −5 to −3 of said genomic target, (e) selecting and/or screening the variants from the first series of step (a) which are able to cleave a mutant I-CreI site wherein at least (i) the nucleotide triplet at positions +8 to +10 of the I-CreI site has been replaced with the nucleotide triplet which is present at positions +8 to +10 of said genomic target and (ii) the nucleotide triplet at positions −10 to −8 has been replaced with the reverse complementary sequence of the nucleotide triplet which is present at positions +8 to +10 of said genomic target, (f) selecting and/or screening the variants from the second series of step (b) which are able to cleave a mutant I-CreI site wherein at least (i) the nucleotide triplet at positions +3 to +5 of the I-CreI site has been replaced with the nucleotide triplet which is present at positions +3 to +5 of said genomic target and (ii) the nucleotide triplet at positions −5 to −3 has been replaced with the reverse complementary sequence of the nucleotide triplet which is present at positions +3 to +5 of said genomic target, (g) combining in a single variant, the mutation(s) at positions 26 to 40 and 44 to 77 of two variants from step (c) and step (d), to obtain a novel homodimeric I-CreI variant which cleaves a sequence wherein (i) the nucleotide triplet at positions −10 to −8 is identical to the nucleotide triplet which is present at positions −10 to −8 of said genomic target, (ii) the nucleotide triplet at positions +8 to +10 is identical to the reverse complementary sequence of the nucleotide triplet which is present at positions −10 to −8 of said genomic target, (iii) the nucleotide triplet at positions −5 to −3 is identical to the nucleotide triplet which is present at positions −5 to −3 of said genomic target and (iv) the nucleotide triplet at positions +3 to +5 is identical to the reverse complementary sequence of the nucleotide triplet which is present at positions −5 to −3 of said genomic target, and/or (h) combining in a single variant, the mutation(s) at positions 26 to 40 and 44 to 77 of two variants from step (e) and step (f), to obtain a novel homodimeric I-CreI variant which cleaves a sequence wherein (i) the nucleotide triplet at positions +3 to +5 is identical to the nucleotide triplet which is present at positions +3 to +5 of said genomic target, (ii) the nucleotide triplet at positions −5 to −3 is identical to the reverse complementary sequence of the nucleotide triplet which is present at positions +3 to +5 of said genomic target, (iii) the nucleotide triplet at positions +8 to +10 of the I-CreI site has been replaced with the nucleotide triplet which is present at positions +8 to +10 of said genomic target and (iv) the nucleotide triplet at positions −10 to −8 is identical to the reverse complementary sequence of the nucleotide triplet at positions +8 to +10 of said genomic target, (i) combining the variants obtained in steps (g) and (h) to form heterodimers, and (j) selecting and/or screening the heterodimers from step (i) which are able to cleave said genomic DNA target from the mouse ROSA26 locus.

One of the step(s) (c), (d), (e) or (f) may be omitted. For example, if step (c) is omitted, step (d) is performed with a mutant I-CreI site wherein both nucleotide triplets at positions −10 to −8 and −5 to −3 have been replaced with the nucleotide triplets which are present at positions −10 to −8 and −5 to −3, respectively of said genomic target, and the nucleotide triplets at positions +3 to +5 and +8 to +10 have been replaced with the reverse complementary sequence of the nucleotide triplets which are present at positions −5 to −3 and −10 to −8, respectively of said genomic target.

Steps (a), (b), (g), (h) and (i) may further comprise the introduction of additional mutations at other positions contacting the DNA target sequence or interacting directly or indirectly with said DNA target, at positions which improve the binding and/or cleavage properties of the mutants, or at positions which prevent the formation of functional homodimers, as defined above. This may be performed by generating a combinatorial library as described in the International PCT Application WO 2004/067736.

The method for engineering I-CreI variants of the invention advantageously comprise the introduction of random mutations on the whole variant or in a part of the variant, in particular the C-terminal half of the variant (positions 80 to 163) to improve the binding and/or cleavage properties of the mutants towards the DNA target from the gene of interest. The mutagenesis may be performed by generating random mutagenesis libraries on a pool of variants, according to standard mutagenesis methods which are well-known in the art and commercially available. Preferably, the mutagenesis is performed on the entire sequence of one monomer of the heterodimer formed in step (i) or obtained in step (j), advantageously on a pool of monomers, preferably on both monomers of the heterodimer of step (i) or (j).

Preferably, two rounds of selection/screening are performed according to the process illustrated by FIG. 4 of Arnould et al., J. Mol. Biol., Epub 10 May 2007. In the first round, one of the monomers of the heterodimer is mutagenised (monomer Y in FIG. 4), co-expressed with the other monomer (monomer X in FIG. 4) to form heterodimers, and the improved monomers $Y^+$ are selected against the target from the gene of interest. In the second round, the other monomer (monomer X) is mutagenised, co-expressed with the improved monomers $Y^+$ to form heterodimers, and selected against the target from the gene of interest to obtain meganucleases ($X^+ Y^+$) with improved activity.

The (intramolecular) combination of mutations in steps (g) and (h) may be performed by amplifying overlapping fragments comprising each of the two subdomains, according to well-known overlapping PCR techniques.

The (intermolecular) combination of the variants in step (i) is performed by co-expressing one variant from step (g) with one variant from step (h), so as to allow the formation of heterodimers. For example, host cells may be modified by one or two recombinant expression vector(s) encoding said variant(s). The cells are then cultured under conditions allowing the expression of the variant(s), so that heterodimers are formed in the host cells, as described previously in the International PCT Application WO 2006/097854 and Arnould et al., J. Mol. Biol., 2006, 355, 443-458.

The selection and/or screening in steps (c), (d), (e), (f) and/or (j) may be performed by using a cleavage assay in vitro or in vivo, as described in the International PCT Application WO 2004/067736, Arnould et al., J. Mol. Biol., 2006, 355, 443-458, Epinat et al., Nucleic Acids Res., 2003, 31, 2952-2962 and Chames et al., Nucleic Acids Res., 2005, 33, e178.

According to another advantageous embodiment of said method, steps (c), (d), (e), (f) and/or (j) are performed in vivo, under conditions where the double-strand break in the mutated DNA target sequence which is generated by said variant leads to the activation of a positive selection marker or a reporter gene, or the inactivation of a negative selection marker or a reporter gene, by recombination-mediated repair of said DNA double-strand break.

The subject matter of the present invention is also an I-CreI variant having mutations at positions 26 to 40 and/or 44 to 77 of I-CreI that is useful for engineering the variants able to cleave a DNA target from the mouse ROSA26 locus, according to the present invention. In particular, the invention encompasses the I-CreI variants as defined in step (c) to (f) of the method for engineering I-CreI variants, as defined above, including the variants m1 to m18 (Table II, SEQ ID NO: 38 to 55), the variant comprising Q44V, R70A and D75N (SEQ ID NO: 131; Table III) and the variant comprising K28E, Y33R, Q38R, S40R and D75N (SEQ ID NO: 132; Table III). The invention encompasses also the I-CreI variants as defined in step (g) and (h) of the method for engineering I-CreI variants, as defined above, including the variants of the sequence SEQ ID NO:60 to 67 (combined variants of Table III).

Single-chain chimeric meganucleases able to cleave a DNA target from the gene of interest are derived from the variants according to the invention by methods well-known in the art (Epinat et al., Nucleic Acids Res., 2003, 31, 2952-62; Chevalier et al., Mol. Cell., 2002, 10, 895-905; Steuer et al., Chembiochem., 2004, 5, 206-13; International PCT Applications WO 03/078619 and WO 2004/031346). Any of such methods, may be applied for constructing single-chain chimeric meganucleases derived from the variants as defined in the present invention.

The polynucleotide sequence(s) encoding the variant as defined in the present invention may be prepared by any method known by the man skilled in the art. For example, they are amplified from a cDNA template, by polymerase chain reaction with specific primers. Preferably the codons of said cDNA are chosen to favour the expression of said protein in the desired expression system.

The recombinant vector comprising said polynucleotides may be obtained and introduced in a host cell by the well-known recombinant DNA and genetic engineering techniques.

The I-CreI variant or single-chain derivative as defined in the present the invention are produced by expressing the polypeptide(s) as defined above; preferably said polypeptide(s) are expressed or co-expressed (in the case of the variant only) in a host cell or a transgenic animal/plant modified by one expression vector or two expression vectors (in the case of the variant only), under conditions suitable for the expression or co-expression of the polypeptide(s), and the variant or single-chain derivative is recovered from the host cell culture or from the transgenic animal/plant.

The practice of the present invention will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, Current Protocols in Molecular Biology (Frederick M. AUSUBEL, 2000, Wiley and son Inc, Library of Congress, USA); Molecular Cloning: A Laboratory Manual, Third Edition, (Sambrook et al, 2001, Cold Spring Harbor, N.Y.: Cold Spring Harbor Laboratory Press); Oligonucleotide Synthesis (M. J. Gait ed., 1984); Mullis et al. U.S. Pat. No. 4,683,195; Nucleic Acid Hybridization (B. D. Harries & S. J. Higgins eds. 1984); Transcription And Translation (B. D. Hames & S. J. Higgins eds. 1984); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the series, Methods In ENZYMOLOGY (J. Abelson and M. Simon, eds.-in-chief, Academic Press, Inc., New York), specifically, Vols. 154 and 155 (Wu et al. eds.) and Vol. 185, "Gene Expression Technology" (D. Goeddel, ed.); Gene Transfer Vectors For Mammalian Cells (J. H. Miller and M. P. Calos eds., 1987, Cold Spring Harbor Laboratory); Immunochemical Methods In Cell And Molecular Biology (Mayer and Walker, eds., Academic Press, London, 1987); Handbook Of Experimental Immunology, Volumes I-IV (D. M. Weir and C. C. Blackwell, eds., 1986); and Manipulating the Mouse Embryo, (Cold Spring Harbor Laboratory Press, Cold Spring Harbor, N.Y., 1986).

In addition to the preceding features, the invention further comprises other features which will emerge from the description which follows, which refers to examples illustrating the I-CreI meganuclease variants and their uses according to the invention, as well as to the appended drawings in which:

FIG. 1 represents the mouse ROSA26 locus (accession number EMBL CQ880114; SEQ ID NO: 3). The Exons are boxed (Exon 1: positions 2490 to 2599; Exon 2 from transcript 1: positions 8228 to 9248; Exon 3 from transcript 2 starts at position 11845, and largely overlaps with the antisense transcript, which ends art position 11505. The three transcripts identified so far are indicated as well as the sequence and position of target rosa1 (SEQ ID NO: 15).

FIG. 2 represents the tridimensional structure of the I-CreI homing endonuclease bound to its DNA target. The catalytic core is surrounded by two αββαββα folds forming a saddle-shaped interaction interface above the DNA major groove.

FIG. 3 illustrates a two-step approach to engineer the specificity of I-CreI and other LAGLIDADG (SEQ ID NO: 150) homing endonucleases. A large collection of I-CreI derivatives is generated by semi-rational mutagenesis of an initial scaffold and screening for functional variants with locally altered specificity. Then, a combinatorial approach is used to assemble these mutants into meganucleases with fully redesigned specificity. Homodimeric proteins ("half-meganucleases") are created by combinations of two sets of mutations within a same αββαββα fold, and the co-expression of two such 'half-meganucleases" can result in a heterodimeric species ("custom-meganuclease") cleaving the target of interest.

FIG. 4 represents a strategy for the use of a meganuclease cleaving the mouse ROSA26 locus. Gene insertion using meganuclease-induced homologous recombination will knock-in a gene of interest in the mouse ROSA26 locus. Introns and exons sequences can be used as homologous regions.

FIG. 5 represents the rosa1 target sequence and derivatives. 10GGG_P, 5GAT_P and 5TAT_P are close derivatives found to be cleaved by previously obtained I-CreI mutants. They differ from C1221 (palindromic sequence cleaved by the I-CreI scaffold protein) by the boxed motives. C1221, 10GGG_P, 5GAT_P and 5TAT_P were first described as 24 bp sequences, but structural data suggest that only the 22 bp are relevant for protein/DNA interaction. However, positions ±12 are indicated in parenthesis. rosa1 is the DNA sequence located in the mouse ROSA26 locus at position 8304. In the rosa1.2 target, the GTTC sequence in the middle of the target is replaced with GTAC, the bases found in C1221. rosa1.3 is the palindromic sequence derived from the left part of rosa1.2, and rosa1.4 is the palindromic sequence derived from the right part of rosa1.2. As shown in the figure, the boxed motives from 10GGG_P, 5GAT_P and 5TAT_P are found in the rosa1 series of targets.

Figure 8:
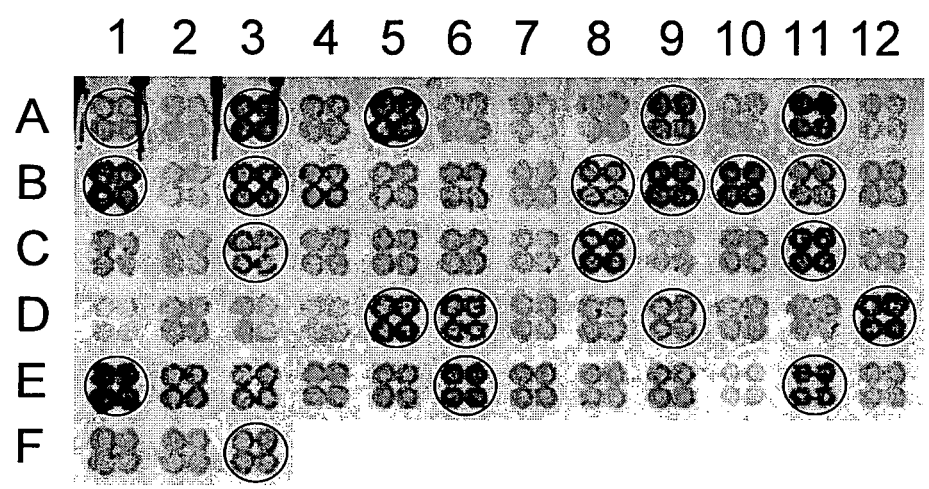

FIG. 8 illustrates the cleavage of the rosa1.3 DNA target by I-CreI mutants. The 63 positives found in primary screen were rearranged in one 96-well plate and validated by a secondary screen (in a quadruplicate format). The 22 mutants chosen in example 2 are circled.

Figure 9:
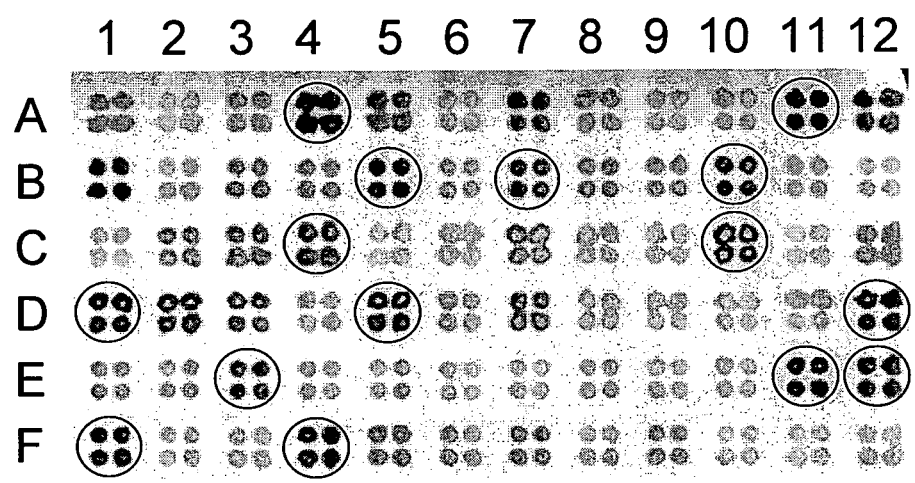

FIG. 9 illustrates the cleavage of the rosa1.4 target by I-CreI combinatorial mutants. The 69 positives found in primary screen were rearranged in one 96-well plate and validated by a secondary screen (in a quadruplicate format). The 15 chosen mutants in example 3 are circled.

Figure 10:
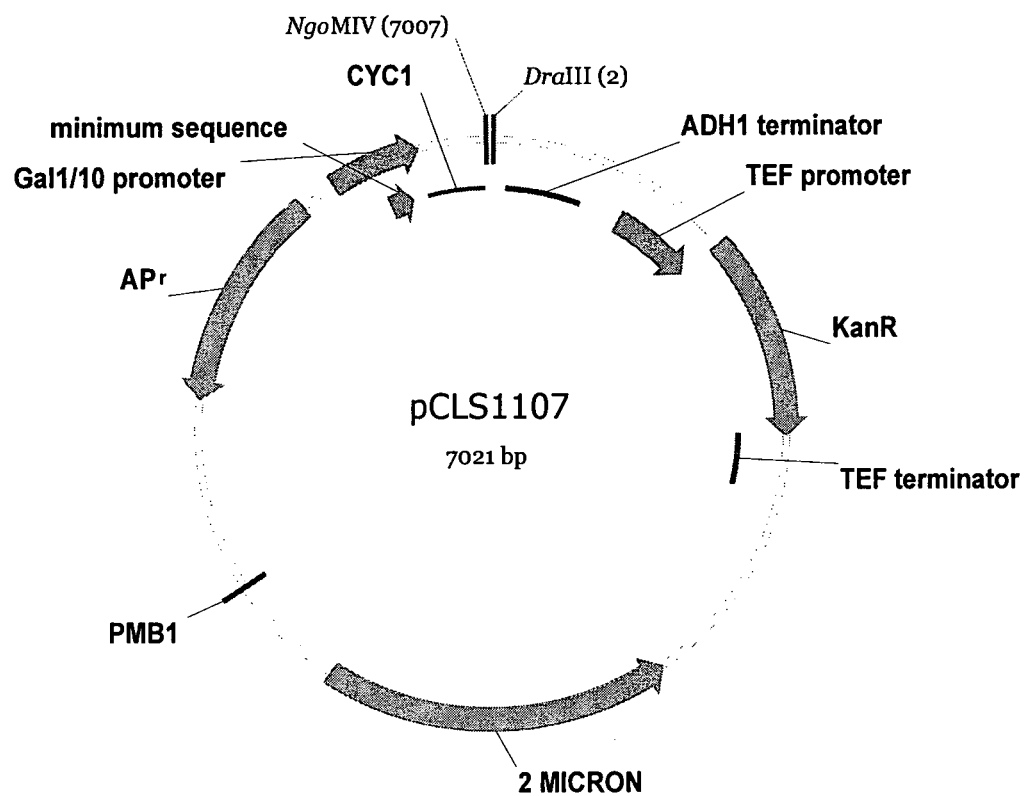

FIG. 10 represents the pCLS1107 vector map.

Figure 11:
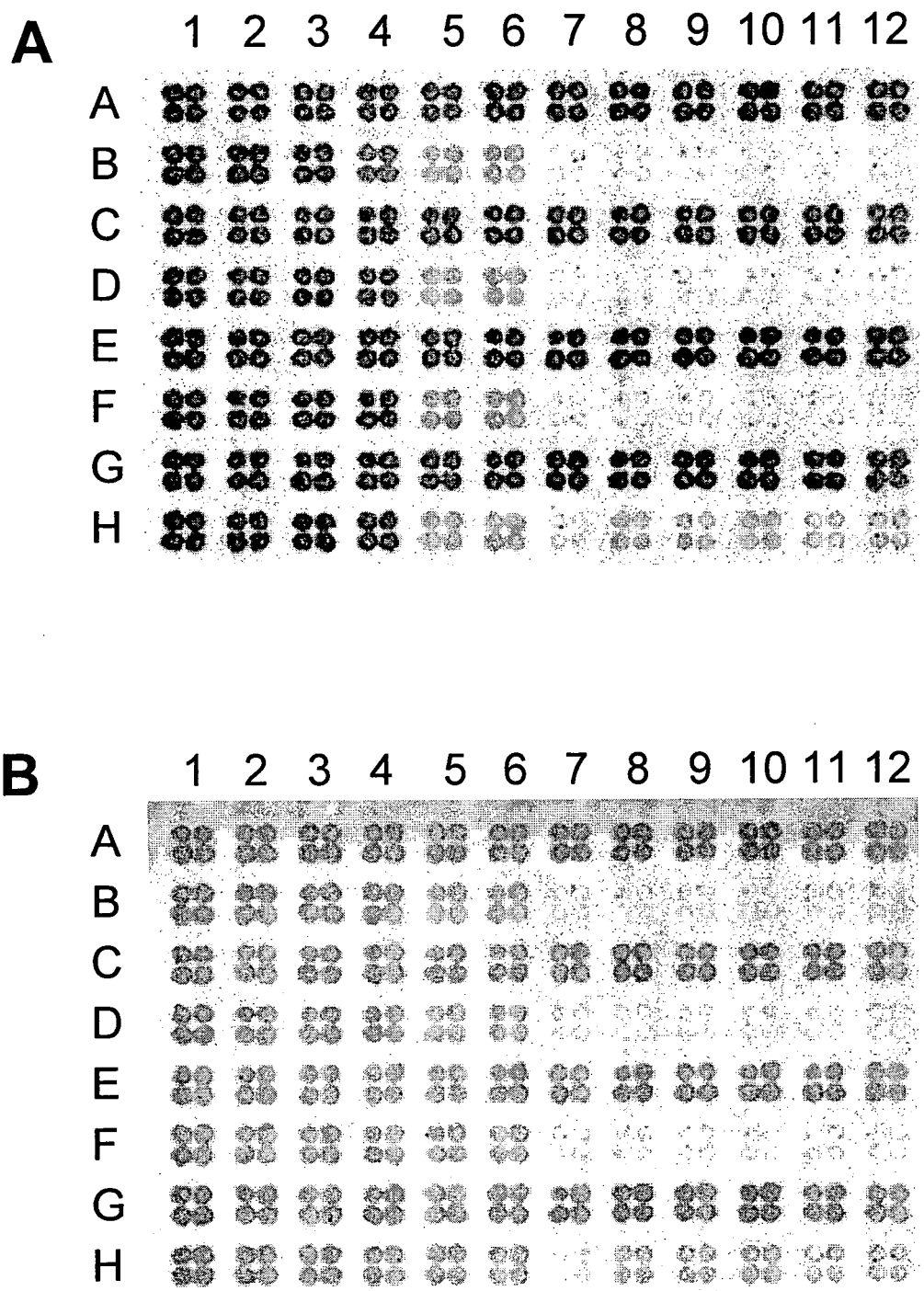

FIG. 11 illustrates the cleavage of the rosa1.2 and rosa1 targets by heterodimeric I-CreI combinatorial mutants. A. Example of screening of combinations of I-CreI mutants with the rosa1.2 target. B. Screening of the same combinations of I-CreI mutants with the rosa1 target. B5, B6, D5, D6, F5, F6, H5 and H6: yeast strains expressing rosa1.3 cutting I-CreI mutants transformed with pCLS1107 empty plasmid DNA.

Figure 12:
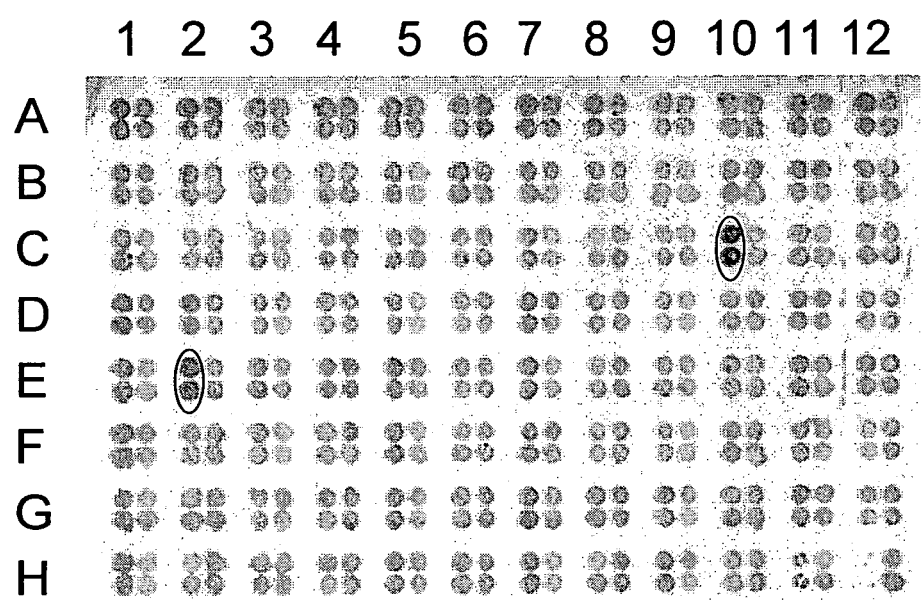

FIG. 12 illustrates the cleavage of the rosa1 target. A series of I-CreI mutants cutting rosa1.4 were randomly mutagenized and co-expressed with a mutant cutting rosa1.3. Cleavage is tested with the rosa1 target. In each four dots cluster, the two dots on the right correspond to one of the original heterodimers cleaving rosa1 in duplicate, whereas the two left dots correspond to a same mutated rosa1.4 cleaver co-expressed with a non mutated rosa1.3 cleaver (mutant m13, described in Tables IV and V). The two optimized mutants displaying improved cleavage of rosa1 are circled, and correspond to co-expression of mutants m13 and MO_1 (C10) or of m13 and MO_2 (E2). MO_1 and MO_2 are further described in Table VI.

Figure 13:
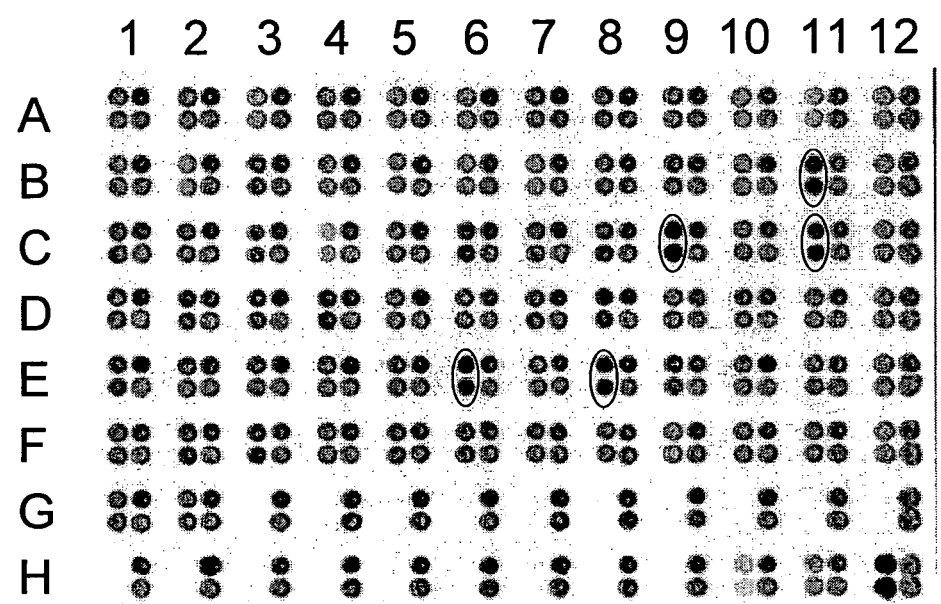

FIG. 13 illustrates the cleavage of the rosa1 target. A series of I-CreI mutants cutting rosa1.3 were randomly mutagenized and co-expressed with a refined mutant cutting rosa1.4. Cleavage is tested with the rosa1 target. Mutants displaying efficient cleavage of rosa1 are circled. In the filter:

B11 corresponds to the heterodimer S19, V24, Y44, R68, S70, N75, V77+E28, R33, R38, K40, A44, H68, Q70, A105, R107, A151, G153, E158;

C9 corresponds to the heterodimer S19, V24, Y44, R68, S70, Q75, I77+E28, R33, R38, K40, A44, H68, Q70, A105, R107, A151, G153, E158;

C11 and E8 correspond to the heterodimer V24, Y44, S68, S70, R75, I77, A105+E28, R33, R38, K40, A44, H68, Q70, A105, R107, A151, G153, E158; and E6 corresponds to the heterodimer V24, Y44, S68, S70, R75, I77, G79+E28, R33, R38, K40, A44, H68, Q70, A105, R107, A151, G153, E158.

H10 is a negative control, H11 and H12 are positive controls of different intensity.

To compare the activity of the heterodimers against the rosa1 target before and after the improvement of mutants cutting the rosa1.3 target: in each cluster, the two right points are one of the heterodimers described in example 5 and the two left points are heterodimers with mutants described in example 6.

Figure 14:
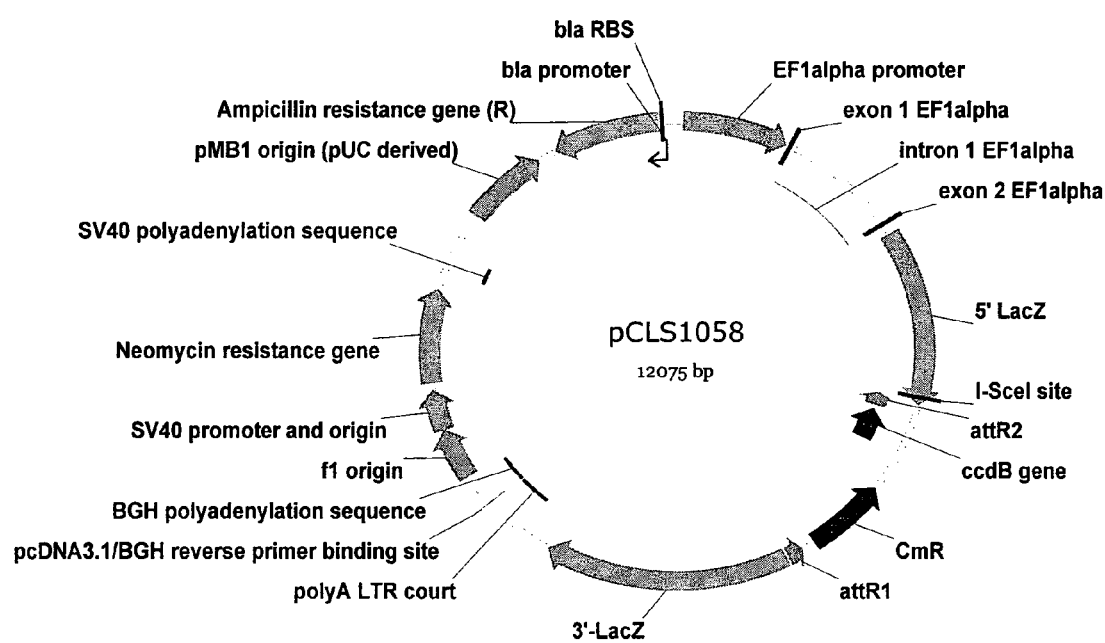

FIG. 14 represents the pCLS1058 vector map.

Figure 15:
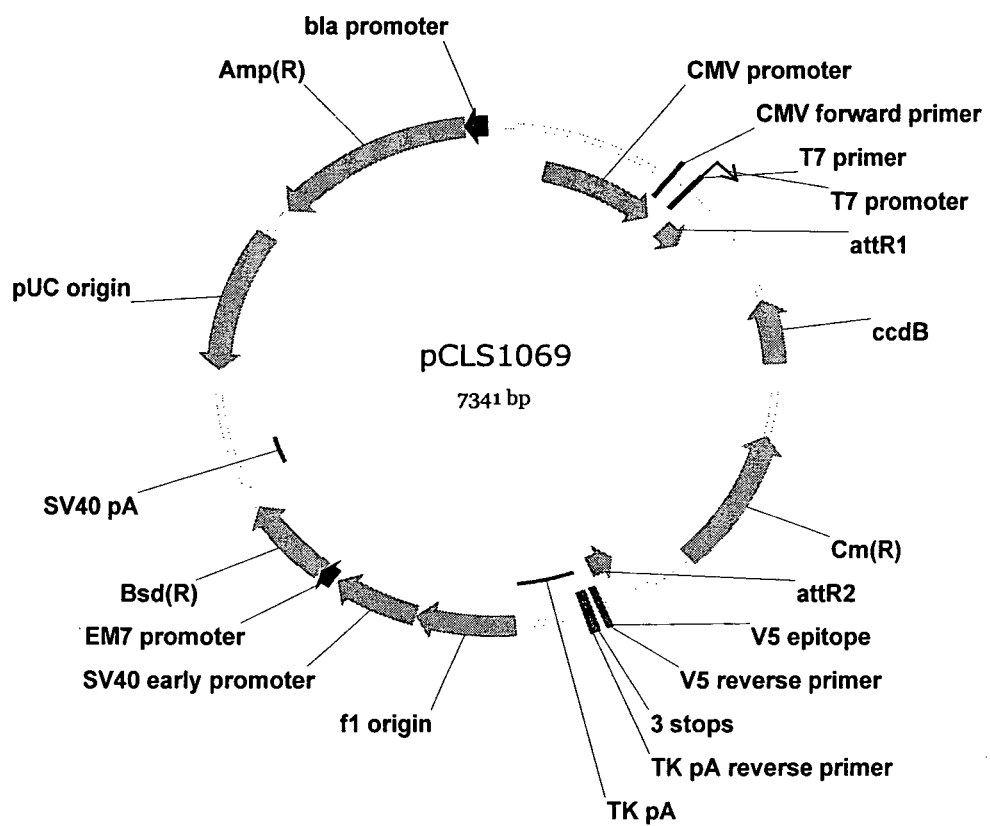

FIG. 15 represents the pCLS1069 vector map.

Figure 16:
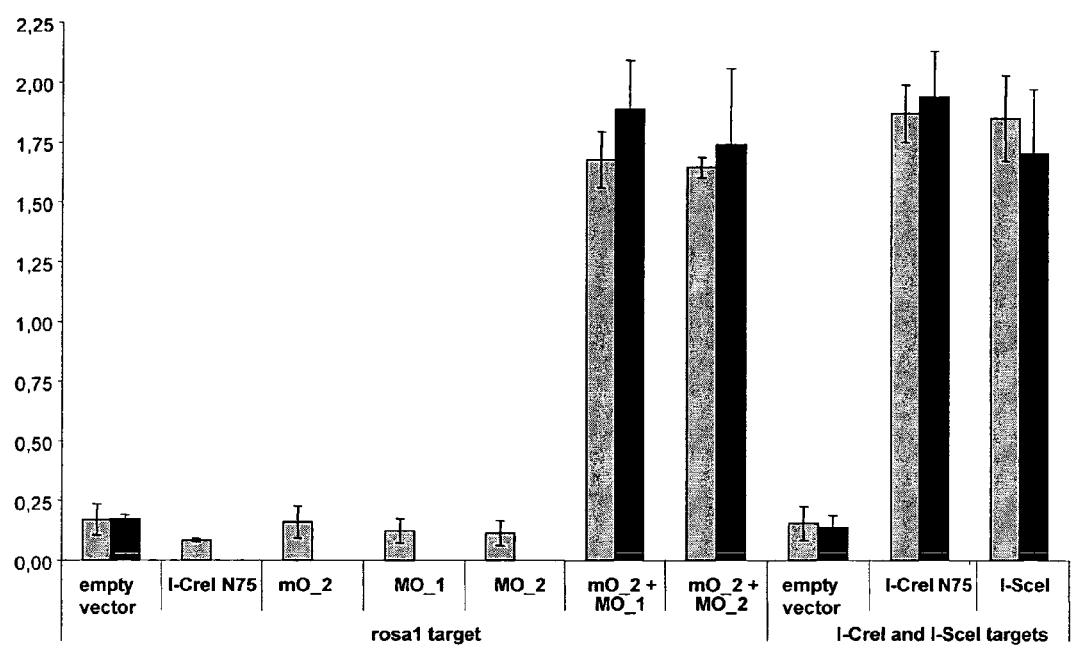

FIG. 16 illustrates the cleavage of the rosa1 target by I-CreI refined mutants in an extrachromosomic model in CHO cells. Values from two transfection experiments are shown. Cleavage of I-CreI and I-SceI targets by I-CreI N75 and I-SceI in the same experiments are shown as positive controls.

FIG. 17 represents meganuclease target sequences found in the mouse ROSA26 and the corresponding I-CreI variant which is able to cleave each of said DNA targets. The sequence of the DNA target is presented (column 1), with its position (column 2). The minimum repair matrix for repairing the cleavage at the target site is indicated by its first nucleotide (start, column 5) and last nucleotide (end, column 6). The sequence of each variant is defined by the residues at the indicated positions. For example, the first heterodimeric variant of FIG. 17 consists of a first monomer having K, H, S, S, Q, S, E, C, S, N and I at positions 28, 30, 32, 33, 38, 40, 44, 68, 70, 75 and 77, respectively and a second monomer having K, D, S, R, T, S, K, E, S, D, R at positions 28, 30, 32, 33, 38, 40, 44, 68, 70, 75 and 77, respectively. The positions are indicated by reference to I-CreI sequence SWISSPROT P05725 (SEQ ID NO: 1); I-CreI has K, N, S, Y, Q, S, Q, R, R, D and I, at positions 28, 30, 32, 33, 38, 40, 44, 68, 70, 75 and 77 respectively.

Figure 18:
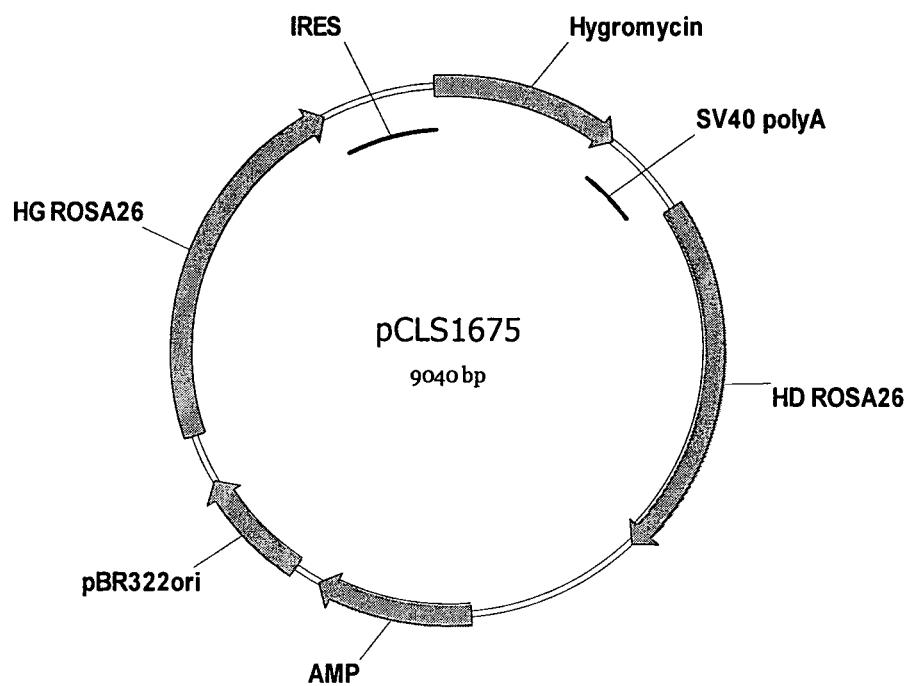

FIG. 18 represents the pCLS1675 vector map.

Figure 19:
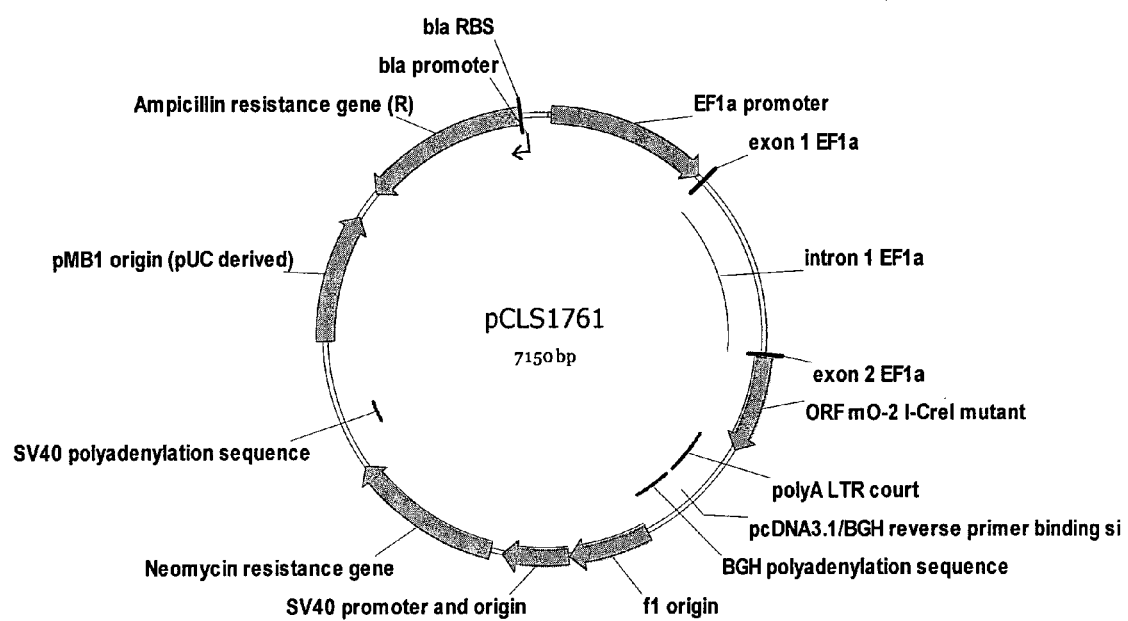

FIG. 19 represents the pCLS1761 vector map.

Figure 20:
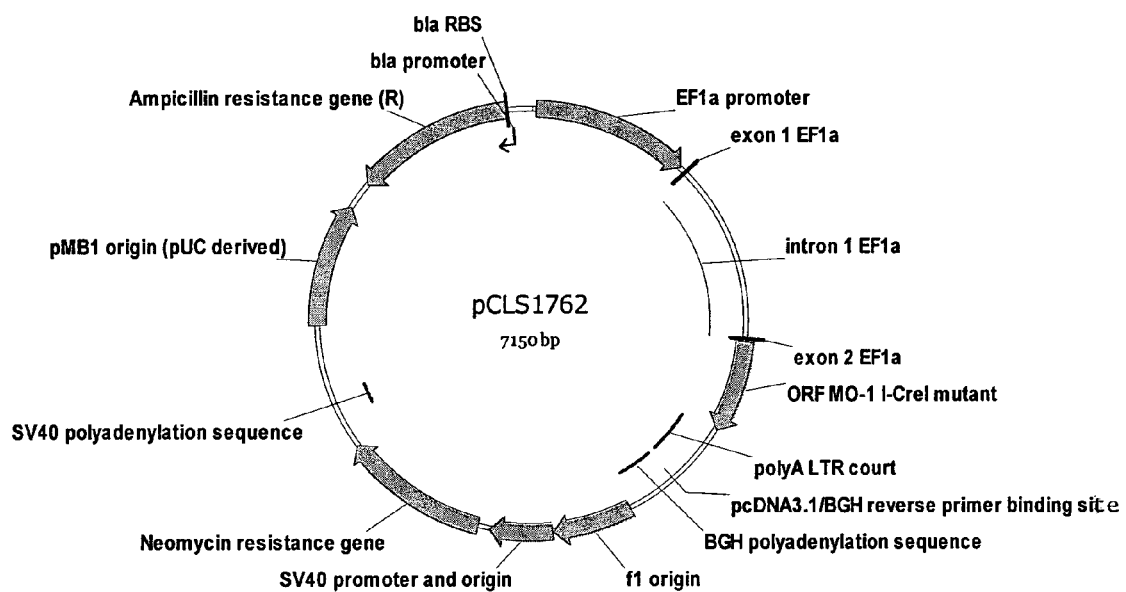

FIG. 20 represents the pCLS1762 vector map.

Figure 21:
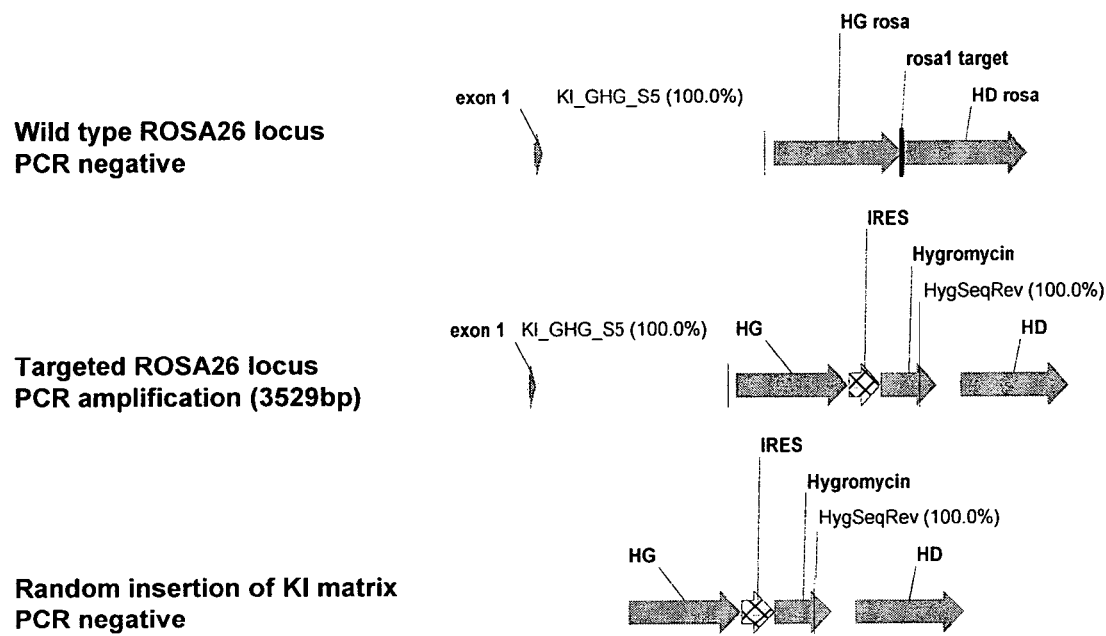

FIG. 21 illustrates PCR analysis of knock-in (KI) events with the IRES-Hygro matrix (pCLS1675). events with the IRES-Hygro matrix (pCLS1675). Clones wild-type for the ROSA26 locus and clones having a random insertion of the hygromycin CDS are negatives in PCR. Clones having a KI event at the ROSA26 locus are positives in PCR. Clones having KI event and random insertion are also positives in PCR.

EXAMPLE 1

Strategy for Engineering Novel Meganucleases Cleaving the Mouse ROSA26 Locus

Figure 1:
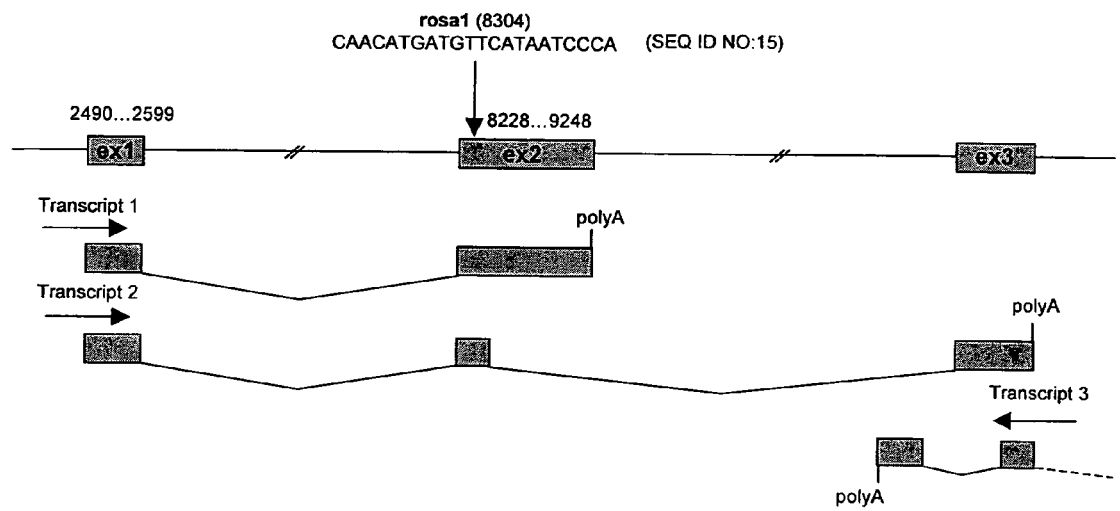
Figure 2:
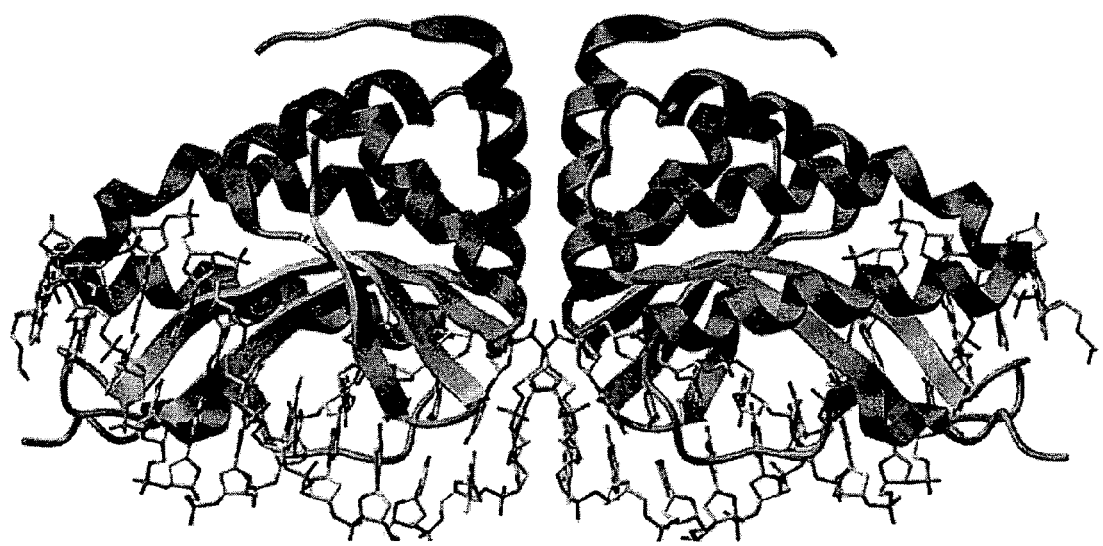
Figure 3:
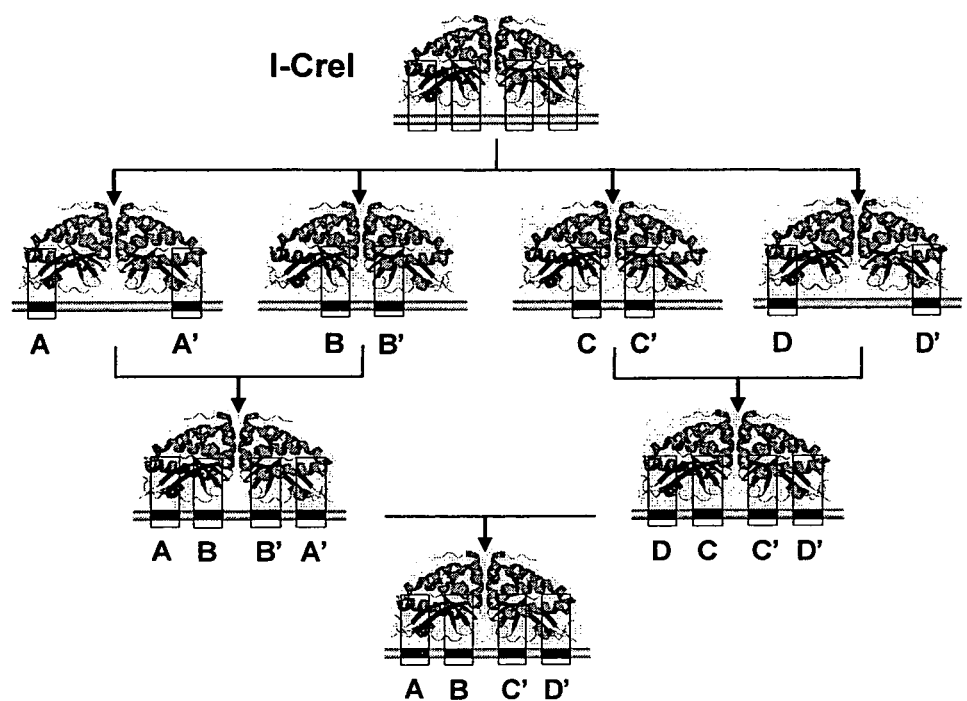
Figure 4:
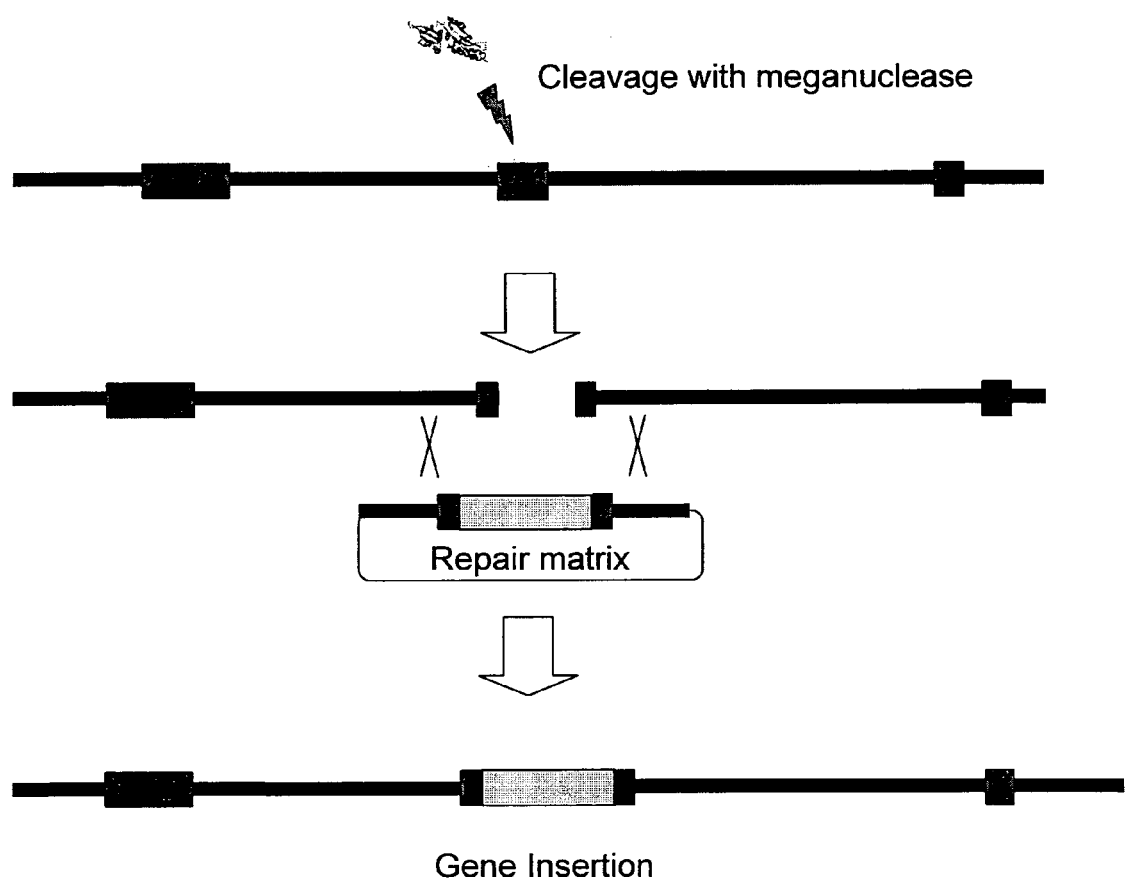

The combinatorial approach described in Smith et al., Nucleic Acids Res., 2006 and illustrated in FIG. 3, was used to engineer the DNA binding domain of I-CreI, and cleave a 22 bp (non-palindromic) sequence named rosa1 (FIG. 5) and located at position 8304, in exon 2 of the mouse ROSA26 locus (accession number CQ880114; SEQ ID NO: 3). Meganucleases cleaving the rosa1 sequence could be used to knock-in genes in the mouse ROSA26 locus (FIG. 4). Applications are in the following fields: production of recombinant proteins in mouse cells, engineering of recombinant cell lines, for example for drug screening purpose, and engineering of transgenic mice, for example for use as animal models.

The rosa1 sequence is partly a patchwork of the 10GGG_P, 5GAT_P and 5TAT_P targets (FIG. 5), which are cleaved by previously identified meganucleases, obtained as described in International PCT Applications WO 2006/097784, WO 2006/097853 and WO 2007/049156; Arnould et al., J. Mol. Biol., 2006, 355, 443-458 and Smith et al., Nucleic Acids Res., Epub 27 Nov. 2006. Thus rosa1 could be cleaved by meganucleases combining the mutations found in the I-CreI derivatives cleaving these three targets.

The 10GGG_P, 5GAT_P and 5TAT_P sequences are 24 by derivatives of C1221, a palindromic sequence cleaved by I-CreI (International PCT Applications WO 2006/097784, WO 2006/097853 and WO 2007/049156; Arnould et al., J. Mol. Biol., 2006, 355, 443-458 and Smith et al., Nucleic Acids Res., Epub 27 Nov. 2006). However, the structure of I-CreI bound to its DNA target suggests that the two external base pairs of these targets (positions −12 and 12) have no impact on binding and cleavage (Chevalier et al., Nat. Struct. Biol., 2001, 8, 312-316; Chevalier B. S. and Stoddard B. L., Nucleic Acids Res., 2001, 29, 3757-3754; Chevalier et al., J. Mol. Biol., 2003, 329, 253-269), and in this study, only positions −11 to 11 were considered. Consequently, the rosa1 series of targets were defined as 22 by sequences instead of 24 bp.

Rosa1 differs from C1221 in one base pair of the 4 bp central region. According to the structure of the I-CreI protein bound to its target, there is no contact between the 4 central base pairs (positions −2 to 2) and the I-CreI protein (Chevalier et al., Nat. Struct. Biol., 2001, 8, 312-316; Chevalier B. S. and Stoddard B. L., Nucleic Acids Res., 2001, 29, 3757-3754; Chevalier et al., J. Mol. Biol., 2003, 329, 253-269). Thus, the bases at these positions are not supposed to impact the binding efficiency. However, they could affect cleavage, which results from two nicks at the edge of this region. Thus, the GTTC sequence in −2 to 2 were first substituted with the GTAC sequence from C1221, resulting in target rosa1.2 (FIG. 5)

Then, two palindromic targets, rosa1.3 and rosa1.4, were derived from rosa1.2 (FIG. 5). Since rosa1.3 and rosa1.4 are palindromic, they should be cleaved by homodimeric proteins.

Thus proteins able to cleave the rosa1.3 and rosa1.4 sequences as homodimers, were first designed (examples 2 and 3), and then coexpressed to obtain heterodimers cleaving rosa1 (example 4). Heterodimers cleaving the rosa1.2 and rosa1 targets could be identified. In order to improve cleavage activity for the rosa1 target, we chose a series of chosen mutants cleaving rosa1.3 and rosa1.4 was then refined; the chosen mutants were randomly mutagenized, and used to form novel heterodimers that were screened against the rosa1 target (examples 5 and 6). Finally, heterodimers cleaving the rosa1 target could be identified, displaying a high cleavage activity in yeast and CHO cells.

EXAMPLE 2

Making of Meganucleases Cleaving Rosa1.3

This example shows that I-CreI mutants can cut the rosa1.3 DNA target sequence derived from the left part of the rosa1 target in a palindromic form (FIG. 5).

Target sequences described in this example are 22 bp palindromic sequences. Therefore, they will be described only by the first 11 nucleotides, followed by the suffix _P. For example, target rosa1.3 will be noted also caacatgatgt_P; SEQ ID NO: 35)).

The rosa1.3 target is similar to 5GAT_P at positions ±1, ±2, ±3, ±4, ±5, ±7, ±9, ±10 and ±11, the two sequences differing only at positions ±6 and ±8. It was hypothesized that positions ±6 would have little effect on the binding and cleavage activity. Mutants able to cleave 5GAT_P (caaaacgatgt_P; SEQ ID NO: 32) were previously obtained by mutagenesis on I-CreI N75 at positions 24, 44, 68, 70, 75 and 77, as described in Arnould et al., J. Mol. Biol., 2006, 355, 443-458 and International PCT Applications WO 2006/097784 and WO 2006/097853. In this example, it was checked whether mutants cleaving the 5GAT_P target could also cleave the rosa1.3 target.

1) Material and Methods

The method for producing meganuclease variants and the assays based on cleavage-induced recombination in mammal or yeast cells, which are used for screening variants with altered specificity are described in the International PCT Application WO 2004/067736; Epinat et al., Nucleic Acids Res., 2003, 31, 2952-2962; Chames et al., Nucleic Acids Res., 2005, 33, e178, and Arnould et al., J. Mol. Biol., 2006, 355, 443-458. These assays result in a functional LacZ reporter gene which can be monitored by standard methods.

a) Construction of Target Vector

Figure 6:
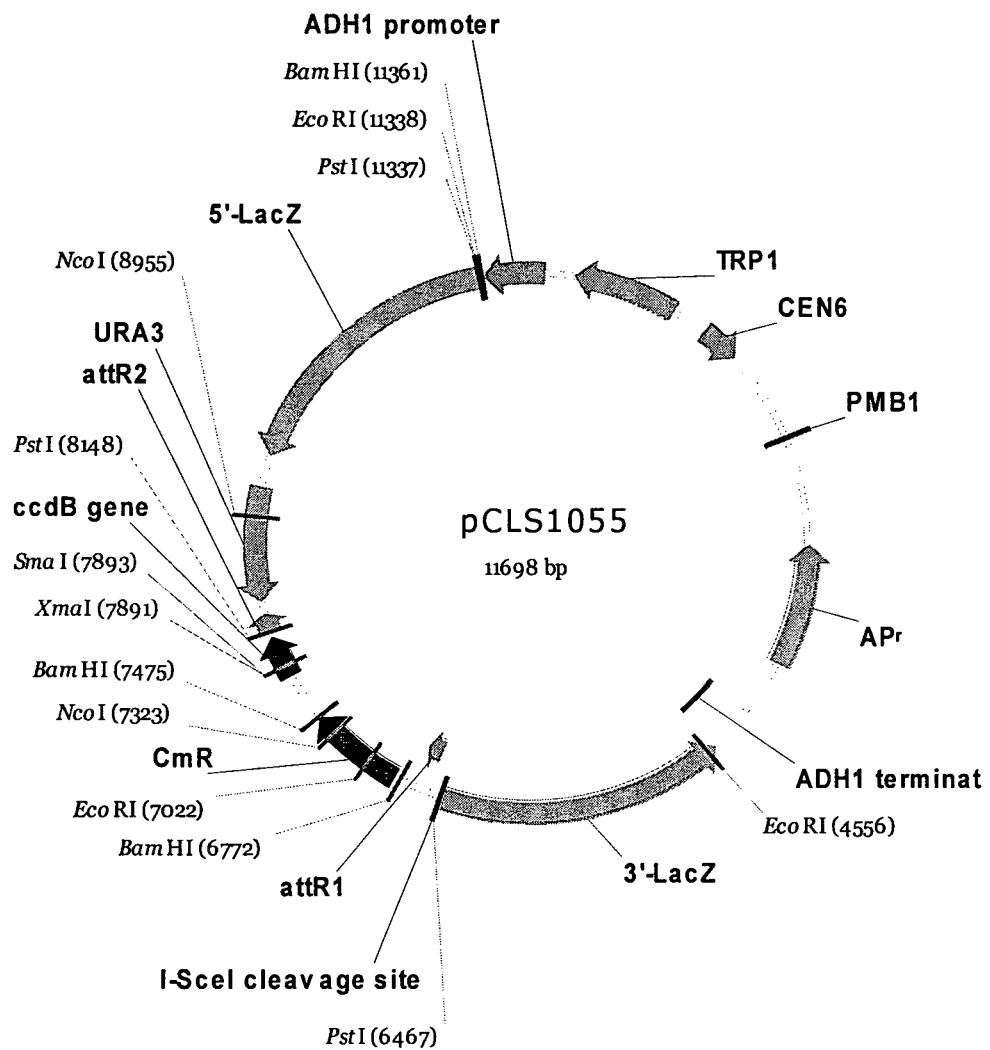
FIG. 6 represents the pCLS1055 vector map.

The target was cloned as follow: oligonucleotide corresponding to the target sequence flanked by gateway cloning sequence was ordered from PROLIGO: 5' 5' tggcata-caagtttcaacatgatgtacatcatgttgacaatcgtctgtca 3' (SEQ ID NO: 37). Double-stranded target DNA, generated by PCR amplification of the single stranded oligonucleotide, was cloned using the Gateway protocol (INVITROGEN) into yeast reporter vector (pCLS1055, FIG. 6). Yeast reporter vector was transformed into S. cerevisiae strain FYBL2-7B (MAT a, ura3Δ851, trp1Δ63, leu2Δ1, lys2Δ202).

b) I-CreI Mutants

Figure 7:
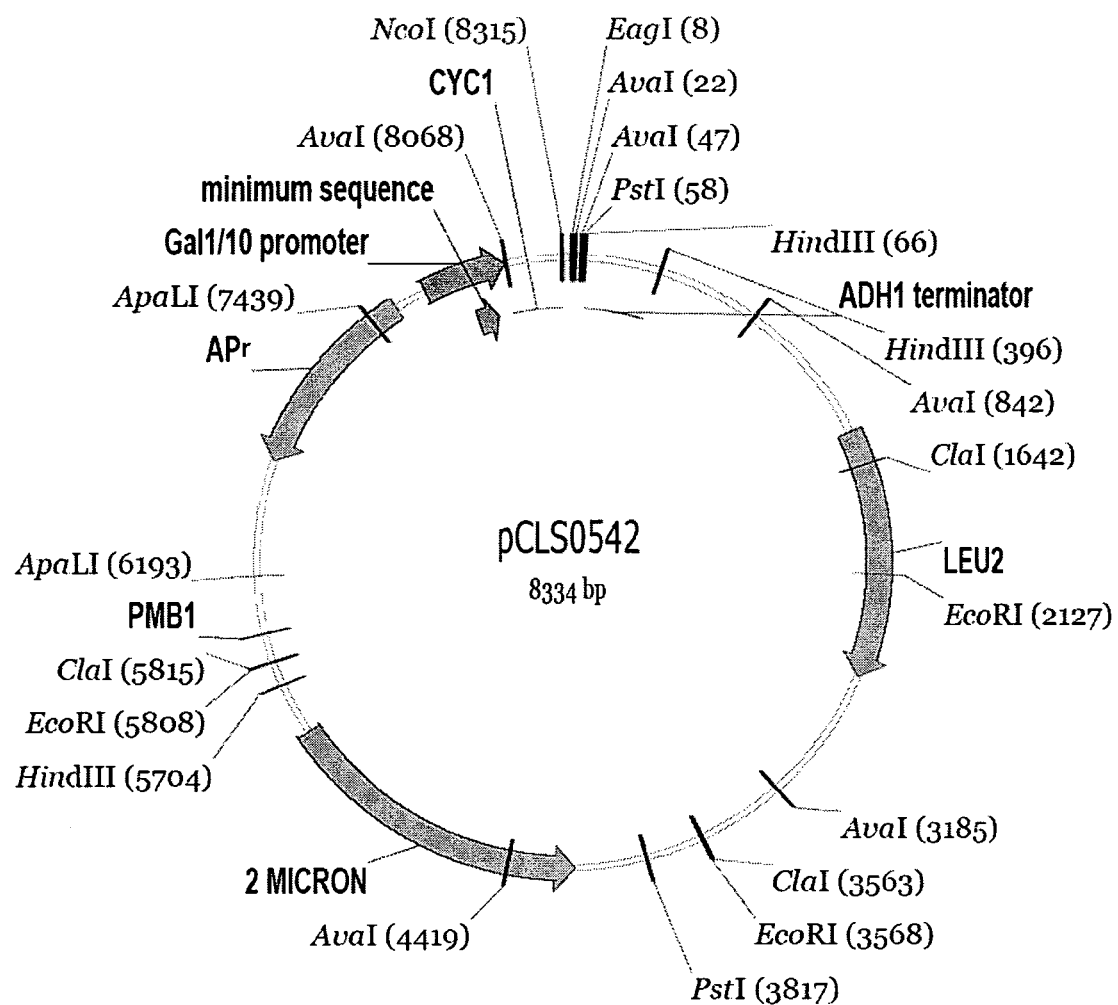
FIG. 7 represents the pCLS0542 vector map.

I-CreI mutants cleaving 5GAT_P were identified in a library where positions 24, 44, 68, 70, 75 and 77 of I-CreI are mutated, as described previously in Arnould et al., J. Mol. Biol., 2006, 355, 443-458 and International PCT Applications WO 2006/097784 and WO 2006/097853. They are cloned in the DNA vector (pCLS0542, FIG. 7) and expressed in the yeast Saccharomyces cerevisiae strain FYC2-6A (MATα, trp1Δ63, leu2Δ1, his3Δ200).

c) Mating of Meganuclease Expressing Clones and Screening in Yeast:

Screening was performed as described previously (Arnould et al., J. Mol. Biol., 2006, 355, 443-458). Mating was performed using a colony gridder (QpixII, Genetix). Mutants were gridded on nylon filters covering YPD plates, using a low gridding density (about 4 spots/cm²). A second gridding process was performed on the same filters to spot a second layer consisting of different reporter-harboring yeast strains for each target. Membranes were placed on solid agar YPD rich medium, and incubated at 30° C. for one night, to allow mating. Next, filters were transferred to synthetic medium, lacking leucine and tryptophan, with galactose (2%) as a carbon source, and incubated for five days at 37° C., to select for diploids carrying the expression and target vectors. After 5 days, filters were placed on solid agarose medium with 0.02% X-Gal in 0.5 M sodium phosphate buffer, pH 7.0, 0.1% SDS, 6% dimethyl formamide (DMF), 7 mM β-mercaptoethanol, 1% agarose, and incubated at 37° C., to monitor β-galactosidase activity. Results were analyzed by scanning and quantification was performed using appropriate software.

d) Sequencing of Mutants

To recover the mutant expressing plasmids, yeast DNA was extracted using standard protocols and used to transform E. coli. Sequence of mutant ORF were then performed on the plasmids by MILLEGEN SA. Alternatively, ORFs were amplified from yeast DNA by PCR (Akada et al., Biotechniques, 2000, 28, 668-670), and sequence was performed directly on PCR product by MILLEGEN SA.

2) Results

I-CreI mutants cleaving the 5GAT_P target, previously identified in a library where positions 24, 44, 68, 70, 75 and 77 of I-CreI are mutated, were screened for cleavage against the rosa1.3 DNA target (caacatgatgt_P; SEQ ID NO: 35). A total of 63 positive clones were found, rearranged in a 96-well plate and validated by secondary screening (FIG. 8). Among those positive clones, 22 (circled in FIG. 8) were chosen. Those 22 positives clones were sequenced. They turned out to correspond to 18 different novel endonucleases cleaving the rosa1.3 target (named m1 to m18: SEQ ID NO: 38 to 55; Table II).

TABLE II

I-CreI mutants capable of cleaving the rosa1.3 DNA target

| Position on FIG. 8 | Name | Sequence SEQ ID NO: | Amino acids at positions 24, 44, 68, 70, 75 and 77 (ex: VYRSYI stands for V24, Y44, R68, S70, Y75 and I77) |
|---|---|---|---|
| A1 and F3 | m1 | 38 | VYRSYI |
| A3 | m2 | 39 | VYRSNI |
| A5 and B1 | m3 | 40 | VYDSRR |
| A9 | m4 | 41 | ITYSYR |
| A11 | m5 | 42 | VYRSYQ |
| B3, D5 and E6 | m6 | 43 | VYYSYR |
| B8 | m7 | 44 | VYYSRA |
| B9 | m8 | 45 | VYRSNV |
| B10 | m9 | 46 | VNYSYR |
| B11 | m10 | 47 | VNYSYR + 82T* |
| C3 | m11 | 48 | VYSSRV |
| C8 | m12 | 49 | VYNSRI |
| C11 | m13 | 50 | VYSSRI |
| D6 | m14 | 51 | VYRSQI |
| D9 | m15 | 52 | IYRSNI |

TABLE II-continued

I-CreI mutants capable of cleaving the rosa1.3 DNA target

| Position on FIG. 8 | Name | Sequence SEQ ID NO: | Amino acids at positions 24, 44, 68, 70, 75 and 77 (ex: VYRSYI stands for V24, Y44, R68, S70, Y75 and I77) |
|---|---|---|---|
| D12 | m16 | 53 | VYYSRV |
| E1 | m17 | 54 | VYRSYT |
| E11 | m18 | 55 | VNSSRV |

*82T in m10 is an unexpected mutation that may be due to an error introduced by the PCR reaction before sequencing of yeast DNA.

EXAMPLE 3

Making of Meganucleases Cleaving Rosa1.4

This example shows that I-CreI mutants can cut the rosa1.4 DNA target sequence derived from the right part of the rosa1 target in a palindromic form (FIG. 5). All targets sequences described in this example are 22 bp palindromic sequences. Therefore, they will be described only by the first 11 nucleotides, followed by the suffix _P. For example, rosa1.4 will be called tgggattatgt_P (SEQ ID NO: 36).

The rosa1.4 target is similar to 5TAT_P at positions ±1, ±2, ±3, ±4, ±5 and ±7 and to 10GGG_P at positions ±1, ±2, ±7, ±8, ±9 and ±10. It was hypothesized that positions ±6 and ±11 would have little effect on the binding and cleavage activity. Mutants able to cleave 5TAT_P were previously obtained by mutagenesis on I-CreI N75 at positions 44, 68, 70, as described in Arnould et al., J. Mol. Biol., 2006, 355, 443-458 and International PCT Applications WO 2006/097784 and WO 2006/097853. Mutants able to cleave the 10GGG_P target were obtained by mutagenesis on I-CreI N75 at positions 28, 30, 33, 38, 40 and 70, as described in Smith et al., Nucleic Acids Res., Epub 27 Nov. 2006 and International PCT Application WO 2007/049156.

Both sets of proteins are mutated at position 70. However, it was hypothesized that two separable functional subdomains exist. That implies that this position has little impact on the specificity towards the bases ±8 to 10 of the target.

Therefore, to check whether combined mutants could cleave the rosa1.4 target, mutations at positions 44, 68 and 70 from proteins cleaving 5TAT_P (caaaactatgt_P; SEQ ID NO: 33) were combined with the 28, 30, 33, 38 and 40 mutations from proteins cleaving 10GGG_P (cgggacgtcgt_P; SEQ ID NO: 31).

1) Material and Methods

The experimental procedures are as described in example 2 and as follows:

Construction of Combinatorial Mutants

I-CreI mutants cleaving 10GGG_P or 5TAT_P were identified in Smith et al, Nucleic Acids Res. Epub 27 Nov. 2006; International PCT Application WO 2007/049156, and Arnould et al., J. Mol. Biol., 2006, 355, 443-458; International PCT Applications WO 2006/097784 and WO 2006/097853, respectively for the 10GGG_P or 5TAT_P targets. In order to generate I-CreI derived coding sequence containing mutations from both series, separate overlapping PCR reactions were carried out that amplify the 5' end (aa positions 1-43) or the 3' end (positions 39-167) of the I-CreI coding sequence. For both the 5' and 3' end, PCR amplification is carried out using primers Gal10F 5'-gcaactttagtgctgacacata-cagg-3' (SEQ ID NO: 56) or Gal10R 5'-acaaccttgattggagact-tgacc-3'(SEQ ID NO: 57), specific to the vector (pCLS0542, FIG. 7) and primers assF 5'-ctannnttgaccttt-3' (SEQ ID NO: 58) or assR 5'-aanggtcaannntag-3' (SEQ ID NO: 59) where nnn code for residue 40, specific to the I-CreI coding sequence for amino acids 39-43. The PCR fragments resulting from the amplification reaction realized with the same primers and with the same coding sequence for residue 40 were pooled. Then, each pool of PCR fragments resulting from the reaction with primers Gal10F and assR or assF and Gal10R was mixed in an equimolar ratio. Finally, approximately 25 ng of each final pool of the two overlapping PCR fragments and 75 ng of vector DNA (pCLS0542) linearized by digestion with NcoI and EagI were used to transform the yeast Saccharomyces cerevisiae strain FYC2-6A (MATα, trp1Δ63, leuΔ1, his3Δ200) using a high efficiency LiAc transformation protocol (Gietz and Woods, Methods Enzymol., 2002, 350, 87-96). An intact coding sequence containing both groups of mutations is generated by in vivo homologous recombination in yeast.

2) Results

I-CreI combinatorial mutants were constructed by associating mutations at positions 44, 68 and 70 with the 28, 30, 33, 38 and 40 mutations on the I-CreI N75 scaffold, resulting in a library of complexity 2208. Examples of combinatorial mutants are displayed in Table III. This library was transformed into yeast and 3456 clones (1.5 times the diversity) were screened for cleavage against the rosa1.4 DNA target (tgggattatgt_P; SEQ ID NO: 36). A total of 69 positive clones were found and were rearranged in a 96-well plate and validated by secondary screening (FIG. 9). Among those positives, 15 clones (circled in FIG. 9) were chosen. After sequencing, these 15 clones turned out to correspond to 8 different novel endonucleases cleaving the rosa1.4 DNA target (SEQ ID NO: 60 to 67; Table III).

TABLE III

Cleavage of the rosa1.4 target by the combinatorial variants

| | | Amino acids at positions 28, 30, 33, 38 and 40 (ex: ENRRR stands for E28, N30, R33, R38 and R40) | | | | | | |
|---|---|---|---|---|---|---|---|---|
| | | ENRRR | ENRRK | KNHAS | KNHSS | KNHQS | KNRAT | RNRDR |
| Amino acids at positions 44, 68 and 70 (ex: AHQ stands for A44, H68 and Q70) | AHQ | + | + | | | | | |
| | ARN | + | | | | | | |
| | ARS | | | + | | | | |
| | VRA | | | + | | | | |
| | ARG | | | + | | | | |
| | ASQ | + | | | | | | |
| | ATN | | | + | | | | |
| | RAG | | | | | | | |
| | ANN | | | | | | | |

TABLE III-continued

Cleavage of the rosa1.4 target by the combinatorial variants

Amino acids at positions 28, 30, 33, 38 and 40
(ex: ENRRR stands for E28, N30, R33, R38 and R40)

| | ENRRR | ENRRK | KNHAS | KNHSS | KNHQS | KNRAT | RNRDR |
|---|---|---|---|---|---|---|---|
| AQH | | | | | | | |
| ARH | | | | | | | |
| ARL | | | | | | | |
| ART | | | | | | | |
| NRN | | | | | | | |
| AQA | | | | | | | |

Only 105 out of the 2208 combinations are displayed).
+ indicates that a functional combinatorial mutant was found among the sequenced positives.

EXAMPLE 4

Making of Meganucleases Cleaving Rosa1

I-CreI mutants able to cleave each of the palindromic rosa1 derived targets (rosa1.3 and rosa1.4) were identified in examples 2 and 3. Pairs of such mutants (one cutting rosa1.3 and one cutting rosa1.4) were co-expressed in yeast. Upon coexpression, there should be three active molecular species, two homodimers, and one heterodimer. It was assayed whether the heterodimers that should be formed cut the non palindromic rosa1 and rosa1.2 DNA targets.

1) Material and Methods
a) Cloning of Mutants in Kanamycin Resistant Vector

To co-express two I-CreI mutants in yeast, mutants cutting the rosa1.4 sequence were subcloned in a yeast expression vector marked with a kanamycin resistance gene (pCLS1107, FIG. 10). Mutants were amplified by PCR reaction using primers common for pCLS0542 and pCLS1107: Gal10F 5'-gcaactttagtgctgacacatacagg-3' (SEQ ID NO: 56) and Gal10R 5'-acaaccttgattggagacttgacc-3'(SEQ ID NO: 57). Approximately 25 ng of PCR fragment and 2 5 ng of vector DNA (pCLS1107) linearized by digestion with DraIII and NgoMIV are used to transform the yeast *Saccharomyces cerevisiae* strain FYC2-6A (MATα, trp1Δ63, leu2Δ1, his3Δ200) using a high efficiency LiAc transformation protocol. An intact coding sequence for the I-CreI mutant is generated by in vivo homologous recombination in yeast. Each yeast strain containing a mutant cutting the rosa1.4 target subcloned in pCLS1107 vector was then mated with yeast expressing the rosa1.4 target to validate it. To recover the mutant expressing plasmids, yeast DNA was extracted using standard protocols and used to transform *E. coli*. and prepare *E. coli* DNA.
b) Mutants Coexpression Yeast strain expressing a mutant cutting the rosa1.3 target in pCLS0542 expression vector was transformed with DNA coding for a mutant cutting the rosa1.4 target in pCLS1107 expression vector. Transformants were selected on −L Glu+ G418 medium.

c) Mating of Meganucleases Coexpressing Clones and Screening in Yeast

Mating was performed using a colony gridder (QpixII, Genetix). Mutants were gridded on nylon filters covering YPD plates, using a low gridding density (about 4 spots/cm$^2$). A second gridding process was performed on the same filters to spot a second layer consisting of different reporter-harbouring yeast strains for each target. Membranes were placed on solid agar YPD rich medium, and incubated at 30° C. for one night, to allow mating. Next, filters were transferred to synthetic medium, lacking leucine and tryptophan, adding G418, with galactose (1%) as a carbon source, and incubated for five days at 37° C., to select for diploids carrying the expression and target vectors. After 5 days, filters were placed on solid agarose medium with 0.02% X-Gal in 0.5 M sodium phosphate buffer, pH 7.0, 0.1% SDS, 6% dimethyl formamide (DMF), 7 mM β-mercaptoethanol, 1% agarose, and incubated at 37° C., to monitor β-galactosidase activity. Results were analyzed by scanning and quantification was performed using appropriate software.

Results

Coexpression of mutants cleaving the rosa1.3 target (m1 to m18 described in Table II) and the eight mutants cleaving the rosa1.4 target (described in Table III) resulted in efficient cleavage of the rosa1.2 target in all the cases (screen examples are shown in FIG. 11A). All combinations tested are summarized in Table IV. Most of these combinations are also able to cut the rosa1 natural target that differs from the rosa1.2 sequence just by 1 bp at position +1 (FIG. 5). As shown on FIG. 11B, the signal observed on rosa1 natural target is weak compared to the one observed on rosa1.2 target. The combinations cleaving the rosa1 DNA target are presented in Table V.

TABLE IV

Combinations that resulted in cleavage of the rosa1.2 target

Mutants cutting rosa1.4
amino acids at positions 28, 30, 33, 38, 40/44, 68 and 70
(ex: ENRRR/AHQ stands for E28, N30, R33, R38, R40/A44, H68 and Q70)

| | | | ENRRR/ AHQ | ENRRR/ ARN | ENRRR/ ASQ | ENRRK/ AHQ | ENRRK/ ARS | ENRRK/ VRA | ENRRK/ ARG | ENRRK/ ATN |
|---|---|---|---|---|---|---|---|---|---|---|
| Mutants cutting rosa1.3 | | m1 | VYRSYI | + | + | + | + | + | + | + | + |
| amino acids at positions 24, | | m2 | VYRSNI | + | + | + | + | + | + | + | + |
| 44, 68, 70, 75 and 77 | | m3 | VYDSRR | + | + | + | + | + | + | + | + |
| (ex: VYRSYI stands for V24, | | m4 | ITYSYR | + | + | + | + | + | + | + | + |

TABLE IV-continued

Combinations that resulted in cleavage of the rosa1.2 target

Mutants cutting rosa1.4
amino acids at positions 28, 30, 33, 38, 40/44, 68 and 70
(ex: ENRRR/AHQ stands for E28, N30, R33, R38, R40/A44, H68 and Q70)

|  |  |  | ENRRR/ AHQ | ENRRR/ ARN | ENRRR/ ASQ | ENRRK/ AHQ | ENRRK/ ARS | ENRRK/ VRA | ENRRK/ ARG | ENRRK/ ATN |
|---|---|---|---|---|---|---|---|---|---|---|
| Y44, R68, S70, Y75 and I77) | m5 | VYRSYQ | + | + | + | + | + | + | + | + |
|  | m6 | VYYSYR | + | + | + | + | + | + | + | + |
|  | m7 | VYYSRA | + | + | + | + | + | + | + | + |
|  | m8 | VYRSNV | + | + | + | + | + | + | + | + |
|  | m9 | VNYSYR | + | + | + | + | + | + | + | + |
|  | m10 | VNYSYR + 82T | + | + | + | + | + | + | + | + |
|  | m11 | VYSSRV | + | + | + | + | + | + | + | + |
|  | m12 | VYNSRI | + | + | + | + | + | + | + | + |
|  | m13 | VYSSRI | + | + | + | + | + | + | + | + |
|  | m14 | VYRSQI | + | + | + | + | + | + | + | + |
|  | m15 | IYRSNI | + | + | + | + | + | + | + | + |
|  | m16 | VYYSRV | + | + | + | + | + | + | + | + |
|  | m17 | VYRSYT | + | + | + | + | + | + | + | + |
|  | m18 | VNSSRV | + | + | + | + | + | + | + | + |

+ indicates that the heterodimeric mutant cleaves the rosa1.2 target

TABLE V

Combinations that resulted in cleavage of the rosa1 target

Mutants cutting rosa1.4
amino acids at positions 28, 30, 33, 38, 40/44, 68 and 70
(ex: ENRRR/AHQ stands for E28, N30, R33, R38, R40/A44, H68 and Q70)

|  |  |  | ENRRR/ AHQ | ENRRR/ ARN | ENRRR/ ASQ | ENRRK/ AHQ | ENRRK/ ARS | ENRRK/ VRA | ENRRK/ ARG | ENRRK/ ATN |
|---|---|---|---|---|---|---|---|---|---|---|
| Mutants cutting rosa1.3 | m1 | VYRSYI |  |  |  |  |  |  |  |  |
| amino acids at positions 24, | m2 | VYRSNI | + | + |  | + |  | + | + |  |
| 44, 68, 70, 75 and 77 | m3 | VYDSRR |  |  |  |  |  |  |  |  |
| (ex: VYRSYI stands for V24, | m4 | ITYSYR |  |  |  |  |  |  |  |  |
| Y44, R68, S70, Y75 and I77) | m5 | VYRSYQ |  |  |  |  |  |  |  |  |
|  | m6 | VYYSYR | + | + |  | + |  | + | + |  |
|  | m7 | VYYSRA |  |  |  |  |  |  |  |  |
|  | m8 | VYRSNV | + | + |  | + |  | + | + |  |
|  | m9 | VNYSYR |  |  |  |  |  |  |  |  |
|  | m10 | VNYSYR + 82T |  |  |  |  |  |  |  |  |
|  | m11 | VYSSRV |  |  |  |  |  |  |  |  |
|  | m12 | VYNSRI | + | + |  | + | + | + | + | + |
|  | m13 | VYSSRI | + | + |  | + | + | + | + | + |
|  | m14 | VYRSQI | + | + |  | + | + | + | + | + |
|  | m15 | IYRSNI |  |  |  |  |  |  |  |  |
|  | m16 | VYYSRV | + | + |  | + | + | + | + | + |
|  | m17 | VYRSYT | + | + | + | + | + | + | + | + |
|  | m18 | VNSSRV |  |  |  |  |  |  |  |  |

+ indicates that the heterodimeric mutant cleaves the rosa1.2 target

EXAMPLE 5

Refinement of Meganucleases Cleaving Rosa1 by Random Mutagenesis of Proteins Cleaving Rosa1.4 and Assembly with Proteins Cleaving Rosa1.3

I-CreI mutants able to cleave the non palindromic rosa1.2 and rosa1 targets were identified by assembly of mutants cleaving the palindromic rosa1.3 and rosa1.4 targets. However, the combinations were able to efficiency cleave rosa1.2 but weakly cleave rosa1, which differs from rosa1.2 only by 1 bp at position 1. The signal observed on rosa1 is not sufficient.

Therefore protein combinations cleaving rosa1 were mutagenized, and mutants cleaving rosa1 efficiently were screened. According to the structure of the I-CreI protein bound to its target, there is no contact between the 4 central base pairs (positions −2 to 2) and the I-CreI protein (Chevalier et al., Nat. Struct. Biol., 2001, 8, 312-316; Chevalier B. S. and Stoddard B. L., Nucleic Acids Res., 2001, 29, 3757-3754; Chevalier et al., J. Mol. Biol., 2003, 329, 253-269). Thus, it is difficult to rationally choose a set of positions to mutagenize, and mutagenesis was done on the C-terminal part of the protein (83 last amino acids) or on the whole protein. Random mutagenesis results in high complexity libraries, and the complexity of the variants libraries to be tested was limited by mutagenizing only one of the two components of the heterodimers cleaving rosa1.

Thus, proteins cleaving rosa1.4 were mutagenized, and it was tested whether they could efficiency cleave rosa1 when co-expressed with proteins cleaving rosa1.3.

1) Material and Methods
a) Random Mutagenesis:
Random mutagenesis libraries were created on pools of chosen mutants, by PCR using $Mn^{2+}$ or derivatives of dNTPs as 8-oxo-dGTP and dPTP in two-step PCR process as described in the protocol from JENA BIOSCIENCE GmbH in JBS dNTP-Mutagenesis kit. For random mutagenesis on the whole protein, primers used are: preATGCreFor (5'-gcat-aaattactatacttctatagacacgcaaacacaaatacacagcggccttgccacc-3'; SEQ ID NO: 68) and ICreIpostRev (5'-ggctcgag-gagctcgtctagaggatcgctcgagttatcagtcggccgc-3'; SEQ ID NO: 69). For random mutagenesis on the C-terminal part of the protein, primers used are: AA78a83For (5'-ttaagcgaaat-caagccg-3'; SEQ ID NO: 70) and ICreIpostRev with dNTPs derivatives; the rest of the protein is amplified with a high fidelity taq polymerase and without dNTPs derivatives using primers preATGCreFor and AA78a83Rev (5'-cggct-tgatttcgcttaa-3'; SEQ ID NO: 71).

Pools of mutants were amplified by PCR reaction using these primers common for pCLS0542 (FIG. 7) and pCLS1107 (FIG. 10). Approximately 75 ng of PCR fragment and 75 ng of vector DNA (pCLS1107) linearized by digestion with DraIII and NgoMIV are used to transform the yeast *Saccharomyces cerevisiae* strain FYC2-6A (MATα, trp1Δ63, leu2Δ1, his3Δ200) using a high efficiency LiAc transformation protocol. A library of intact coding sequence for the I-CreI mutant is generated by in vivo homologous recombination in yeast. Positives resulting clones were verified by sequencing as described in example 2.

b) Cloning of Mutants in Leucine Expression Vector in the Yeast Strain Containing the Rosa1 Target:

The yeast strain FYBL2-7B (MAT a, ura3Δ851, trp1Δ63, leu2Δ1, lys2Δ202) containing the rosa1 target into yeast reporter vector (pCLS1055, FIG. 6) is transformed with mutants cutting rosa1.3 target, in the pCLS0542 vector, marked with LEU2 gene, using a high efficiency LiAc transformation protocol. The resulting yeast strains are used as targets for mating assays as described in example 4.

2) Results

Four mutants cleaving rosa1.4 (ERRR/AHQ, ERRR/ARN, ERRK/AHQ and ERRK/VRA according to Table V) were pooled, randomly mutagenized on all proteins or on the C terminal part of proteins and transformed into yeast. 4464 transformed clones were then mated with a yeast strain that (i) contains the rosa1 target in a reporter plasmid (ii) expresses a variant cleaving the rosa1.3 target, chosen among those described in example 2. Three such strains were used, expressing the I-CreI V24 Y44 S68 S70 R75 I77 (or VYSSRI) mutant, the I-CreI V24 Y44 R68 S70 Q75 I77 (or VYRSQI) mutant, or the I-CreI V24 Y44 R68 S70 Y75 T77 (or VYRSYT) mutant (see Table II). Two clones were found to trigger a better cleavage of the rosa1 target when mated with such yeast strain compared to the mutants before mutagenesis on the same yeast strain. In conclusion, two proteins able to efficiently cleave rosa1 when forming heterodimers with VYSSRI, VYRSQI or VYRSYT (Table VI) were identified. (FIG. 12)

TABLE VI

Functional mutant combinations displaying strong cleavage activity for rosa1 DNA target

| | | Optimized mutant rosa1.4* (SEQ ID NO: 72, 73) |
|---|---|---|
| Mutant cutting rosa1.3 amino acids at positions 24, 44, 68, 70, 75 and 77 (ex: VYRSYI stands for V24, Y44, R68, S70, Y75 and I77) | VYSSRI (m13) | MO_1: E28 R33 R38 R40 A44 H68 Q70 N75 A105 R107<br>MO_2: E28 R33 R38 K40 A44 H68 Q70 N75 A105 R107 A151 G153 E158 |
| | VYRSQI (m14) | MO_1: E28 R33 R38 R40 A44 H68 Q70 N75 A105 R107<br>MO_2: E28 R33 R38 K40 A44 H68 Q70 N75 A105 R107 A151 G153 E158 |
| | VYRSYT (m17) | MO_1: E28 R33 R38 R40 A44 H68 Q70 N75 A105 R107<br>MO_2: E28 R33 R38 K40 A44 H68 Q70 N75 A105 R107 A151 G153 E158 |

*mutations resulting from random mutagnenesis are in bold.

EXAMPLE 6

Refinement of Meganucleases Cleaving Rosa1 by Random Mutagenesis of Proteins Cleaving Rosa1.3 and Assembly with Refined Proteins Cleaving Rosa1.4

I-CreI mutants able to cleave the rosa1 target were identified by assembly of mutants cleaving rosa1.3 and refined mutants cleaving rosa1.4. To increase the activity of the meganucleases, the second component of the heterodimers cleaving rosa1 was mutagenized. In this example, mutants cleaving rosa1.3 were mutagenized, followed by screening of more efficient variants cleaving rosa1 in combination with the refined mutants cleaving rosa1.4 identified in example 5.

1) Material and Method
a) Random Mutagenesis:
Random mutagenesis libraries were created on pools of chosen mutants, by PCR using $Mn^{2+}$ or derivatives of dNTPs as 8-oxo-dGTP and dPTP in two-step PCR process as described in the protocol from JENA BIOSCIENCE GmbH in JBS dNTP-Mutagenesis kit. For random mutagenesis on the whole protein, primers used are: preATGCreFor (5'-gcat-aaattactatacttctatagacacgcaaacacaaatacacagcggccttgccacc-3'; SEQ ID NO: 68) and ICreIpostRev (5'-ggctcgag-gagctcgtctagaggatcgctcgagttatcagtcggccgc-3'; SEQ ID NO: 69). For random mutagenesis on the C-terminal part of the protein primer used are AA78a83For (5'-ttaagcgaaatcaagccg-3'; SEQ ID NO: 70) and ICreIpostRev with dNTPs derivatives; the rest of the protein is amplified with a high fidelity taq polymerase and without dNTPs derivatives using primers preATGCreFor and AA78a83Rev (5'-cggcttgatttcgcttaa-3'; SEQ ID NO: 71).

Pools of mutants were amplified by PCR reaction using these primers common for pCLS0542 (FIG. 7) and pCLS1107 (FIG. 10). Approximately 75 ng of PCR fragment and 75 ng of vector DNA (pCLS0542) linearized by digestion with NcoI and EagI are used to transform the yeast *Saccharomyces cerevisiae* strain FYC2-6A (MATα, trp1Δ63, leu2Δ1, his3Δ200) using a high efficiency LiAc transformation protocol. A library of intact coding sequence for the I-CreI mutant is generated by in vivo homologous recombination in yeast. Positives resulting clones were verified by sequencing as described in example 2.

b) Cloning of Mutants in Kanamycin Expression Vector in the Yeast Strain Containing the Rosa1 Target The yeast strain FYBL2-7B (MAT a, ura3Δ851, trp1Δ63, leu2Δ1, lys2Δ202) containing the rosa1 target into yeast reporter vector (pCLS1055, FIG. 6) is transformed with MO__1 and MO__2 refined mutants, cutting rosa1.4 target, in pCLS1107 vector, using a high efficiency LiAc transformation protocol. Mutant-target yeasts are used as targets for mating assays as described in example 4.

2) Results

Two pools of four mutants cleaving rosa1.3 (pool 1: VYRSNI, VYYSYR, VYRSNV and VYNSRI and pool 2: VYYSYR, VYSSRI, VYRSQI and VYRSYT according to Table V) were randomly mutagenized on all proteins or on the C terminal part of proteins and transformed into yeast. 8928 transformed clones were then mated with a yeast strain that (i) contains the rosa1 target in a reporter plasmid (ii) expresses a variant cleaving the rosa1.4 target. Two such strains were used expressing either the I-CreI E28 R33 R38 R40 A44 H68 Q70 N75 A105 R107 (or MO__1) mutant, either the I-CreI E28 R33 R38 K40 A44 H68 Q70 N75 A105 R107 A151 G153 E158 (or MO__2) mutant. Five clones were found to trigger a better cleavage of the rosa1 target when mated with such yeast strain compared to the mutants before mutagenesis with the same yeast strain (FIG. 13). After sequencing they turn out to correspond to four proteins. In conclusion, four proteins able to efficiently cleave rosa1 when forming heterodimers with MO__1 or MO__2, were identified (Table VII).

b) Re-cloning of Meganucleases

The ORF of I-CreI N75, I-SceI and I-CreI mutants identified in example 6 were amplified by PCR and sequenced (MILLEGEN). Then, ORFs were recloned using the Gateway protocol (INVITROGEN). ORFs were amplified by PCR of yeast DNA using the primers B1F: 5' ggggacaagtttgta-caaaaaagcaggcttcgaaggagata-gaaccatggccaataccaaatataacaaagagttcc 3' (SEQ ID NO: 78) and B2R: 5' ggggaccactttgtacaa-gaaagctgggtttagtcggccgccggggaggatttatcttctcgc 3' (SEQ ID NO: 79) from Proligo. PCR products were cloned in CHO gateway expression vector pcDNA6.2 from Invitrogen (pCLS1069, FIG. 15). Resulting clones were verified by sequencing as described in example 2.

c) Extrachromosomal Assay in Mammalian Cells

CHO cells were transfected with Polyfect transfection reagent according to the supplier's (QIAGEN) protocol. 72 hours after transfection, culture medium was removed and 150 μl of lysis/revelation buffer added for β-galactosidase liquid assay (typically, 1 liter of buffer contains 100 ml of lysis buffer (Tris-HCl 10 mM pH 7.5, NaCl 150 mM, Triton X100 0.1%, BSA 0.1 mg/ml, protease inhibitors), 10 ml of Mg 100× buffer (MgCl$_2$ 100 mM, β-mercaptoethanol 35%), 110 ml ONPG 8 mg/ml and 780 ml of sodium phosphate 0.1 M pH7.5). After incubation at 37° C., optical density was measured at 420 nm. The entire process is performed on an automated BioCel® platform (VELOCITY11).

2) Results

The results of two experiments presented in FIG. 16, show that two combinations of I-CreI mutants (mO__2/MO__1 and

TABLE VII

Functional mutant combinations displaying strong cleavage activity for rosa1 DNA target.

|  |  | Optimized mutant rosa1.3* (SEQ ID NO: 74 to 77) |
|---|---|---|
| Optimized mutant rosa1.4 | MO__1<br>E28 R33 R38 R40 A44<br>H68 Q70 N75 A105 R107 | mO__1: S19 V24 Y44 R68 S70 N75 V77<br>mO__2: S19 V24 Y44 R68 S70 Q75 I77<br>mO__3: V24 Y44 S68 S70 R75 I77 A105<br>mO__4: V24 Y44 S68 S70 R75 I77 G79 |
|  | MO__2<br>E28 R33 R38 K40 A44 H68<br>Q70 N75 A105 R107 A151<br>G153 E158 | mO__1: S19 V24 Y44 R68 S70 N75 V77<br>mO__2: S19 V24 Y44 R68 S70 Q75 I77<br>mO__3: V24 Y44 S68 S70 R75 I77 A105<br>mO__4: V24 Y44 S68 S70 R75 I77 G79 |

*mutations resulting from random mutagenesis are in bold

EXAMPLE 7

Validation of Rosa1 Target Cleavage in an Extrachromosomic Model in CHO Cells

In example 6, I-CreI refined mutants able to efficiently cleave the rosa1 target in yeast were identified. In this example, the ability of two combinations of mutants to cut the rosa1 target in CHO cells was tested using an extrachromosomal essay in mammalian cells.

1) Materials and Methods a) Cloning of Rosa1 Target in a Vector for CHO Screen

The target was cloned as follow: oligonucleotide corresponding to the target sequence flanked by gateway cloning sequence was ordered from Proligo: 5' tggcatacaagtttcaacat-gatgtacatcatgttgacaatcgtctgtca 3' (SEQ ID NO: 37). Double-stranded target DNA, generated by PCR amplification of the single stranded oligonucleotide, was cloned using the Gateway protocol (INVITROGEN) into CHO reporter vector (pCLS1058, FIG. 14).

mO__2/MO__2) are able to cut the rosa1 target in CHO cells with an activity similar as the activity of I-CreI N75 against the I-CreI target (tcaaaacgtcgtgagacagtttgg, SEQ ID NO: 80) or I-SceI against the I-SceI target (tagggataacagggtaat, SEQ ID NO: 81).

EXAMPLE 8

Genome Engineering at the ROSA26 Locus in Mouse Cells

I-CreI refined mutants able to efficiently cleave the rosa1 target in yeast and in an extrachromosomal assay in mammalian cells (CHO K1 cells) have been identified in examples 6 and 7. The ability of one combination of two I-CreI refined mutants to induce homologous recombination at the ROSA26 locus in mouse L cells was tested in this example.

1) Materials and Methods a) Knock-in (KI) Matrices

Two knock-in matrices comprising the hygromycin resistance gene coding sequence (CDS) cloned between two mouse ROSA26 homology arms, HG ROSA26 from 6283 to 8317 and HD ROSA26 from 8313 to 10319 in CQ880114 sequence (corresponding to SEQ ID NO: 3 in the sequence listing), were constructed. The resulting plasmids are pCLS1679 and pCLS1675 (plasmid map in FIG. 18). In pCLS1679, the coding sequence of the hygromycin resistance gene (hygro CDS) operatively linked to the SV40 polyA was cloned in pBR322 vector (PROMEGA) between HG ROSA26 and HD ROSA26. pCLS1675 differs from pCLS1679 by the insertion of an Internal Ribosomal Entry site (IRES; SEQ ID NO: 139) just upstream of the hygro CDS.

b) Cloning of Meganucleases

The ORF of I-CreI refined mutants mO_2 and MO_1 are described in example 6 (Table VII). Mutants expression was made in two expression vectors under the control of the human elongation factor 1 alpha (EF1α) promoter or cytomegalovirus immediate early (CMV) promoter (pCLS1069, FIG. 15). Mutants were cloned in pCLS1069 under CMV promoter as described in example 7. The resulting plasmids were verified by sequencing (MILLEGEN). In pCLS1761 (FIG. 19) and pCLS1762 (FIG. 20), the mO_2 and MO_1 I-CreI mutants, respectively, are under the control of the EF1α promoter.

c) Knock-in Experiment in Mouse L Cells

Mouse L cells (ATCC # CRL-2648) are cultivated in complete DMEM medium (DMEM Glutamax, GIBCO) supplemented with 10% fetal calf serum, penicillin, streptomycin and fungizon. Cells are transfected using lipofectamine reagent (INVITROGEN) according to the procedure recommended by the manufacturer. Two days after transfection, selection is performed using Hygromycin at 0.6 mg/ml in complete medium. After two weeks of selection, resistant clones are picked using a ClonePix robot (GENETIX). Clones are amplified one week in 96 wells plates in complete medium supplemented with hygromycin at 0.6 mg/ml. Genomic DNA is extracted from resistant clones cultured in 96 well plates using the ZR96 kit (ZYMO RESEARCH).

c) PCR Analysis of Knock-in Events

Knock-in events are detected by PCR analysis on genomic DNA using the pair of primers KI_GHG_S5 (5' tagtatacagaaactgttgcatcgc 3'; SEQ ID NO: 137) and HygSeqRev (5' cgtctgctgctccatacaag 3'; SEQ ID NO: 138), located respectively in the mouse ROSA26 sequence upstream of the HG ROSA26 homology arm and in the hygromycin CDS, to obtain a KI specific PCR amplification (FIG. 21).

2) Results

ROSA26 meganucleases used in this example are mO_2 and MO_1 described in example 6 (Table VII) and cloned in two expression vectors, under the control of the human elongation factor 1 alpha (EF1α) promoter (pCLS1761 and pCLS1762) or cytomegalovirus immediate early (CMV) promoter (pCLS1069, FIG. 15). Mouse L cells were cotransfected with three vectors: two plasmids expressing the mO_2 and MO_1 ROSA26 meganucleases and the KI matrix. The meganucleases were cloned in pCLS1761 and pCLS1762, respectively EF1α promoter and the KI matrix was pCLS1675.

A total of 2600000 mouse L cells were cotransfected with 2 µg of KI matrix vector and 5 µg or 10 µg of each meganuclease expression vector. As control of spontaneous KI frequency, the same number of cells was transfected with 2 µg of KI matrix vector alone. The transfection efficacy (40%) was determined by FACS analysing using a fluorescent marker expressing plasmid. The frequency of resistant clones was determined by counting the total number of hygromycin resistant clones and corrected by transfection efficacy. 2605, 1197 and 1902 hygromycin resistant clones were obtained, respectively (Table VIII). 92 or 184 clones were picked per condition and analysed by PCR as described in materials and methods. Results are presented in Table VIII.

TABLE VIII

PCR result and frequency of KI events at the ROSA26 locus in mouse L cells

| Vectors transfected | Total number of Hygro$^R$ clones | Corrected Hygro$^R$ frequency | Number of PCR positives/ Hygro$^R$ picked clones | KI events frequency |
|---|---|---|---|---|
| 2 µg pCLS1675 5 µg pCLS1761 5 µg pCLS1762 | 2605 | $2.5 \times 10^{-3}$ | 18/92 | $4.9 \times 10^{-4}$ |
| 2 µg pCLS1675 10 µg pCLS1761 10 µg pCLS1762 | 1197 | $1.1 \times 10^{-3}$ | 28/92 | $3.5 \times 10^{-4}$ |
| 2 µg pCLS1675 | 1902 | $1.8 \times 10^{-3}$ | 0/184 | 0 |

Cotransfection of ROSA26 meganucleases and KI matrix induced homologous recombination at the mouse ROSA26 locus in L cells at a maximal frequency of $4.9 \times 10^{-4}$. No spontaneous homologous recombination was observed with transfection of the KI matrix alone. This example illustrates the ability of ROSA26 meganucleases to induce homologous recombination at the mouse ROSA26 locus in mouse L cells.

EXAMPLE 9

Meganucleases Derived from mO_2 and MO_1

Meganuclease constructs were engineered from mO_2 (SEQ ID NO: 75) and MO_1 (SEQ ID NO: 72) by using conventional techniques of molecular biology and recombinant DNA, which are explained fully in Current Protocols in Molecular Biology (Frederick M. AUSUBEL, 2000, Wiley and son Inc, Library of Congress, USA); Molecular Cloning: A Laboratory Manual, Third Edition, (Sambrook et al, 2001, Cold Spring Harbor, N.Y.: Cold Spring Harbor Laboratory Press).

A NLS (KKKRK; SEQ ID NO: 134) was inserted between the first ($M_1$) and the second ($A_2$) amino acids of MO_1 and mO_2; the resulting variants are SEQ ID NO: 140 and 141, respectively.

A tag (TagHA; YPYDVPDYA; SEQ ID NO: 135) was inserted between the first ($M_1$) and the third amino acid ($N_3$) of mO_2; the resulting variant is SEQ ID NO: 142.

A tag (STag; KETAAAKFERQHMDS; SEQ ID NO: 136) was inserted between the first ($M_1$) and the second ($A_2$) amino acids of MO_1; the resulting variant is SEQ ID NO: 143.

A tag (TagHA; YPYDVPDYA; SEQ ID NO: 135) and a NLS (KKKRK; SEQ ID NO: 134) were inserted between the first ($M_1$) and the second amino acid ($A_2$) of mO_2; the resulting variant is SEQ ID NO: 144.

A tag (STag; KETAAAKFERQHMDS; SEQ ID NO: 136) and a NLS (KKKRK; SEQ ID NO: 134) were inserted between the first ($M_1$) and the second ($A_2$) amino acids of MO_1; the resulting variant is SEQ ID NO: 145.

A single-chain meganuclease comprising an MO_1 monomer (positions 1 to 166 of SEQ ID NO: 72) separated from a mO_2 monomer (positions 3 to 164 of SEQ ID NO: 75) by a linker (GGSDKYNQALSKYNQALSKYN-QALSGGGGS; SEQ ID NO: 149) was constructed: the resulting single-chain meganuclease is SEQ ID NO: 146.

An obligate heterodimer derived from mO_2/MO_1 was engineered by introducing the E8K and E61R mutations in a mO_2 monomer and the K7E and K96E mutations in a MO_1 monomer; the resulting heterodimer consists of SEQ ID NO: 147 and SEQ ID NO: 148.

The invention claimed is:

1. A method of making an I-CreI variant wherein one of the two I-CreI monomers has at least two substitutions, one in each of the two functional subdomains of the LAGLIDADG (SEQ ID NO: 150) core domain situated respectively from positions 26 to 40 and 44 to 77 of I-CreI, said variant being able to cleave a DNA target sequence from the mouse ROSA26 locus, wherein said method comprises:

(a) constructing a first series of I-CreI variants having at least one substitution in a first functional subdomain of the LAGLIDADG (SEQ ID NO: 150) core domain situated from positions 26 to 40 of I-CreI, (b) constructing a second series of I-CreI variants having at least one substitution in a second functional subdomain of the LAGLIDADG (SEQ ID NO: 150) core domain situated from positions 44 to 77 of I-CreI, (c) selecting or screening, or both, the variants from the first series of (a) which are able to cleave a mutant I-CreI site wherein at least (i) the nucleotide triplet at positions −10 to −8 of the I-CreI site has been replaced with the nucleotide triplet which is present at position −10 to −8 of said DNA target sequence from the mouse ROSA26 locus and (ii) the nucleotide triplet at positions +8 to +10 has been replaced with the reverse complementary sequence of the nucleotide triplet which is present at position −10 to −8 of said DNA target sequence from the mouse ROSA26 locus, (d) selecting or screening, or both, the variants from the second series of (b) which are able to cleave a mutant I-CreI site wherein at least (i) the nucleotide triplet at positions −5 to −3 of the I-CreI site has been replaced with the nucleotide triplet which is present at position −5 to −3 of said DNA target sequence from the mouse ROSA26 locus and (ii) the nucleotide triplet at positions +3 to +5 has been replaced with the reverse complementary sequence of the nucleotide triplet which is present at position −5 to −3 of said DNA target sequence from the mouse ROSA26 locus, (e) selecting or screening, or both, the variants from the first series of (a) which are able to cleave a mutant I-CreI site wherein at least (i) the nucleotide triplet at positions +8 to +10 of the I-CreI site has been replaced with the nucleotide triplet which is present at positions +8 to +10 of said DNA target sequence from the mouse ROSA26 locus and (ii) the nucleotide triplet at positions −10 to −8 has been replaced with the reverse complementary sequence of the nucleotide triplet which is present at position +8 to +10 of said DNA target sequence from the mouse ROSA26 locus, (f) selecting or screening, or both, the variants from the second series of (b) which are able to cleave a mutant I-CreI site wherein at least (i) the nucleotide triplet at positions +3 to +5 of the I-CreI site has been replaced with the nucleotide triplet which is present at positions +3 to +5 of said DNA target sequence from the mouse ROSA26 locus and (ii) the nucleotide triplet at positions −5 to −3 has been replaced with the reverse complementary sequence of the nucleotide triplet which is present at position +3 to +5 of said DNA target sequence from the mouse ROSA26 locus, (g) combining in a single variant, the mutation(s) at positions 26 to 40 and 44 to 77 of two variants from (c) and (d), to obtain a novel homodimeric I-CreI variant which cleaves a sequence wherein (i) the nucleotide triplet at positions −10 to −8 is identical to the nucleotide triplet which is present at positions −10 to −8 of said DNA target sequence from the mouse ROSA26 locus, (ii) the nucleotide triplet at positions +8 to +10 is identical to the reverse complementary sequence of the nucleotide triplet which is present at positions −10 to −8 of said DNA target sequence from the mouse ROSA26 locus, (iii) the nucleotide triplet at positions −5 to −3 is identical to the nucleotide triplet which is present at positions −5 to −3 of said DNA target sequence from the mouse ROSA26 locus and (iv) the nucleotide triplet at positions +3 to +5 is identical to the reverse complementary sequence of the nucleotide triplet which is present at positions −5 to −3 of said DNA target sequence from the mouse ROSA26 locus, and/or (h) combining in a single variant, the mutation(s) at positions 26 to 40 and 44 to 77 of two variants from (e) and (f), to obtain a novel homodimeric I-CreI variant which cleaves a sequence wherein (i) the nucleotide triplet at positions +3 to +5 is identical to the nucleotide triplet which is present at positions +3 to +5 of said DNA target sequence from the mouse ROSA26 locus, (ii) the nucleotide triplet at positions −5 to −3 is identical to the reverse complementary sequence of the nucleotide triplet which is present at positions +3 to +5 of said DNA target sequence from the mouse ROSA26 locus, (iii) the nucleotide triplet at positions +8 to +10 of the I-CreI site has been replaced with the nucleotide triplet which is present at positions +8 to +10 of said DNA target sequence from the mouse ROSA26 locus and (iv) the nucleotide triplet at positions −10 to −8 is identical to the reverse complementary sequence of the nucleotide triplet at positions +8 to +10 of said DNA target sequence from the mouse ROSA26 locus, (i) combining the variants obtained in (g) or (h), or both, to form heterodimers, and (j) selecting or screening, or both, the heterodimers from (i) which are able to cleave said DNA target sequence from the mouse ROSA26 locus.

* * * * *

SEQUENCE LISTING

<160> NUMBER OF SEQ ID NOS: 150

<210> SEQ ID NO 1
<211> LENGTH: 163
<212> TYPE: PRT
<213> ORGANISM: Chlamydomonas reinhardtii

<400> SEQUENCE: 1

Met Asn Thr Lys Tyr Asn Lys Glu Phe Leu Leu Tyr Leu Ala Gly Phe
1               5                   10                  15

Val Asp Gly Asp Gly Ser Ile Ile Ala Gln Ile Lys Pro Asn Gln Ser
            20                  25                  30

Tyr Lys Phe Lys His Gln Leu Ser Leu Ala Phe Gln Val Thr Gln Lys
        35                  40                  45

Thr Gln Arg Arg Trp Phe Leu Asp Lys Leu Val Asp Glu Ile Gly Val
    50                  55                  60

Gly Tyr Val Arg Asp Arg Gly Ser Val Ser Asp Tyr Ile Leu Ser Glu
65                  70                  75                  80

Ile Lys Pro Leu His Asn Phe Leu Thr Gln Leu Gln Pro Phe Leu Lys
                85                  90                  95

Leu Lys Gln Lys Gln Ala Asn Leu Val Leu Lys Ile Ile Trp Arg Leu
            100                 105                 110

Pro Ser Ala Lys Glu Ser Pro Asp Lys Phe Leu Glu Val Cys Thr Trp
        115                 120                 125

Val Asp Gln Ile Ala Ala Leu Asn Asp Ser Lys Thr Arg Lys Thr Thr
    130                 135                 140

Ser Glu Thr Val Arg Ala Val Leu Asp Ser Leu Ser Glu Lys Lys Lys
145                 150                 155                 160

Ser Ser Pro

<210> SEQ ID NO 2
<211> LENGTH: 24
<212> TYPE: DNA
<213> ORGANISM: Artificial Sequence
<220> FEATURE:
<223> OTHER INFORMATION: Description of Artificial Sequence: C1221
    DNA target

<400> SEQUENCE: 2
tcaaaacgtc gtacgacgtt ttga                                         24

<210> SEQ ID NO 3
<211> LENGTH: 13139
<212> TYPE: DNA
<213> ORGANISM: Mus musculus

<400> SEQUENCE: 3
aagcttctca cgtagcaacc agagctccag agccagcagc tgctgccgcc ttgtatactc    60
actcctgtga tccaacacag gagcaacctt ttctttaccc cacccccact tcttaacaca   120
cttttttttg gggggggggg gggaacaagt gctccatgct ggaaggattg gaactatgct   180
tttagaaagg aacaatccta aggtcacttt taaattgagg tctttgattt gaaaatcaac   240
aaataccaaa ttccaaatat tcgttttaat taaaccagca atgtggatat aagcattaag   300
ttttagtttt aaaaggtca attttccaaa cattcagcaa tcatatttaa atttacagct    360
aggaacaaga gccttgggtc atgtcctacc aaagaacata actcaatatt ctacacatga   420
caatctgaat aaccttaaag cctctaatcc cataacaggc cacaaatttt ggacagagaa   480

```
ctaatgatcc tcctgagaaa actggaagaa atccagggaa aagaaattcc tgtgtcctcc    540
aaactcagaa atctctaatt atgtcagtat tctctgcttt agtcctaggt cagattgcac    600
acatctaaaa taacctctta aagttttcct cctagcgacc taaaccatta ttaatatcaa    660
attaaccatc aaaacacttt cctctcaata tgctgcacac aaacctcctc ctggaacctc    720
ctccatctgg atcctcccca atcaaaagta taggtattta acatataagc aaggaagtaa    780
tgtaaacatg accttggtca caaatatgtc atctaaaaac aatttagtca aggtatggag    840
gaaattcgag aacctgaatc tttttaagta ttttgagcac aggaacaatt ggcaaaagga    900
atccaggtat agacaaaacc cagagcccag agctctgggc gaaaaatgag ttgctggtga    960
agacgttaca caagtaacat gagaaagcag aaaatgcagg tcatccacgc accectgacc   1020 caggccagca gggcgggctg cagcatcagt acacaggaga aagatcctta ttcctaagaa   1080
tgagaaaggc aaaggcgccc gatagaataa attagcatag aagggctttt cccaggagtt   1140
aaaactttcc ttctgagcga ttacctacta aaaccagggc ttttgcccac taccatttac   1200
ctaggatctt ggcttgcacg gattcatagg ggcatatccc tccccctctt ctttagagtc   1260
gttcttaaaa gatcgctctc cacgccctag gcagggaaaa cgacaaaatc tggctcaatt   1320
ccaggctaga accctacaaa ttcaacaggg atatcgcaag gatactgggg catacgccac   1380
agggagtcca agaatgtgag gtgggggtgg cgaaggtaat gtctttggtg tgggaaaagc   1440
agcagccatc tgagatagga actggaaaac cagaggagag gcgttcagga agattatgga   1500
ggggaggact gggcccccac gagcgaccag agttgtcaca aggccgcaag aacagggag   1560 gtgggggct caggacaga aaaaaagta tgtgtatttt gagagcaggg ttggggaggcc   1620 tctcctgaaa agggtataaa cgtggagtag gcaatacca gcaaaaagg ggagaccaga   1680 gtaggggag gggaagagtc ctgacccagg gaagacatta aaaggtagt ggggtcgact   1740 agatgaagga gagcctttct ctctgggcaa gagcggtgca atggtgtgta aaggtagctg   1800
agaagacgaa aagggcaagc atcttcctgc taccaggctg gggaggccca ggcccacgac   1860
cccgaggaga gggaacgcag ggagactgag gtgacccttc tttcccccgg ggcccggtcg   1920
tgtggttcgg tgtctctttt ctgttggacc cttaccttga cccaggcgct gccggggcct   1980
gggcccgggc tgcggcgcac ggcactcccg ggaggcagcg agactcgagt taggcccaac   2040
gcggcgccac ggcgtttcct ggccgggaat ggcccgtacc cgtgaggtgg gggtgggggg   2100
cagaaaaggc ggagcgagcc cgagcgggga ggggagggc caggggcgga ggggccggc   2160 actactgtgt tggcggactg gcgggactag ggctgcgtga gtctctgagc gcaggcgggc   2220
ggcggccgcc cctcccccgg cggcggcagc ggcggcagcg gcggcagctc actcagcccg   2280
ctgcccgagc ggaaacgcca ctgaccgcac ggggattccc agtgccggcg ccaggggcac   2340 gcggacacg cccctcccg ccgcgccatt ggcctctccg cccaccgccc cacacttatt   2400
ggccggtgcg ccgccaatca gcggaggctg ccggggccgc ctaaagaaga ggctgtgctt   2460
tggggctccg gctcctcaga gagcctcggc taggtagggg atcggactc tggcgggagg   2520 gcggcttggt gcgtttgcgg ggatgggcgg ccgcggcagg ccctccgagc gtggtggagc   2580
cgttctgtga gacagccggg tacgagtcgt gacgctggaa ggggcaagcg ggtggtgggc   2640
aggaatgcgg tccgccctgc agcaaccgga ggggagggga gaaggagcg gaaaagtctc   2700 caccggacgc ggccatggct cggggggggg ggggcagcgg aggagcgctt ccggccgacg   2760
tctcgtcgct gattggcttc ttttcctccc gccgtgtgtg aaaacacaaa tggcgtgttt   2820
tggttggcgt aaggcgcctg tcagttaacg gcagccgag tgcgcagccg ccggcagcct   2880
```

```
cgctctgccc actgggtggg gcgggaggta ggtggggtga ggcgagctgg acgtgcgggc    2940
gcggtcggcc tctggcgggg cggggagggg gagggagggt cagcgaaagt agctcgcgcg    3000
cgagcggccg cccacccctcc ccttcctctg ggggagtcgt tttacccgcc gccggccggg    3060
cctcgtcgtc tgattggctc tcggggccca gaaaactggc ccttgccatt ggctcgtgtt    3120
cgtgcaagtt gagtccatcc gccgccagc ggggcggcg aggaggcgct cccaggttcc    3180
ggccctcccc tcggcccgc gccgcagagt ctggccgcgc gccctgcgc aacgtggcag    3240 gaagcgcgcg ctggggcgg ggacgggcag tagggctgag cggctgcggg gcgggtgcaa    3300
gcacgtttcc gacttgagtt gcctcaagag gggcgtgctg agccagacct ccatcgcgca    3360
ctccggggag tggagggaag gagcgagggc tcagttgggc tgttttggag gcaggaagca    3420
cttgctctcc caaagtcgct ctgagttgtt atcagtaagg gagctgcagt ggagtaggcg    3480
gggagaaggc cgcacccttc tccggagggg ggaggggagt gttgcaatac ctttctggga    3540
gttctctgct gcctcctggc ttctgaggac cgccctgggc ctgggagaat cccttccccc    3600
tcttccctcg tgatctgcaa ctccagtctt tctagaagat gggcgggagt cttctgggca    3660
ggcttaaagg ctaacctggt gtgtgggcgt tgtcctgcag gggaattgaa caggtgtaaa    3720
attggaggga caagacttcc cacagatttt cggttttgtc gggaagtttt ttaataggg    3780 caaataagga aaatgggagg ataggtagtc atctgggtt ttatgcagca aaactacagg    3840
ttattattgc ttgtgatccg cctcggagta ttttccatcg aggtagatta aagacatgct    3900
cacccgagtt ttatactctc ctgcttgaga tccttactac agtatgaaat tacagtgtcg    3960
cgagttagac tatgtaagca gaattttaat cattttaaa gagcccagta cttcatatcc    4020
atttctcccg ctccttctgc agccttatca aaaggtattt tagaacactc attttagccc    4080
cattttcatt tattatactg gcttatccaa cccctagaca gagcattggc attttcccttt    4140 tcctgatctt agaagtctga tgactcatga aaccagacag attagttaca tacaccacaa    4200
atcgaggctg tagctggggc ctcaacactg cagttctttt ataactcctt agtacacttt    4260
ttgttgatcc tttgccttga tccttaattt tcagtgtcta tcacctctcc cgtcagtggt    4320
gttccacatt tgggcctatt ctcagtccag ggagttttac aacaatagat gtattgagaa    4380
tccaacctaa agcttaactt tccactccca tgaatgcctc tctccttttt ctccatttat    4440
aaactgagct attaaccatt aatggttcca ggtggatgtc tcctcccat attacctgat    4500 gtatcttaca tattgccagg ctgatatttt aagacattaa aagtatatt tcattattga    4560 gccacatggt attgattact gcttactaaa attttgtcat tgtacacatc tgtaaaaggt    4620
ggttcctttt ggaatgcaaa gttcaggtgt tgttgtctt tcctgaccta aggtcttgtg    4680
agcttgtatt ttttctattt aagcagtgct ttctcttgga ctggcttgac tcatggcatt    4740
ctacacgtta ttgctggtct aaatgtgatt ttgccaagct tcttcaggac ctataatttt    4800
gcttgacttg tagccaaaca caagtaaaat gattaagcaa caaatgtatt tgtgaagctt    4860 ggttttagg ttgttgtgtt gtgtgtgctt gtgctctata ataatactat ccaggggctg    4920
gagaggtggc tcggagttca agagcacaga ctgctcttcc agaagtcctg agttcaattc    4980
ccagcaacca catggtggct cacaaccatc tgtaatggga tctgatgccc tcttctggtg    5040
tgtctgaaga ccacaagtgt attcacatta aataaataaa tcctccttct tcttcttttt    5100 tttttttta aagagaatac tgtctccagt agaatttact gaagtaatga aatactttgt    5160
gtttgttcca atatggtagc caataatcaa attactcttt aagcactgga aatgttacca    5220
aggaactaat ttttatttga agtgtaactg tggacagagg agccataact gcagacttgt    5280
```

```
gggatacaga agaccaatgc agactttaat gtcttttctc ttacactaag caataaagaa   5340
ataaaaattg aacttctagt atcctatttg tttaaactgc tagctttact taacttttgt   5400
gcttcatcta tacaaagctg aaagctaagt ctgcagccat tactaaacat gaaagcaagt   5460
aatgataatt ttggatttca aaaatgtagg gccagagttt agccagccag tggtggtgct   5520
tgcctttatg cctttaatcc cagcactctg gaggcagaga caggcagatc tctgagtttg   5580
agcccagcct ggtctacaca tcaagttcta tctaggatag ccaggaatac acacagaaac   5640
cctgttgggg aggggggctc tgagatttca taaaattata attgaagcat tccctaatga   5700
gccactatgg atgtggctaa atccgtctac ctttctgatg agatttgggt attatttttt   5760
ctgtctctgc tgttggttgg gtcttttgac actgtgggct ttctttaaag cctccttcct   5820
gccatgtggt ctcttgtttg ctactaactt cccatggctt aaatggcatg gcttttttgcc   5880 ttctaagggc agctgctgag atttgcagcc tgatttccag ggtggggttg ggaaatcttt   5940
caaacactaa aattgtcctt taattttttt tttaaaaaat gggttatata ataaacctca   6000
taaaatagtt atgaggagtg aggtggacta atattaaatg agtccctccc ctataaaaga   6060
gctattaagg cttttttgtct tatacttaac tttttttta aatgtggtat ctttagaacc   6120
aagggtctta gagttttagt atacagaaac tgttgcatcg cttaatcaga ttttctagtt   6180
tcaaatccag agaatccaaa ttcttcacag ccaaagtcaa attaagaatt tctgactttt   6240
aatgttaatt tgcttactgt gaatataaaa atgatagctt ttcctgaggc agggtctcac   6300
tatgtatctc tgcctgatct gcaacaagat atgtagacta aagttctgcc tgcttttgtc   6360
tcctgaatac taaggttaaa atgtagtaat acttttggaa cttgcaggtc agattctttt   6420 atagggggaca cactaaggga gcttgggtga tagttggtaa aatgtgtttc aagtgatgaa   6480
aacttgaatt attatcaccg caacctactt tttaaaaaaa aaagccaggc ctgttagagc   6540
atgcttaagg gatccctagg acttgctgag cacacaagag tagttacttg gcaggctcct   6600
ggtgagagca tatttcaaaa aacaaggcag acaaccaaga aactacagtt aaggttacct   6660
gtctttaaac catctgcata tacacaggga tattaaaata ttccaaataa tatttcattc   6720
aagttttccc ccatcaaatt gggacatgga tttctccggt gaataggcag agttggaaac   6780
taaacaaatg ttggttttgt gatttgtgaa attgttttca agtgatagtt aaagcccatg   6840
agatacagaa caaagctgct atttcgaggt ctcttggttt atactcagaa gcacttcttt   6900
gggtttccct gcactatcct gatcatgtgc taggcctacc ttaggctgat tgttgttcaa   6960
ataaacttaa gtttcctgtc aggtgatgtc atatgatttc atatatcaag gcaaaacatg   7020
ttatatatgt taaacatttg tacttaatgt gaaagttagg gtctttgtggg tttgattttt   7080 aattttcaaa acctgagcta aataagtcat ttttacatgt cttacatttg gtggaattgt   7140
ataattgtgg tttgcaggca agactctctg acctagtaac cctacctata gagcactttg   7200
ctgggtcaca agtctaggag tcaagcattt caccttgaag ttgagacgtt ttgttagtgt   7260
atactagttt atatgttgga ggacatgttt atccagaaga tattcaggac tattttttgac   7320 tgggctaagg aattgattct gattagcact gttagtgagc attgagtggc ctttaggctt   7380
gaattggagt cacttgtata tctcaaataa tgctggcctt ttttaaaaag cccttgttct   7440
ttatcaccct gttttctaca taattttttgt tcaaagaaat acttgtttgg atctcctttt   7500
gacaacaata gcatgttttc aagccatatt ttttttcctt tttttttttt tttttggttt   7560
ttcgagacag ggtttctctg tatagccctg gctgtcctgg aactcacttt gtagaccagg   7620
ctggcctcga actcagaaat ccgcctgcct ctgcctcctg agtgccggga ttaaaggcgt   7680
```

```
gcaccaccac gcctggctaa gttggatatt ttgttatata actataacca atactaactc   7740
cactgggtgg attttttaatt cagtcagtag tcttaagtgg tctttattgg cccttcatta   7800
aaatctactg ttcactctaa cagaggctgt tggtactagt ggcacttaag caacttccta   7860
cggatatact agcagattaa gggtcaggga tagaaactag tctagcgttt tgtataccta   7920
ccagctttat actaccttgt tctgatagaa atatttcagg acatctagag tgtactataa   7980
ggttgatggt aagcttataa ggaacttgaa agtggagtaa ctactccatt tctctgaggg   8040
gagaattaaa attttttgacc aagtgttgtt gagccactga gaatggtctc agaacataac   8100
ttcttaagga accttcccag attgccctca acactgcacc acatttggtc ctgcttgaac   8160
attgccatgg ctcttaaagt cttaattaag aatattaatt gtgtaattat tgttttttcct   8220
cctttagatc attccttgag gacaggacag tgcttgttta aggctatatt tctgctgtct   8280
gagcagcaac aggtcttcga gatcaacatg atgttcataa tcccaagatg ttgccattta   8340
tgttctcaga agcaagcaga ggcatgatgg tcagtgacag taatgtcact gtgttaaatg   8400
ttgctatgca gtttggatttt ttctaatgta gtgtaggtag aacatatgtg ttctgtatga   8460
attaaactct taagttacac cttgtataat ccatgcaatg tgttatgcaa ttaccatttt   8520
aagtattgta gctttctttg tatgtgagga taaaggtgtt tgtcataaaa tgttttgaac   8580
atttccccaa agttccaaat tataaaacca caacgttaga acttatttat gaacaatggt   8640
tgtagtttca tgcttttaaa atgcttaatt attcaattaa caccgtttgt gttataatat   8700
atataaaact gacatgtaga agtgtttgtc cagaacattt cttaaatgta tactgtcttt   8760
agagagttta atatagcatg tcttttgcaa catactaact tttgtgttgg tgcgagcaat   8820
attgtgtagt cattttgaaa ggagtcattt caatgagtgt cagattgttt tgaatgttat   8880
tgaacatttt aaatgcagac ttgttcgtgt tttagaaagc aaaactgtca gaagctttga   8940
actagaaatt aaaaagctga agtatttcag aagggaaata agctacttgc tgtattagtt   9000
gaaggaaagt gtaatagctt agaaaattta aaaccatata gttgtcattg ctgaatatct   9060
ggcagatgaa aagaaatact cagtggttct tttgagcaat ataacagctt gttatattaa   9120
aaatttttccc cacagatata aactctaatc tataactcat aaatgttaca aatggatgaa   9180
gcttacaaat gtggcttgac ttgtcactgt gcttgttta gttatgtgaa agtttggcaa   9240
taaacctatg tcctaaatag tcaaactgtg gaatgacttt ttaatctatt ggtttgtcta   9300
gaacagttat gttgccattt gccctaatgg tgaaagaaaa agtgggggagt gccttggcac   9360
tgttcatttg tggtgtgaac caaagagggg ggcatgcact tacacttcaa acatcctttt   9420
gaaagactga caagtttggg tcttcacagt tggaattggg catcccttttt gtcagggagg   9480
gagggaggga gggaggctgg cttgttatgc tgacaagtgt gattaaattc aaactttgag   9540
gtaagttgga ggaacttgta cattgttagg agtgtgacaa tttggactct taatgatttg   9600
gtcatacaaa atgaacctag accaacttct ggaagatgta taataaact ccatgttaca   9660
ttgatttcac ctgactaata cttatcccctt atcaattaaa tacagaagat gccagccatc   9720
tgggccttttt aacccagaaa tttagtttca aactcctagg ttagtgttct cactgagcta   9780
catcctgatc tagtcctgaa ataggaccaa ccatcacccc caaaaaaatc tcaaataaga   9840
tttatgctag tgtttcaaaa ttttaggaat aggtaagatt agaaagtttt aaattttgag   9900
aaatggcttc tctagaaaga tgtacatagt gaacactgaa tggctcctaa agagcctaga   9960
aaactggtac tgagcacaca ggactgagag gtctttcttg aaaagcatgt attgcttttac  10020
gtgggtcaca gaaggcaggc aggaagaact tgggctgaaa ctggtgtctt aagtggctaa  10080
```

```
catcttcaca actgatgagc aagaacttta tcctgatgca aaaaccatcc aaacaaacta   10140
agtgaaaggt ggcaatggat cccaggctgc tctagaggag gacttgactt ctcatcccat   10200
cacccacacc agatagctca tagactgcca attaacacca gcttctagcc tccacaggca   10260
cctgcactgg tacacataat ttcacacaaa cacagtaaga agccttccac ctggcatggt   10320
attgcttatc tttagttccc aacacttggg aggcagaggc cagccagggc tatgtgacaa   10380
aaaccttgtc tagaggagaa acttcatagc ttatttccta ttcacgtaac caggttagca   10440
aaatttacca gccagagatg aagctaacag tgtccactat atttgtagtg ttttaagtca   10500 atttttaaa tatacttaat agaattaaag ctatggtgaa ccaagtacaa acctggtgta   10560
ttaacttgag aacttagcat aaaaagtagt tcatttgttc agtaaatatt aaatgcttac   10620
tggcaaagat tatgtcagga acttggtaaa tggtgatgaa acaatcatag ttgtacatct   10680
tggttctgtg atcaccttgg tttgaggtaa aagtggttcc tttgatcaag gatggaattt   10740
taagtttata ttcaatcaat aatgtattat tttgtgattg caaaattgcc tatctagggt   10800
ataaaacctt taaaaatttc ataataccag ttcattctcc agttactaat tccaaaaagc   10860
cactgactat ggtgccaatg tggattctgt tctcaaagga aggattgtct gtgcccttta   10920
ttctaataga aacatcacac tgaaaatcta agctgaaaga agccagactt tcctaaataa   10980
ataactttcc ataagctca aacaaggatt acttttagga ggcactgtta aggaactgat   11040
aagtaatgag gttacttata taatgatagt cccacaagac tatctgagga aaaatcagta   11100
caactcgaaa acagaacaac cagctaggca ggaataacag ggctcccaag tcaggaggtc   11160
tatccaacac ccttttctgt tgagggcccc agacctacat attgtataca acagggagg   11220 tgggtgattt taactctcct gaggtacctt ggtaaatctt tgtcctgagt aagcagtaca   11280
gtgtacagtt tacattttca tttaaagata cattagctcc ctctaccccc taagactgac   11340
aggcactttg ggggtgggga gggctttgga aaataacgct tccatacact aaaagagaaa   11400
tttctttaat taggcttgtt ggttccatac atctactggt gtttctacta cttagtaata   11460
ttataatagt cacacaagca tctttgctct gtttaggttg tatatttatt ttaaggcaga   11520
tgataaaact gtagatctta agggatgctt ctgcttctga gatgatacaa agaatttaga   11580
ccataaaaca gtaggttgca caagcaatag aatatggcct aaagtgttct gacacttaga   11640
agccaagcag tgtaggcttc ttaagaaata ccattacaat caccttgcta gaaatcaagc   11700
attctggagt ggtcaagcag tgtaacctgt actgtaagtt acttttctgc tattttctc   11760 ccaaagcaag ttctttatgc tgatatttcc agtgttagga actacaaata ttaataagtt   11820
gtcttcactc ttttctttac caaggagggt ctcttccttc atcttgatct gaaggatgaa   11880
caaaggcttg agcagtgcgc tttagaagat aaactgcagc atgaaggccc ccgatgttca   11940
cccagactac atggaccttt cgccacacat gtcccattcc agataaggcc tggcacacac   12000
aaaaaacata agtcattagg ctaccagtct gattctaaaa caacctaaaa tcttcccact   12060
taaatgctat gggtggtggg ttggaaagtt gactcagaaa atcacttgct gtttttagag   12120
aggatctggg ttcagtttct gatacattgt ggcttacaac tataactcca gttctagggg   12180
gtccatccaa catcctcttc tgttgagggc accaaataaa tgtattgtgt acaaacaggg   12240
aggtgagtga tttaactctc gtgtatagta ccttggtaaa acatttcttg tcctgagtaa   12300
gcagtacagc tctgcctgtc cctggtctac agacacggct catttcccga aggcaagctg   12360
gatagagatt ccaatttctc ttcttggatc ccatcctata aaagaaggtc aagtttaatc   12420
tattgcaaaa ggtaaatagg tagtttctta catgagacaa gaacaaatct taggtgtgaa   12480
```

```
gcagtcatct tttacaggcc agagcctcta ttctatgcca atgaaggaaa ctgttagtcc    12540
agtgttatag agttagtcca gtgtatagtt ttctatcaga acactttttt tttaaacaac    12600
tgcaacttag cttattgaag acaaaccacg agtagaaatc tgtccaagaa gcaagtgctt    12660
ctcagcctac aatgtggaat aggaccatgt aatggtacag tgagtgaaat gaattatggc    12720 atgttttttct gactgagaag acagtacaat aaaaggtaaa ctcatggtat ttatttaaaa    12780
agaatccaat ttctaccttt ttccaaatgg catatctgtt acaataatat ccacagaagc    12840
agttctcagt gggaggttgc agatatccca ctgaacagca tcaatgggca aaccccaggt    12900
tgtttttctg tggagacaaa ggtaagatat ttcaatatat tttcccaagc taatgagatg    12960
gctcagcaaa taatggtact ggccattaag tctcatgacc tgagcttgat cctcagggac    13020
catgtggtac aaggagagac ctaaatcctt cagttggact tcaatcttct accctcatgt    13080
ccacacacaa ataaatacaa taaaaaacat tctgcagtcg aatttctaaa agggcgaat     13139
```

```
<210> SEQ ID NO 4
<211> LENGTH: 167
<212> TYPE: PRT
<213> ORGANISM: Artificial Sequence
<220> FEATURE:
<223> OTHER INFORMATION: Description of Artificial Sequence: I-CreI N75
      scaffold protein

<400> SEQUENCE: 4
```

Met Ala Asn Thr Lys Tyr Asn Lys Glu Phe Leu Leu Tyr Leu Ala Gly
1               5                   10                  15

Phe Val Asp Gly Asp Gly Ser Ile Ile Ala Gln Ile Lys Pro Asn Gln
            20                  25                  30

Ser Tyr Lys Phe Lys His Gln Leu Ser Leu Thr Phe Gln Val Thr Gln
        35                  40                  45

Lys Thr Gln Arg Arg Trp Phe Leu Asp Lys Leu Val Asp Glu Ile Gly
    50                  55                  60

Val Gly Tyr Val Arg Asp Arg Gly Ser Val Ser Asn Tyr Ile Leu Ser
65                  70                  75                  80

Glu Ile Lys Pro Leu His Asn Phe Leu Thr Gln Leu Gln Pro Phe Leu
                85                  90                  95

Lys Leu Lys Gln Lys Gln Ala Asn Leu Val Leu Lys Ile Ile Glu Gln
            100                 105                 110

Leu Pro Ser Ala Lys Glu Ser Pro Asp Lys Phe Leu Glu Val Cys Thr
        115                 120                 125

Trp Val Asp Gln Ile Ala Ala Leu Asn Asp Ser Lys Thr Arg Lys Thr
    130                 135                 140

Thr Ser Glu Thr Val Arg Ala Val Leu Asp Ser Leu Ser Glu Lys Lys
145                 150                 155                 160

Lys Ser Ser Pro Ala Ala Asp
                165

```
<210> SEQ ID NO 5
<211> LENGTH: 22
<212> TYPE: DNA
<213> ORGANISM: Artificial Sequence
<220> FEATURE:
<223> OTHER INFORMATION: Description of Artificial Sequence: ROSA26
      DNA target

<400> SEQUENCE: 5
cgcccctgcg caacgtggca gg                                              22
```

```
<210> SEQ ID NO 6
<211> LENGTH: 22
<212> TYPE: DNA
<213> ORGANISM: Artificial Sequence
<220> FEATURE:
<223> OTHER INFORMATION: Description of Artificial Sequence: ROSA26
      DNA target

<400> SEQUENCE: 6
ccgcaccctt ctccggaggg gg                                           22

<210> SEQ ID NO 7
<211> LENGTH: 22
<212> TYPE: DNA
<213> ORGANISM: Artificial Sequence
<220> FEATURE:
<223> OTHER INFORMATION: Description of Artificial Sequence: ROSA26
      DNA target

<400> SEQUENCE: 7
tggactggct tgactcatgg ca                                           22

<210> SEQ ID NO 8
<211> LENGTH: 22
<212> TYPE: DNA
<213> ORGANISM: Artificial Sequence
<220> FEATURE:
<223> OTHER INFORMATION: Description of Artificial Sequence: ROSA26
      DNA target

<400> SEQUENCE: 8
ccagcctggt ctacacatca ag                                           22

<210> SEQ ID NO 9
<211> LENGTH: 22
<212> TYPE: DNA
<213> ORGANISM: Artificial Sequence
<220> FEATURE:
<223> OTHER INFORMATION: Description of Artificial Sequence: ROSA26
      DNA target

<400> SEQUENCE: 9
ctatctagga tagccaggaa ta                                           22

<210> SEQ ID NO 10
<211> LENGTH: 22
<212> TYPE: DNA
<213> ORGANISM: Artificial Sequence
<220> FEATURE:
<223> OTHER INFORMATION: Description of Artificial Sequence: ROSA26
      DNA target

<400> SEQUENCE: 10
cagcctgatt tccagggtgg gg                                           22

<210> SEQ ID NO 11
<211> LENGTH: 22
<212> TYPE: DNA
<213> ORGANISM: Artificial Sequence
<220> FEATURE:
<223> OTHER INFORMATION: Description of Artificial Sequence: ROSA26
      DNA target

<400> SEQUENCE: 11
taaacctcat aaaatagtta tg                                           22

<210> SEQ ID NO 12
```

```
<211> LENGTH: 22
<212> TYPE: DNA
<213> ORGANISM: Artificial Sequence
<220> FEATURE:
<223> OTHER INFORMATION: Description of Artificial Sequence: ROSA26
      DNA target

<400> SEQUENCE: 12
tcagattctt ttatagggga ca                                           22

<210> SEQ ID NO 13
<211> LENGTH: 22
<212> TYPE: DNA
<213> ORGANISM: Artificial Sequence
<220> FEATURE:
<223> OTHER INFORMATION: Description of Artificial Sequence: ROSA26
      DNA target

<400> SEQUENCE: 13
ttgtatatct caaataatgc tg                                           22

<210> SEQ ID NO 14
<211> LENGTH: 22
<212> TYPE: DNA
<213> ORGANISM: Artificial Sequence
<220> FEATURE:
<223> OTHER INFORMATION: Description of Artificial Sequence: ROSA
      DNA target

<400> SEQUENCE: 14
tgagccactg agaatggtct ca                                           22

<210> SEQ ID NO 15
<211> LENGTH: 22
<212> TYPE: DNA
<213> ORGANISM: Artificial Sequence
<220> FEATURE:
<223> OTHER INFORMATION: Description of Artificial Sequence: ROSA26
      DNA target

<400> SEQUENCE: 15
caacatgatg ttcataatcc ca                                           22

<210> SEQ ID NO 16
<211> LENGTH: 22
<212> TYPE: DNA
<213> ORGANISM: Artificial Sequence
<220> FEATURE:
<223> OTHER INFORMATION: Description of Artificial Sequence: ROSA26
      DNA target

<400> SEQUENCE: 16
ttaaatgttg ctatgcagtt tg                                           22

<210> SEQ ID NO 17
<211> LENGTH: 22
<212> TYPE: DNA
<213> ORGANISM: Artificial Sequence
<220> FEATURE:
<223> OTHER INFORMATION: Description of Artificial Sequence: ROSA26
      DNA target

<400> SEQUENCE: 17
ttccccaaag ttccaaatta ta                                           22

<210> SEQ ID NO 18
<211> LENGTH: 22
<212> TYPE: DNA
```

```
<213> ORGANISM: Artificial Sequence
<220> FEATURE:
<223> OTHER INFORMATION: Description of Artificial Sequence: ROSA26
      DNA target

<400> SEQUENCE: 18
taacaccgtt tgtgttataa ta                                              22

<210> SEQ ID NO 19
<211> LENGTH: 22
<212> TYPE: DNA
<213> ORGANISM: Artificial Sequence
<220> FEATURE:
<223> OTHER INFORMATION: Description of Artificial Sequence: ROSA26
      DNA target

<400> SEQUENCE: 19
tatactgtct ttagagagtt ta                                              22

<210> SEQ ID NO 20
<211> LENGTH: 22
<212> TYPE: DNA
<213> ORGANISM: Artificial Sequence
<220> FEATURE:
<223> OTHER INFORMATION: Description of Artificial Sequence: ROSA
      DNA target

<400> SEQUENCE: 20
tgtaatagct tagaaaattt aa                                              22

<210> SEQ ID NO 21
<211> LENGTH: 22
<212> TYPE: DNA
<213> ORGANISM: Artificial Sequence
<220> FEATURE:
<223> OTHER INFORMATION: Description of Artificial Sequence: ROSA26
      DNA target

<400> SEQUENCE: 21
tttaatctat tggtttgtct ag                                              22

<210> SEQ ID NO 22
<211> LENGTH: 22
<212> TYPE: DNA
<213> ORGANISM: Artificial Sequence
<220> FEATURE:
<223> OTHER INFORMATION: Description of Artificial Sequence: ROSA26
      DNA target

<400> SEQUENCE: 22
ttgtacattg ttaggagtgt ga                                              22

<210> SEQ ID NO 23
<211> LENGTH: 22
<212> TYPE: DNA
<213> ORGANISM: Artificial Sequence
<220> FEATURE:
<223> OTHER INFORMATION: Description of Artificial Sequence: ROSA26
      DNA target

<400> SEQUENCE: 23
tgcactggta cacataattt ca                                              22

<210> SEQ ID NO 24
<211> LENGTH: 22
<212> TYPE: DNA
<213> ORGANISM: Artificial Sequence
<220> FEATURE:
```

```
<223> OTHER INFORMATION: Description of Artificial Sequence: ROSA26
      DNA target

<400> SEQUENCE: 24
tgagatgata caaagaattt ag                                              22

<210> SEQ ID NO 25
<211> LENGTH: 22
<212> TYPE: DNA
<213> ORGANISM: Artificial Sequence
<220> FEATURE:
<223> OTHER INFORMATION: Description of Artificial Sequence: ROSA26
      DNA target

<400> SEQUENCE: 25
ccatcctata aaagaaggtc aa                                              22

<210> SEQ ID NO 26
<211> LENGTH: 22
<212> TYPE: DNA
<213> ORGANISM: Artificial Sequence
<220> FEATURE:
<223> OTHER INFORMATION: Description of Artificial Sequence: ROSA26
      DNA target

<400> SEQUENCE: 26
tttaatctat tgcaaaaggt aa                                              22

<210> SEQ ID NO 27
<211> LENGTH: 22
<212> TYPE: DNA
<213> ORGANISM: Artificial Sequence
<220> FEATURE:
<223> OTHER INFORMATION: Description of Artificial Sequence: ROSA26
      DNA target

<400> SEQUENCE: 27
tagtccagtg ttatagagtt ag                                              22

<210> SEQ ID NO 28
<211> LENGTH: 22
<212> TYPE: DNA
<213> ORGANISM: Artificial Sequence
<220> FEATURE:
<223> OTHER INFORMATION: Description of Artificial Sequence: ROSA26
      DNA target

<400> SEQUENCE: 28 ttctacctttt ttccaaatgg ca                                             22

<210> SEQ ID NO 29
<211> LENGTH: 22
<212> TYPE: DNA
<213> ORGANISM: Artificial Sequence
<220> FEATURE:
<223> OTHER INFORMATION: Description of Artificial Sequence: ROSA26
      DNA target

<400> SEQUENCE: 29
ttttctgtgg agacaaaggt aa                                              22

<210> SEQ ID NO 30
<211> LENGTH: 22
<212> TYPE: DNA
<213> ORGANISM: Artificial Sequence
<220> FEATURE:
<223> OTHER INFORMATION: Description of Artificial Sequence: ROSA26
      DNA target
```

```
<400> SEQUENCE: 30
tgagatggct cagcaaataa tg                                              22

<210> SEQ ID NO 31
<211> LENGTH: 24
<212> TYPE: DNA
<213> ORGANISM: Artificial Sequence
<220> FEATURE:
<223> OTHER INFORMATION: Description of Artificial Sequence: 10GGG_P
      DNA target

<400> SEQUENCE: 31
tcgggacgtc gtacgacgtc ccga                                            24

<210> SEQ ID NO 32
<211> LENGTH: 24
<212> TYPE: DNA
<213> ORGANISM: Artificial Sequence
<220> FEATURE:
<223> OTHER INFORMATION: Description of Artificial Sequence: 5GAT_P
      DNA target

<400> SEQUENCE: 32
tcaaaacgat gtacatcgtt ttga                                            24

<210> SEQ ID NO 33
<211> LENGTH: 24
<212> TYPE: DNA
<213> ORGANISM: Artificial Sequence
<220> FEATURE:
<223> OTHER INFORMATION: Description of Artificial Sequence: 5TAT_P
      DNA target

<400> SEQUENCE: 33
tcaaaactat gtacatagtt ttga                                            24

<210> SEQ ID NO 34
<211> LENGTH: 22
<212> TYPE: DNA
<213> ORGANISM: Artificial Sequence
<220> FEATURE:
<223> OTHER INFORMATION: Description of Artificial Sequence: rosa1.2
      DNA target

<400> SEQUENCE: 34
caacatgatg tacataatcc ca                                              22

<210> SEQ ID NO 35
<211> LENGTH: 22
<212> TYPE: DNA
<213> ORGANISM: Artificial Sequence
<220> FEATURE:
<223> OTHER INFORMATION: Description of Artificial Sequence: rosa1.3
      DNA target

<400> SEQUENCE: 35
caacatgatg tacatcatgt tg                                              22

<210> SEQ ID NO 36
<211> LENGTH: 22
<212> TYPE: DNA
<213> ORGANISM: Artificial Sequence
<220> FEATURE:
<223> OTHER INFORMATION: Description of Artificial Sequence: rosa1.4
      DNA target

<400> SEQUENCE: 36
```

```
tgggattatg tacataatcc ca                                              22
```

<210> SEQ ID NO 37
<211> LENGTH: 50
<212> TYPE: DNA
<213> ORGANISM: Artificial Sequence
<220> FEATURE:
<223> OTHER INFORMATION: Description of Artificial Sequence: target
      oligonucleotide

<400> SEQUENCE: 37

```
tggcatacaa gtttcaacat gatgtacatc atgttgacaa tcgtctgtca              50
```

<210> SEQ ID NO 38
<211> LENGTH: 167
<212> TYPE: PRT
<213> ORGANISM: Artificial Sequence
<220> FEATURE:
<223> OTHER INFORMATION: Description of Artificial Sequence: m1
      variant

<400> SEQUENCE: 38

```
Met Ala Asn Thr Lys Tyr Asn Lys Glu Phe Leu Leu Tyr Leu Ala Gly
1               5                   10                  15

Phe Val Asp Gly Asp Gly Ser Ile Val Ala Gln Ile Lys Pro Asn Gln
            20                  25                  30

Ser Tyr Lys Phe Lys His Gln Leu Ser Leu Thr Phe Tyr Val Thr Gln
        35                  40                  45

Lys Thr Gln Arg Arg Trp Phe Leu Asp Lys Leu Val Asp Glu Ile Gly
    50                  55                  60

Val Gly Tyr Val Arg Asp Ser Gly Ser Val Ser Tyr Tyr Ile Leu Ser
65                  70                  75                  80

Glu Ile Lys Pro Leu His Asn Phe Leu Thr Gln Leu Gln Pro Phe Leu
                85                  90                  95

Lys Leu Lys Gln Lys Gln Ala Asn Leu Val Leu Lys Ile Ile Glu Gln
            100                 105                 110

Leu Pro Ser Ala Lys Glu Ser Pro Asp Lys Phe Leu Glu Val Cys Thr
        115                 120                 125

Trp Val Asp Gln Ile Ala Ala Leu Asn Asp Ser Lys Thr Arg Lys Thr
    130                 135                 140

Thr Ser Glu Thr Val Arg Ala Val Leu Asp Ser Leu Ser Glu Lys Lys
145                 150                 155                 160

Lys Ser Ser Pro Ala Ala Asp
                165
```

<210> SEQ ID NO 39
<211> LENGTH: 167
<212> TYPE: PRT
<213> ORGANISM: Artificial Sequence
<220> FEATURE:
<223> OTHER INFORMATION: Description of Artificial Sequence: m2
      variant

<400> SEQUENCE: 39

```
Met Ala Asn Thr Lys Tyr Asn Lys Glu Phe Leu Leu Tyr Leu Ala Gly
1               5                   10                  15

Phe Val Asp Gly Asp Gly Ser Ile Val Ala Gln Ile Lys Pro Asn Gln
            20                  25                  30

Ser Tyr Lys Phe Lys His Gln Leu Ser Leu Thr Phe Tyr Val Thr Gln
        35                  40                  45
```

```
Lys Thr Gln Arg Arg Trp Phe Leu Asp Lys Leu Val Asp Glu Ile Gly
        50                  55                  60

Val Gly Tyr Val Arg Asp Ser Gly Ser Val Ser Asn Tyr Ile Leu Ser
 65                  70                  75                  80

Glu Ile Lys Pro Leu His Asn Phe Leu Thr Gln Leu Gln Pro Phe Leu
                85                  90                  95

Lys Leu Lys Gln Lys Gln Ala Asn Leu Val Leu Lys Ile Ile Glu Gln
                100                 105                 110

Leu Pro Ser Ala Lys Glu Ser Pro Asp Lys Phe Leu Glu Val Cys Thr
            115                 120                 125

Trp Val Asp Gln Ile Ala Ala Leu Asn Asp Ser Lys Thr Arg Lys Thr
        130                 135                 140

Thr Ser Glu Thr Val Arg Ala Val Leu Asp Ser Leu Ser Glu Lys Lys
145                 150                 155                 160

Lys Ser Ser Pro Ala Ala Asp
                165

<210> SEQ ID NO 40
<211> LENGTH: 167
<212> TYPE: PRT
<213> ORGANISM: Artificial Sequence
<220> FEATURE:
<223> OTHER INFORMATION: Description of Artificial Sequence: m3
      variant

<400> SEQUENCE: 40

Met Ala Asn Thr Lys Tyr Asn Lys Glu Phe Leu Leu Tyr Leu Ala Gly
 1               5                  10                  15

Phe Val Asp Gly Asp Gly Ser Ile Val Ala Gln Ile Lys Pro Asn Gln
                20                  25                  30

Ser Tyr Lys Phe Lys His Gln Leu Ser Leu Thr Phe Tyr Val Thr Gln
            35                  40                  45

Lys Thr Gln Arg Arg Trp Phe Leu Asp Lys Leu Val Asp Glu Ile Gly
        50                  55                  60

Val Gly Tyr Val Asp Asp Ser Gly Ser Val Ser Arg Tyr Arg Leu Ser
 65                  70                  75                  80

Glu Ile Lys Pro Leu His Asn Phe Leu Thr Gln Leu Gln Pro Phe Leu
                85                  90                  95

Lys Leu Lys Gln Lys Gln Ala Asn Leu Val Leu Lys Ile Ile Glu Gln
                100                 105                 110

Leu Pro Ser Ala Lys Glu Ser Pro Asp Lys Phe Leu Glu Val Cys Thr
            115                 120                 125

Trp Val Asp Gln Ile Ala Ala Leu Asn Asp Ser Lys Thr Arg Lys Thr
        130                 135                 140

Thr Ser Glu Thr Val Arg Ala Val Leu Asp Ser Leu Ser Glu Lys Lys
145                 150                 155                 160

Lys Ser Ser Pro Ala Ala Asp
                165

<210> SEQ ID NO 41
<211> LENGTH: 167
<212> TYPE: PRT
<213> ORGANISM: Artificial Sequence
<220> FEATURE:
<223> OTHER INFORMATION: Description of Artificial Sequence: m4
      variant

<400> SEQUENCE: 41

Met Ala Asn Thr Lys Tyr Asn Lys Glu Phe Leu Leu Tyr Leu Ala Gly
```

```
                1               5              10              15

Phe Val Asp Gly Asp Gly Ser Ile Ile Ala Gln Ile Lys Pro Asn Gln
                20              25              30

Ser Tyr Lys Phe Lys His Gln Leu Ser Leu Thr Phe Thr Val Thr Gln
                35              40              45

Lys Thr Gln Arg Arg Trp Phe Leu Asp Lys Leu Val Asp Glu Ile Gly
        50              55              60

Val Gly Tyr Val Tyr Asp Ser Gly Ser Val Ser Tyr Tyr Arg Leu Ser
65              70              75              80

Glu Ile Lys Pro Leu His Asn Phe Leu Thr Gln Leu Gln Pro Phe Leu
                85              90              95

Lys Leu Lys Gln Lys Gln Ala Asn Leu Val Leu Lys Ile Ile Glu Gln
                100             105             110

Leu Pro Ser Ala Lys Glu Ser Pro Asp Lys Phe Leu Glu Val Cys Thr
                115             120             125

Trp Val Asp Gln Ile Ala Ala Leu Asn Asp Ser Lys Thr Arg Lys Thr
        130             135             140

Thr Ser Glu Thr Val Arg Ala Val Leu Asp Ser Leu Ser Glu Lys Lys
145             150             155             160

Lys Ser Ser Pro Ala Ala Asp
                165

<210> SEQ ID NO 42
<211> LENGTH: 167
<212> TYPE: PRT
<213> ORGANISM: Artificial Sequence
<220> FEATURE:
<223> OTHER INFORMATION: Description of Artificial Sequence:  m5
      variant

<400> SEQUENCE: 42

Met Ala Asn Thr Lys Tyr Asn Lys Glu Phe Leu Leu Tyr Leu Ala Gly
1               5               10              15

Phe Val Asp Gly Asp Gly Ser Ile Val Ala Gln Ile Lys Pro Asn Gln
                20              25              30

Ser Tyr Lys Phe Lys His Gln Leu Ser Leu Thr Phe Tyr Val Thr Gln
                35              40              45

Lys Thr Gln Arg Arg Trp Phe Leu Asp Lys Leu Val Asp Glu Ile Gly
        50              55              60

Val Gly Tyr Val Arg Asp Ser Gly Ser Val Ser Tyr Tyr Gln Leu Ser
65              70              75              80

Glu Ile Lys Pro Leu His Asn Phe Leu Thr Gln Leu Gln Pro Phe Leu
                85              90              95

Lys Leu Lys Gln Lys Gln Ala Asn Leu Val Leu Lys Ile Ile Glu Gln
                100             105             110

Leu Pro Ser Ala Lys Glu Ser Pro Asp Lys Phe Leu Glu Val Cys Thr
                115             120             125

Trp Val Asp Gln Ile Ala Ala Leu Asn Asp Ser Lys Thr Arg Lys Thr
        130             135             140

Thr Ser Glu Thr Val Arg Ala Val Leu Asp Ser Leu Ser Glu Lys Lys
145             150             155             160

Lys Ser Ser Pro Ala Ala Asp
                165

<210> SEQ ID NO 43
<211> LENGTH: 167
<212> TYPE: PRT
```

-continued

```
<213> ORGANISM: Artificial Sequence
<220> FEATURE:
<223> OTHER INFORMATION: Description of Artificial Sequence: m6
      variant

<400> SEQUENCE: 43

Met Ala Asn Thr Lys Tyr Asn Lys Glu Phe Leu Leu Tyr Leu Ala Gly
1               5                   10                  15

Phe Val Asp Gly Asp Gly Ser Ile Val Ala Gln Ile Lys Pro Asn Gln
            20                  25                  30

Ser Tyr Lys Phe Lys His Gln Leu Ser Leu Thr Phe Tyr Val Thr Gln
        35                  40                  45

Lys Thr Gln Arg Arg Trp Phe Leu Asp Lys Leu Val Asp Glu Ile Gly
    50                  55                  60

Val Gly Tyr Val Tyr Asp Ser Gly Ser Val Ser Tyr Tyr Arg Leu Ser
65                  70                  75                  80

Glu Ile Lys Pro Leu His Asn Phe Leu Thr Gln Leu Gln Pro Phe Leu
                85                  90                  95

Lys Leu Lys Gln Lys Gln Ala Asn Leu Val Leu Lys Ile Ile Glu Gln
            100                 105                 110

Leu Pro Ser Ala Lys Glu Ser Pro Asp Lys Phe Leu Glu Val Cys Thr
        115                 120                 125

Trp Val Asp Gln Ile Ala Ala Leu Asn Asp Ser Lys Thr Arg Lys Thr
    130                 135                 140

Thr Ser Glu Thr Val Arg Ala Val Leu Asp Ser Leu Ser Glu Lys Lys
145                 150                 155                 160

Lys Ser Ser Pro Ala Ala Asp
                165

<210> SEQ ID NO 44
<211> LENGTH: 167
<212> TYPE: PRT
<213> ORGANISM: Artificial Sequence
<220> FEATURE:
<223> OTHER INFORMATION: Description of Artificial Sequence: m7
      variant

<400> SEQUENCE: 44

Met Ala Asn Thr Lys Tyr Asn Lys Glu Phe Leu Leu Tyr Leu Ala Gly
1               5                   10                  15

Phe Val Asp Gly Asp Gly Ser Ile Val Ala Gln Ile Lys Pro Asn Gln
            20                  25                  30

Ser Tyr Lys Phe Lys His Gln Leu Ser Leu Thr Phe Tyr Val Thr Gln
        35                  40                  45

Lys Thr Gln Arg Arg Trp Phe Leu Asp Lys Leu Val Asp Glu Ile Gly
    50                  55                  60

Val Gly Tyr Val Tyr Asp Ser Gly Ser Val Ser Arg Tyr Ala Leu Ser
65                  70                  75                  80

Glu Ile Lys Pro Leu His Asn Phe Leu Thr Gln Leu Gln Pro Phe Leu
                85                  90                  95

Lys Leu Lys Gln Lys Gln Ala Asn Leu Val Leu Lys Ile Ile Glu Gln
            100                 105                 110

Leu Pro Ser Ala Lys Glu Ser Pro Asp Lys Phe Leu Glu Val Cys Thr
        115                 120                 125

Trp Val Asp Gln Ile Ala Ala Leu Asn Asp Ser Lys Thr Arg Lys Thr
    130                 135                 140

Thr Ser Glu Thr Val Arg Ala Val Leu Asp Ser Leu Ser Glu Lys Lys
145                 150                 155                 160
```

```
Lys Ser Ser Pro Ala Ala Asp
            165

<210> SEQ ID NO 45
<211> LENGTH: 167
<212> TYPE: PRT
<213> ORGANISM: Artificial Sequence
<220> FEATURE:
<223> OTHER INFORMATION: Description of Artificial Sequence: m8
      variant

<400> SEQUENCE: 45

Met Ala Asn Thr Lys Tyr Asn Lys Glu Phe Leu Leu Tyr Leu Ala Gly
1               5                  10                  15

Phe Val Asp Gly Asp Gly Ser Ile Val Ala Gln Ile Lys Pro Asn Gln
            20                  25                  30

Ser Tyr Lys Phe Lys His Gln Leu Ser Leu Thr Phe Tyr Val Thr Gln
        35                  40                  45

Lys Thr Gln Arg Arg Trp Phe Leu Asp Lys Leu Val Asp Glu Ile Gly
    50                  55                  60

Val Gly Tyr Val Arg Asp Ser Gly Ser Val Ser Asn Tyr Val Leu Ser
65                  70                  75                  80

Glu Ile Lys Pro Leu His Asn Phe Leu Thr Gln Leu Gln Pro Phe Leu
                85                  90                  95

Lys Leu Lys Gln Lys Gln Ala Asn Leu Val Leu Lys Ile Ile Glu Gln
            100                 105                 110

Leu Pro Ser Ala Lys Glu Ser Pro Asp Lys Phe Leu Glu Val Cys Thr
        115                 120                 125

Trp Val Asp Gln Ile Ala Ala Leu Asn Asp Ser Lys Thr Arg Lys Thr
    130                 135                 140

Thr Ser Glu Thr Val Arg Ala Val Leu Asp Ser Leu Ser Glu Lys Lys
145                 150                 155                 160

Lys Ser Ser Pro Ala Ala Asp
            165

<210> SEQ ID NO 46
<211> LENGTH: 167
<212> TYPE: PRT
<213> ORGANISM: Artificial Sequence
<220> FEATURE:
<223> OTHER INFORMATION: Description of Artificial Sequence: m9
      variant

<400> SEQUENCE: 46

Met Ala Asn Thr Lys Tyr Asn Lys Glu Phe Leu Leu Tyr Leu Ala Gly
1               5                  10                  15

Phe Val Asp Gly Asp Gly Ser Ile Val Ala Gln Ile Lys Pro Asn Gln
            20                  25                  30

Ser Tyr Lys Phe Lys His Gln Leu Ser Leu Thr Phe Asn Val Thr Gln
        35                  40                  45

Lys Thr Gln Arg Arg Trp Phe Leu Asp Lys Leu Val Asp Glu Ile Gly
    50                  55                  60

Val Gly Tyr Val Tyr Asp Ser Gly Ser Val Ser Tyr Tyr Arg Leu Ser
65                  70                  75                  80

Glu Ile Lys Pro Leu His Asn Phe Leu Thr Gln Leu Gln Pro Phe Leu
                85                  90                  95

Lys Leu Lys Gln Lys Gln Ala Asn Leu Val Leu Lys Ile Ile Glu Gln
            100                 105                 110
```

```
Leu Pro Ser Ala Lys Glu Ser Pro Asp Lys Phe Leu Glu Val Cys Thr
            115                 120                 125

Trp Val Asp Gln Ile Ala Ala Leu Asn Asp Ser Lys Thr Arg Lys Thr
    130                 135                 140

Thr Ser Glu Thr Val Arg Ala Val Leu Asp Ser Leu Ser Glu Lys Lys
145                 150                 155                 160

Lys Ser Ser Pro Ala Ala Asp
            165

<210> SEQ ID NO 47
<211> LENGTH: 167
<212> TYPE: PRT
<213> ORGANISM: Artificial Sequence
<220> FEATURE:
<223> OTHER INFORMATION: Description of Artificial Sequence: m10
      variant

<400> SEQUENCE: 47

Met Ala Asn Thr Lys Tyr Asn Lys Glu Phe Leu Leu Tyr Leu Ala Gly
1               5                  10                  15

Phe Val Asp Gly Asp Gly Ser Ile Val Ala Gln Ile Lys Pro Asn Gln
            20                  25                  30

Ser Tyr Lys Phe Lys His Gln Leu Ser Leu Thr Phe Asn Val Thr Gln
        35                  40                  45

Lys Thr Gln Arg Arg Trp Phe Leu Asp Lys Leu Val Asp Glu Ile Gly
    50                  55                  60

Val Gly Tyr Val Tyr Asp Ser Gly Ser Val Ser Tyr Tyr Arg Leu Ser
65                  70                  75                  80

Glu Ile Thr Pro Leu His Asn Phe Leu Thr Gln Leu Gln Pro Phe Leu
                85                  90                  95

Lys Leu Lys Gln Lys Gln Ala Asn Leu Val Leu Lys Ile Ile Glu Gln
            100                 105                 110

Leu Pro Ser Ala Lys Glu Ser Pro Asp Lys Phe Leu Glu Val Cys Thr
            115                 120                 125

Trp Val Asp Gln Ile Ala Ala Leu Asn Asp Ser Lys Thr Arg Lys Thr
    130                 135                 140

Thr Ser Glu Thr Val Arg Ala Val Leu Asp Ser Leu Ser Glu Lys Lys
145                 150                 155                 160

Lys Ser Ser Pro Ala Ala Asp
            165

<210> SEQ ID NO 48
<211> LENGTH: 167
<212> TYPE: PRT
<213> ORGANISM: Artificial Sequence
<220> FEATURE:
<223> OTHER INFORMATION: Description of Artificial Sequence:  m11
      variant

<400> SEQUENCE: 48

Met Ala Asn Thr Lys Tyr Asn Lys Glu Phe Leu Leu Tyr Leu Ala Gly
1               5                  10                  15

Phe Val Asp Gly Asp Gly Ser Ile Val Ala Gln Ile Lys Pro Asn Gln
            20                  25                  30

Ser Tyr Lys Phe Lys His Gln Leu Ser Leu Thr Phe Tyr Val Thr Gln
        35                  40                  45

Lys Thr Gln Arg Arg Trp Phe Leu Asp Lys Leu Val Asp Glu Ile Gly
    50                  55                  60

Val Gly Tyr Val Ser Asp Ser Gly Ser Val Ser Arg Tyr Val Leu Ser
```

```
                65                  70                  75                  80
Glu Ile Lys Pro Leu His Asn Phe Leu Thr Gln Leu Gln Pro Phe Leu
                85                  90                  95

Lys Leu Lys Gln Lys Gln Ala Asn Leu Val Leu Lys Ile Ile Glu Gln
            100                 105                 110

Leu Pro Ser Ala Lys Glu Ser Pro Asp Lys Phe Leu Glu Val Cys Thr
        115                 120                 125

Trp Val Asp Gln Ile Ala Ala Leu Asn Asp Ser Lys Thr Arg Lys Thr
    130                 135                 140

Thr Ser Glu Thr Val Arg Ala Val Leu Asp Ser Leu Ser Glu Lys Lys
145                 150                 155                 160

Lys Ser Ser Pro Ala Ala Asp
                165

<210> SEQ ID NO 49
<211> LENGTH: 167
<212> TYPE: PRT
<213> ORGANISM: Artificial Sequence
<220> FEATURE:
<223> OTHER INFORMATION: Description of Artificial Sequence: m12
      variant

<400> SEQUENCE: 49

Met Ala Asn Thr Lys Tyr Asn Lys Glu Phe Leu Leu Tyr Leu Ala Gly
1               5                   10                  15

Phe Val Asp Gly Asp Gly Ser Ile Val Ala Gln Ile Lys Pro Asn Gln
            20                  25                  30

Ser Tyr Lys Phe Lys His Gln Leu Ser Leu Thr Phe Tyr Val Thr Gln
        35                  40                  45

Lys Thr Gln Arg Arg Trp Phe Leu Asp Lys Leu Val Asp Glu Ile Gly
    50                  55                  60

Val Gly Tyr Val Asn Asp Ser Gly Ser Val Ser Arg Tyr Ile Leu Ser
65                  70                  75                  80

Glu Ile Lys Pro Leu His Asn Phe Leu Thr Gln Leu Gln Pro Phe Leu
                85                  90                  95

Lys Leu Lys Gln Lys Gln Ala Asn Leu Val Leu Lys Ile Ile Glu Gln
            100                 105                 110

Leu Pro Ser Ala Lys Glu Ser Pro Asp Lys Phe Leu Glu Val Cys Thr
        115                 120                 125

Trp Val Asp Gln Ile Ala Ala Leu Asn Asp Ser Lys Thr Arg Lys Thr
    130                 135                 140

Thr Ser Glu Thr Val Arg Ala Val Leu Asp Ser Leu Ser Glu Lys Lys
145                 150                 155                 160

Lys Ser Ser Pro Ala Ala Asp
                165

<210> SEQ ID NO 50
<211> LENGTH: 167
<212> TYPE: PRT
<213> ORGANISM: Artificial Sequence
<220> FEATURE:
<223> OTHER INFORMATION: Description of Artificial Sequence: m13
      variant

<400> SEQUENCE: 50

Met Ala Asn Thr Lys Tyr Asn Lys Glu Phe Leu Leu Tyr Leu Ala Gly
1               5                   10                  15

Phe Val Asp Gly Asp Gly Ser Ile Val Ala Gln Ile Lys Pro Asn Gln
            20                  25                  30
```

Ser Tyr Lys Phe Lys His Gln Leu Ser Leu Thr Phe Tyr Val Thr Gln
            35                  40                  45

Lys Thr Gln Arg Arg Trp Phe Leu Asp Lys Leu Val Asp Glu Ile Gly
 50                  55                  60

Val Gly Tyr Val Ser Asp Ser Gly Ser Val Arg Tyr Ile Leu Ser
 65                  70                  75                  80

Glu Ile Lys Pro Leu His Asn Phe Leu Thr Gln Leu Gln Pro Phe Leu
                 85                  90                  95

Lys Leu Lys Gln Lys Gln Ala Asn Leu Val Leu Lys Ile Ile Glu Gln
                100                 105                 110

Leu Pro Ser Ala Lys Glu Ser Pro Asp Lys Phe Leu Glu Val Cys Thr
                115                 120                 125

Trp Val Asp Gln Ile Ala Ala Leu Asn Asp Ser Lys Thr Arg Lys Thr
                130                 135                 140

Thr Ser Glu Thr Val Arg Ala Val Leu Asp Ser Leu Ser Glu Lys Lys
145                 150                 155                 160

Lys Ser Ser Pro Ala Ala Asp
                165

<210> SEQ ID NO 51
<211> LENGTH: 167
<212> TYPE: PRT
<213> ORGANISM: Artificial Sequence
<220> FEATURE:
<223> OTHER INFORMATION: Description of Artificial Sequence: m14
      variant

<400> SEQUENCE: 51

Met Ala Asn Thr Lys Tyr Asn Lys Glu Phe Leu Leu Tyr Leu Ala Gly
 1               5                  10                  15

Phe Val Asp Gly Asp Gly Ser Ile Val Ala Gln Ile Lys Pro Asn Gln
                20                  25                  30

Ser Tyr Lys Phe Lys His Gln Leu Ser Leu Thr Phe Tyr Val Thr Gln
            35                  40                  45

Lys Thr Gln Arg Arg Trp Phe Leu Asp Lys Leu Val Asp Glu Ile Gly
 50                  55                  60

Val Gly Tyr Val Arg Asp Ser Gly Ser Val Ser Gln Tyr Ile Leu Ser
 65                  70                  75                  80

Glu Ile Lys Pro Leu His Asn Phe Leu Thr Gln Leu Gln Pro Phe Leu
                 85                  90                  95

Lys Leu Lys Gln Lys Gln Ala Asn Leu Val Leu Lys Ile Ile Glu Gln
                100                 105                 110

Leu Pro Ser Ala Lys Glu Ser Pro Asp Lys Phe Leu Glu Val Cys Thr
                115                 120                 125

Trp Val Asp Gln Ile Ala Ala Leu Asn Asp Ser Lys Thr Arg Lys Thr
                130                 135                 140

Thr Ser Glu Thr Val Arg Ala Val Leu Asp Ser Leu Ser Glu Lys Lys
145                 150                 155                 160

Lys Ser Ser Pro Ala Ala Asp
                165

<210> SEQ ID NO 52
<211> LENGTH: 167
<212> TYPE: PRT
<213> ORGANISM: Artificial Sequence
<220> FEATURE:
<223> OTHER INFORMATION: Description of Artificial Sequence: m15
      variant

<400> SEQUENCE: 52

| Met | Ala | Asn | Thr | Lys | Tyr | Asn | Lys | Glu | Phe | Leu | Leu | Tyr | Leu | Ala | Gly |
| 1 | | | | 5 | | | | | 10 | | | | | 15 | |

| Phe | Val | Asp | Gly | Asp | Gly | Ser | Ile | Ile | Ala | Gln | Ile | Lys | Pro | Asn | Gln |
| | | | 20 | | | | | 25 | | | | | 30 | | |

| Ser | Tyr | Lys | Phe | Lys | His | Gln | Leu | Ser | Leu | Thr | Phe | Tyr | Val | Thr | Gln |
| | | 35 | | | | | 40 | | | | | 45 | | | |

| Lys | Thr | Gln | Arg | Arg | Trp | Phe | Leu | Asp | Lys | Leu | Val | Asp | Glu | Ile | Gly |
| | 50 | | | | | 55 | | | | | 60 | | | | |

| Val | Gly | Tyr | Val | Arg | Asp | Ser | Gly | Ser | Val | Ser | Asn | Tyr | Ile | Leu | Ser |
| 65 | | | | | 70 | | | | | 75 | | | | | 80 |

| Glu | Ile | Lys | Pro | Leu | His | Asn | Phe | Leu | Thr | Gln | Leu | Gln | Pro | Phe | Leu |
| | | | | 85 | | | | | 90 | | | | | 95 | |

| Lys | Leu | Lys | Gln | Lys | Gln | Ala | Asn | Leu | Val | Leu | Lys | Ile | Ile | Glu | Gln |
| | | | 100 | | | | | 105 | | | | | 110 | | |

| Leu | Pro | Ser | Ala | Lys | Glu | Ser | Pro | Asp | Lys | Phe | Leu | Glu | Val | Cys | Thr |
| | | | 115 | | | | | 120 | | | | | 125 | | |

| Trp | Val | Asp | Gln | Ile | Ala | Ala | Leu | Asn | Asp | Ser | Lys | Thr | Arg | Lys | Thr |
| | | 130 | | | | | 135 | | | | | 140 | | | |

| Thr | Ser | Glu | Thr | Val | Arg | Ala | Val | Leu | Asp | Ser | Leu | Ser | Glu | Lys | Lys |
| 145 | | | | | 150 | | | | | 155 | | | | | 160 |

| Lys | Ser | Ser | Pro | Ala | Ala | Asp |
| | | | | 165 | | |

<210> SEQ ID NO 53
<211> LENGTH: 167
<212> TYPE: PRT
<213> ORGANISM: Artificial Sequence
<220> FEATURE:
<223> OTHER INFORMATION: Description of Artificial Sequence: m16 variant

<400> SEQUENCE: 53

| Met | Ala | Asn | Thr | Lys | Tyr | Asn | Lys | Glu | Phe | Leu | Leu | Tyr | Leu | Ala | Gly |
| 1 | | | | 5 | | | | | 10 | | | | | 15 | |

| Phe | Val | Asp | Gly | Asp | Gly | Ser | Ile | Val | Ala | Gln | Ile | Lys | Pro | Asn | Gln |
| | | | 20 | | | | | 25 | | | | | 30 | | |

| Ser | Tyr | Lys | Phe | Lys | His | Gln | Leu | Ser | Leu | Thr | Phe | Tyr | Val | Thr | Gln |
| | | 35 | | | | | 40 | | | | | 45 | | | |

| Lys | Thr | Gln | Arg | Arg | Trp | Phe | Leu | Asp | Lys | Leu | Val | Asp | Glu | Ile | Gly |
| | 50 | | | | | 55 | | | | | 60 | | | | |

| Val | Gly | Tyr | Val | Tyr | Asp | Ser | Gly | Ser | Val | Ser | Arg | Tyr | Val | Leu | Ser |
| 65 | | | | | 70 | | | | | 75 | | | | | 80 |

| Glu | Ile | Lys | Pro | Leu | His | Asn | Phe | Leu | Thr | Gln | Leu | Gln | Pro | Phe | Leu |
| | | | | 85 | | | | | 90 | | | | | 95 | |

| Lys | Leu | Lys | Gln | Lys | Gln | Ala | Asn | Leu | Val | Leu | Lys | Ile | Ile | Glu | Gln |
| | | | 100 | | | | | 105 | | | | | 110 | | |

| Leu | Pro | Ser | Ala | Lys | Glu | Ser | Pro | Asp | Lys | Phe | Leu | Glu | Val | Cys | Thr |
| | | | 115 | | | | | 120 | | | | | 125 | | |

| Trp | Val | Asp | Gln | Ile | Ala | Ala | Leu | Asn | Asp | Ser | Lys | Thr | Arg | Lys | Thr |
| | | 130 | | | | | 135 | | | | | 140 | | | |

| Thr | Ser | Glu | Thr | Val | Arg | Ala | Val | Leu | Asp | Ser | Leu | Ser | Glu | Lys | Lys |
| 145 | | | | | 150 | | | | | 155 | | | | | 160 |

| Lys | Ser | Ser | Pro | Ala | Ala | Asp |
| | | | | 165 | | |

<210> SEQ ID NO 54
<211> LENGTH: 167
<212> TYPE: PRT
<213> ORGANISM: Artificial Sequence
<220> FEATURE:
<223> OTHER INFORMATION: Description of Artificial Sequence: m17
      variant

<400> SEQUENCE: 54

Met Ala Asn Thr Lys Tyr Asn Lys Glu Phe Leu Leu Tyr Leu Ala Gly
1               5                   10                  15

Phe Val Asp Gly Asp Gly Ser Ile Val Ala Gln Ile Lys Pro Asn Gln
            20                  25                  30

Ser Tyr Lys Phe Lys His Gln Leu Ser Leu Thr Phe Tyr Val Thr Gln
        35                  40                  45

Lys Thr Gln Arg Arg Trp Phe Leu Asp Lys Leu Val Asp Glu Ile Gly
    50                  55                  60

Val Gly Tyr Val Arg Asp Ser Gly Ser Val Ser Tyr Tyr Thr Leu Ser
65                  70                  75                  80

Glu Ile Lys Pro Leu His Asn Phe Leu Thr Gln Leu Gln Pro Phe Leu
                85                  90                  95

Lys Leu Lys Gln Lys Gln Ala Asn Leu Val Leu Lys Ile Ile Glu Gln
            100                 105                 110

Leu Pro Ser Ala Lys Glu Ser Pro Asp Lys Phe Leu Glu Val Cys Thr
        115                 120                 125

Trp Val Asp Gln Ile Ala Ala Leu Asn Asp Ser Lys Thr Arg Lys Thr
    130                 135                 140

Thr Ser Glu Thr Val Arg Ala Val Leu Asp Ser Leu Ser Glu Lys Lys
145                 150                 155                 160

Lys Ser Ser Pro Ala Ala Asp
                165

<210> SEQ ID NO 55
<211> LENGTH: 167
<212> TYPE: PRT
<213> ORGANISM: Artificial Sequence
<220> FEATURE:
<223> OTHER INFORMATION: Description of Artificial Sequence: m18
      variant

<400> SEQUENCE: 55

Met Ala Asn Thr Lys Tyr Asn Lys Glu Phe Leu Leu Tyr Leu Ala Gly
1               5                   10                  15

Phe Val Asp Gly Asp Gly Ser Ile Val Ala Gln Ile Lys Pro Asn Gln
            20                  25                  30

Ser Tyr Lys Phe Lys His Gln Leu Ser Leu Thr Phe Asn Val Thr Gln
        35                  40                  45

Lys Thr Gln Arg Arg Trp Phe Leu Asp Lys Leu Val Asp Glu Ile Gly
    50                  55                  60

Val Gly Tyr Val Ser Asp Ser Gly Ser Val Ser Arg Tyr Val Leu Ser
65                  70                  75                  80

Glu Ile Lys Pro Leu His Asn Phe Leu Thr Gln Leu Gln Pro Phe Leu
                85                  90                  95

Lys Leu Lys Gln Lys Gln Ala Asn Leu Val Leu Lys Ile Ile Glu Gln
            100                 105                 110

Leu Pro Ser Ala Lys Glu Ser Pro Asp Lys Phe Leu Glu Val Cys Thr
        115                 120                 125

Trp Val Asp Gln Ile Ala Ala Leu Asn Asp Ser Lys Thr Arg Lys Thr

```
                130               135                140
Thr Ser Glu Thr Val Arg Ala Val Leu Asp Ser Leu Ser Glu Lys Lys
145               150                155                160

Lys Ser Ser Pro Ala Ala Asp
            165

<210> SEQ ID NO 56
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 56
gcaactttag tgctgacaca tacagg                                         26

<210> SEQ ID NO 57
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 57
acaaccttga ttggagactt gacc                                           24

<210> SEQ ID NO 58
<211> LENGTH: 15
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (4)..(6)
<223> OTHER INFORMATION: a, c, t, g, unknown or other

<400> SEQUENCE: 58
ctannnttga ccttt                                                     15

<210> SEQ ID NO 59
<211> LENGTH: 15
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (10)..(12)
<223> OTHER INFORMATION: a, c, t, g, unknown or other

<400> SEQUENCE: 59
aaaggtcaan nntag                                                     15

<210> SEQ ID NO 60
<211> LENGTH: 167
<212> TYPE: PRT
<213> ORGANISM: Artificial Sequence
<220> FEATURE:
<223> OTHER INFORMATION: Description of Artificial Sequence: I-CreI
      variant

<400> SEQUENCE: 60

Met Ala Asn Thr Lys Tyr Asn Lys Glu Phe Leu Leu Tyr Leu Ala Gly
```

```
                1               5                  10                 15
Phe Val Asp Gly Asp Gly Ser Ile Ile Ala Gln Ile Glu Pro Asn Gln
                20                  25                 30

Ser Arg Lys Phe Lys His Arg Leu Arg Leu Thr Phe Ala Val Thr Gln
            35                  40                 45

Lys Thr Gln Arg Arg Trp Phe Leu Asp Lys Leu Val Asp Glu Ile Gly
        50                  55                 60

Val Gly Tyr Val His Asp Gln Gly Ser Val Ser Asn Tyr Ile Leu Ser
65                  70                 75                  80

Glu Ile Lys Pro Leu His Asn Phe Leu Thr Gln Leu Gln Pro Phe Leu
                85                  90                 95

Lys Leu Lys Gln Lys Gln Ala Asn Leu Val Leu Lys Ile Ile Glu Gln
            100                 105                110

Leu Pro Ser Ala Lys Glu Ser Pro Asp Lys Phe Leu Glu Val Cys Thr
        115                 120                125

Trp Val Asp Gln Ile Ala Ala Leu Asn Asp Ser Lys Thr Arg Lys Thr
        130                 135                 140

Thr Ser Glu Thr Val Arg Ala Val Leu Asp Ser Leu Ser Glu Lys Lys
145                 150                 155                 160

Lys Ser Ser Pro Ala Ala Asp
                165
```

<210> SEQ ID NO 61
<211> LENGTH: 167
<212> TYPE: PRT
<213> ORGANISM: Artificial Sequence
<220> FEATURE:
<223> OTHER INFORMATION: Description of Artificial Sequence: I-CreI
      variant

<400> SEQUENCE: 61

```
Met Ala Asn Thr Lys Tyr Asn Lys Glu Phe Leu Leu Tyr Leu Ala Gly
1               5                  10                 15

Phe Val Asp Gly Asp Gly Ser Ile Ile Ala Gln Ile Glu Pro Asn Gln
                20                  25                 30

Ser Arg Lys Phe Lys His Arg Leu Lys Leu Thr Phe Ala Val Thr Gln
            35                  40                 45

Lys Thr Gln Arg Arg Trp Phe Leu Asp Lys Leu Val Asp Glu Ile Gly
        50                  55                 60

Val Gly Tyr Val His Asp Gln Gly Ser Val Ser Asn Tyr Ile Leu Ser
65                  70                 75                  80

Glu Ile Lys Pro Leu His Asn Phe Leu Thr Gln Leu Gln Pro Phe Leu
                85                  90                 95

Lys Leu Lys Gln Lys Gln Ala Asn Leu Val Leu Lys Ile Ile Glu Gln
            100                 105                110

Leu Pro Ser Ala Lys Glu Ser Pro Asp Lys Phe Leu Glu Val Cys Thr
        115                 120                125

Trp Val Asp Gln Ile Ala Ala Leu Asn Asp Ser Lys Thr Arg Lys Thr
        130                 135                 140

Thr Ser Glu Thr Val Arg Ala Val Leu Asp Ser Leu Ser Glu Lys Lys
145                 150                 155                 160

Lys Ser Ser Pro Ala Ala Asp
                165
```

<210> SEQ ID NO 62
<211> LENGTH: 167
<212> TYPE: PRT

<213> ORGANISM: Artificial Sequence
<220> FEATURE:
<223> OTHER INFORMATION: Description of Artificial Sequence: I-CreI
    variant

<400> SEQUENCE: 62

Met Ala Asn Thr Lys Tyr Asn Lys Glu Phe Leu Leu Tyr Leu Ala Gly
1               5                   10                  15

Phe Val Asp Gly Asp Gly Ser Ile Ile Ala Gln Ile Glu Pro Asn Gln
            20                  25                  30

Ser Arg Lys Phe Lys His Arg Leu Arg Leu Thr Phe Ala Val Thr Gln
        35                  40                  45

Lys Thr Gln Arg Arg Trp Phe Leu Asp Lys Leu Val Asp Glu Ile Gly
    50                  55                  60

Val Gly Tyr Val Arg Asp Asn Gly Ser Val Ser Asn Tyr Ile Leu Ser
65                  70                  75                  80

Glu Ile Lys Pro Leu His Asn Phe Leu Thr Gln Leu Gln Pro Phe Leu
                85                  90                  95

Lys Leu Lys Gln Lys Gln Ala Asn Leu Val Leu Lys Ile Ile Glu Gln
            100                 105                 110

Leu Pro Ser Ala Lys Glu Ser Pro Asp Lys Phe Leu Glu Val Cys Thr
        115                 120                 125

Trp Val Asp Gln Ile Ala Ala Leu Asn Asp Ser Lys Thr Arg Lys Thr
    130                 135                 140

Thr Ser Glu Thr Val Arg Ala Val Leu Asp Ser Leu Ser Glu Lys Lys
145                 150                 155                 160

Lys Ser Ser Pro Ala Ala Asp
                165

<210> SEQ ID NO 63
<211> LENGTH: 167
<212> TYPE: PRT
<213> ORGANISM: Artificial Sequence
<220> FEATURE:
<223> OTHER INFORMATION: Description of Artificial Sequence: I-CreI
    variant

<400> SEQUENCE: 63

Met Ala Asn Thr Lys Tyr Asn Lys Glu Phe Leu Leu Tyr Leu Ala Gly
1               5                   10                  15

Phe Val Asp Gly Asp Gly Ser Ile Ile Ala Gln Ile Glu Pro Asn Gln
            20                  25                  30

Ser Arg Lys Phe Lys His Arg Leu Lys Leu Thr Phe Ala Val Thr Gln
        35                  40                  45

Lys Thr Gln Arg Arg Trp Phe Leu Asp Lys Leu Val Asp Glu Ile Gly
    50                  55                  60

Val Gly Tyr Val Arg Asp Ser Gly Ser Val Ser Asn Tyr Ile Leu Ser
65                  70                  75                  80

Glu Ile Lys Pro Leu His Asn Phe Leu Thr Gln Leu Gln Pro Phe Leu
                85                  90                  95

Lys Leu Lys Gln Lys Gln Ala Asn Leu Val Leu Lys Ile Ile Glu Gln
            100                 105                 110

Leu Pro Ser Ala Lys Glu Ser Pro Asp Lys Phe Leu Glu Val Cys Thr
        115                 120                 125

Trp Val Asp Gln Ile Ala Ala Leu Asn Asp Ser Lys Thr Arg Lys Thr
    130                 135                 140

Thr Ser Glu Thr Val Arg Ala Val Leu Asp Ser Leu Ser Glu Lys Lys
145                 150                 155                 160

Lys Ser Ser Pro Ala Ala Asp
            165

<210> SEQ ID NO 64
<211> LENGTH: 166
<212> TYPE: PRT
<213> ORGANISM: Artificial Sequence
<220> FEATURE:
<223> OTHER INFORMATION: Description of Artificial Sequence: I-CreI
      variant

<400> SEQUENCE: 64

Met Ala Asn Thr Lys Tyr Asn Lys Glu Phe Leu Leu Tyr Leu Ala Gly
1               5                   10                  15

Phe Val Asp Gly Asp Gly Ser Ile Ile Ala Gln Ile Glu Pro Asn Gln
            20                  25                  30

Ser Arg Lys Phe Lys His Arg Leu Lys Leu Thr Phe Val Thr Gln Lys
        35                  40                  45

Thr Gln Arg Arg Trp Phe Leu Asp Lys Leu Val Asp Glu Ile Gly Val
    50                  55                  60

Gly Tyr Val Arg Asp Ala Gly Ser Val Ser Asn Tyr Ile Leu Ser Glu
65                  70                  75                  80

Ile Lys Pro Leu His Asn Phe Leu Thr Gln Leu Gln Pro Phe Leu Lys
                85                  90                  95

Leu Lys Gln Lys Gln Ala Asn Leu Val Leu Lys Ile Ile Glu Gln Leu
            100                 105                 110

Pro Ser Ala Lys Glu Ser Pro Asp Lys Phe Leu Glu Val Cys Thr Trp
        115                 120                 125

Val Asp Gln Ile Ala Ala Leu Asn Asp Ser Lys Thr Arg Lys Thr Thr
    130                 135                 140

Ser Glu Thr Val Arg Ala Val Leu Asp Ser Leu Ser Glu Lys Lys Lys
145                 150                 155                 160

Ser Ser Pro Ala Ala Asp
            165

<210> SEQ ID NO 65
<211> LENGTH: 167
<212> TYPE: PRT
<213> ORGANISM: Artificial Sequence
<220> FEATURE:
<223> OTHER INFORMATION: Description of Artificial Sequence: I-CreI
      variant

<400> SEQUENCE: 65

Met Ala Asn Thr Lys Tyr Asn Lys Glu Phe Leu Leu Tyr Leu Ala Gly
1               5                   10                  15

Phe Val Asp Gly Asp Gly Ser Ile Ile Ala Gln Ile Glu Pro Asn Gln
            20                  25                  30

Ser Arg Lys Phe Lys His Arg Leu Lys Leu Thr Phe Ala Val Thr Gln
        35                  40                  45

Lys Thr Gln Arg Arg Trp Phe Leu Asp Lys Leu Val Asp Glu Ile Gly
    50                  55                  60

Val Gly Tyr Val Arg Asp Gly Gly Ser Val Ser Asn Tyr Ile Leu Ser
65                  70                  75                  80

Glu Ile Lys Pro Leu His Asn Phe Leu Thr Gln Leu Gln Pro Phe Leu
                85                  90                  95

Lys Leu Lys Gln Lys Gln Ala Asn Leu Val Leu Lys Ile Ile Glu Gln
            100                 105                 110

```
Leu Pro Ser Ala Lys Glu Ser Pro Asp Lys Phe Leu Glu Val Cys Thr
            115                 120                 125

Trp Val Asp Gln Ile Ala Ala Leu Asn Asp Ser Lys Thr Arg Lys Thr
        130                 135                 140

Thr Ser Glu Thr Val Arg Ala Val Leu Asp Ser Leu Ser Glu Lys Lys
145                 150                 155                 160

Lys Ser Ser Pro Ala Ala Asp
                165

<210> SEQ ID NO 66
<211> LENGTH: 167
<212> TYPE: PRT
<213> ORGANISM: Artificial Sequence
<220> FEATURE:
<223> OTHER INFORMATION: Description of Artificial Sequence: I-CreI
      variant

<400> SEQUENCE: 66

Met Ala Asn Thr Lys Tyr Asn Lys Glu Phe Leu Leu Tyr Leu Ala Gly
1               5                   10                  15

Phe Val Asp Gly Asp Gly Ser Ile Ile Ala Gln Ile Glu Pro Asn Gln
            20                  25                  30

Ser Arg Lys Phe Lys His Arg Leu Arg Leu Thr Phe Ala Val Thr Gln
        35                  40                  45

Lys Thr Gln Arg Arg Trp Phe Leu Asp Lys Leu Val Asp Glu Ile Gly
 50                 55                  60

Val Gly Tyr Val Ser Asp Gln Gly Ser Val Ser Asn Tyr Ile Leu Ser
65                  70                  75                  80

Glu Ile Lys Pro Leu His Asn Phe Leu Thr Gln Leu Gln Pro Phe Leu
                85                  90                  95

Lys Leu Lys Gln Lys Gln Ala Asn Leu Val Leu Lys Ile Ile Glu Gln
            100                 105                 110

Leu Pro Ser Ala Lys Glu Ser Pro Asp Lys Phe Leu Glu Val Cys Thr
            115                 120                 125

Trp Val Asp Gln Ile Ala Ala Leu Asn Asp Ser Lys Thr Arg Lys Thr
        130                 135                 140

Thr Ser Glu Thr Val Arg Ala Val Leu Asp Ser Leu Ser Glu Lys Lys
145                 150                 155                 160

Lys Ser Ser Pro Ala Ala Asp
                165

<210> SEQ ID NO 67
<211> LENGTH: 167
<212> TYPE: PRT
<213> ORGANISM: Artificial Sequence
<220> FEATURE:
<223> OTHER INFORMATION: Description of Artificial Sequence: I-CreI
      variant

<400> SEQUENCE: 67

Met Ala Asn Thr Lys Tyr Asn Lys Glu Phe Leu Leu Tyr Leu Ala Gly
1               5                   10                  15

Phe Val Asp Gly Asp Gly Ser Ile Ile Ala Gln Ile Glu Pro Asn Gln
            20                  25                  30

Ser Arg Lys Phe Lys His Arg Leu Lys Leu Thr Phe Ala Val Thr Gln
        35                  40                  45

Lys Thr Gln Arg Arg Trp Phe Leu Asp Lys Leu Val Asp Glu Ile Gly
 50                 55                  60

Val Gly Tyr Val Thr Asp Asn Gly Ser Val Ser Asn Tyr Ile Leu Ser
```

```
                65                  70                  75                  80
Glu Ile Lys Pro Leu His Asn Phe Leu Thr Gln Leu Gln Pro Phe Leu
                    85                  90                  95
Lys Leu Lys Gln Lys Gln Ala Asn Leu Val Leu Lys Ile Ile Glu Gln
                100                 105                 110
Leu Pro Ser Ala Lys Glu Ser Pro Asp Lys Phe Leu Glu Val Cys Thr
            115                 120                 125
Trp Val Asp Gln Ile Ala Ala Leu Asn Asp Ser Lys Thr Arg Lys Thr
        130                 135                 140
Thr Ser Glu Thr Val Arg Ala Val Leu Asp Ser Leu Ser Glu Lys Lys
145                 150                 155                 160

Lys Ser Ser Pro Ala Ala Asp
                165

<210> SEQ ID NO 68
<211> LENGTH: 59
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 68
gcataaatta ctatacttct atagacacgc aaacacaaat acacagcggc cttgccacc      59

<210> SEQ ID NO 69
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 69
ggctcgagga gctcgtctag aggatcgctc gagttatcag tcggccgc                  48

<210> SEQ ID NO 70
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 70
ttaagcgaaa tcaagccg                                                   18

<210> SEQ ID NO 71
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 71
cggcttgatt tcgcttaa                                                   18

<210> SEQ ID NO 72
<211> LENGTH: 167
<212> TYPE: PRT
<213> ORGANISM: Artificial Sequence
<220> FEATURE:
<223> OTHER INFORMATION: Description of Artificial Sequence: I-CreI
      variant
```

<400> SEQUENCE: 72

```
Met Ala Asn Thr Lys Tyr Asn Lys Glu Phe Leu Leu Tyr Leu Ala Gly
1               5                   10                  15

Phe Val Asp Gly Asp Gly Ser Ile Ile Ala Gln Ile Glu Pro Asn Gln
            20                  25                  30

Ser Arg Lys Phe Lys His Arg Leu Arg Leu Thr Phe Ala Val Thr Gln
        35                  40                  45

Lys Thr Gln Arg Arg Trp Phe Leu Asp Lys Leu Val Asp Glu Ile Gly
    50                  55                  60

Val Gly Tyr Val His Asp Gln Gly Ser Val Ser Asn Tyr Ile Leu Ser
65                  70                  75                  80

Glu Ile Lys Pro Leu His Asn Phe Leu Thr Gln Leu Gln Pro Phe Leu
                85                  90                  95

Lys Leu Lys Gln Lys Gln Ala Asn Leu Ala Leu Arg Ile Ile Glu Gln
            100                 105                 110

Leu Pro Ser Ala Lys Glu Ser Pro Asp Lys Phe Leu Glu Val Cys Thr
        115                 120                 125

Trp Val Asp Gln Ile Ala Ala Leu Asn Asp Ser Lys Thr Arg Lys Thr
    130                 135                 140

Thr Ser Glu Thr Val Arg Ala Val Leu Asp Ser Leu Ser Glu Lys Lys
145                 150                 155                 160

Lys Ser Ser Pro Ala Ala Asp
                165
```

<210> SEQ ID NO 73
<211> LENGTH: 167
<212> TYPE: PRT
<213> ORGANISM: Artificial Sequence
<220> FEATURE:
<223> OTHER INFORMATION: Description of Artificial Sequence: I-CreI variant

<400> SEQUENCE: 73

```
Met Ala Asn Thr Lys Tyr Asn Lys Glu Phe Leu Leu Tyr Leu Ala Gly
1               5                   10                  15

Phe Val Asp Gly Asp Gly Ser Ile Ile Ala Gln Ile Glu Pro Asn Gln
            20                  25                  30

Ser Arg Lys Phe Lys His Arg Leu Lys Leu Thr Phe Ala Val Thr Gln
        35                  40                  45

Lys Thr Gln Arg Arg Trp Phe Leu Asp Lys Leu Val Asp Glu Ile Gly
    50                  55                  60

Val Gly Tyr Val His Asp Gln Gly Ser Val Ser Asn Tyr Ile Leu Ser
65                  70                  75                  80

Glu Ile Lys Pro Leu His Asn Phe Leu Thr Gln Leu Gln Pro Phe Leu
                85                  90                  95

Lys Leu Lys Gln Lys Gln Ala Asn Leu Ala Leu Arg Ile Ile Glu Gln
            100                 105                 110

Leu Pro Ser Ala Lys Glu Ser Pro Asp Lys Phe Leu Glu Val Cys Thr
        115                 120                 125

Trp Val Asp Gln Ile Ala Ala Leu Asn Asp Ser Lys Thr Arg Lys Thr
    130                 135                 140

Thr Ser Glu Thr Val Arg Ala Ala Leu Gly Ser Leu Ser Glu Glu Lys
145                 150                 155                 160

Lys Ser Ser Pro Ala Ala Asp
                165
```

<210> SEQ ID NO 74
<211> LENGTH: 167
<212> TYPE: PRT
<213> ORGANISM: Artificial Sequence
<220> FEATURE:
<223> OTHER INFORMATION: Description of Artificial Sequence: I-CreI variant

<400> SEQUENCE: 74

Met Ala Asn Thr Lys Tyr Asn Lys Glu Phe Leu Leu Tyr Leu Ala Gly
1               5                   10                  15

Phe Val Asp Ser Asp Gly Ser Ile Val Ala Gln Ile Lys Pro Asn Gln
            20                  25                  30

Ser Tyr Lys Phe Lys His Gln Leu Ser Leu Thr Phe Tyr Val Thr Gln
        35                  40                  45

Lys Thr Gln Arg Arg Trp Phe Leu Asp Lys Leu Val Asp Glu Ile Gly
    50                  55                  60

Val Gly Tyr Val Arg Asp Ser Gly Ser Val Ser Asn Tyr Val Leu Ser
65                  70                  75                  80

Glu Ile Lys Pro Leu His Asn Phe Leu Thr Gln Leu Gln Pro Phe Leu
                85                  90                  95

Lys Leu Lys Gln Lys Gln Ala Asn Leu Val Leu Lys Ile Ile Glu Gln
            100                 105                 110

Leu Pro Ser Ala Lys Glu Ser Pro Asp Lys Phe Leu Glu Val Cys Thr
        115                 120                 125

Trp Val Asp Gln Ile Ala Ala Leu Asn Asp Ser Lys Thr Arg Lys Thr
    130                 135                 140

Thr Ser Glu Thr Val Arg Ala Val Leu Asp Ser Leu Ser Glu Lys Lys
145                 150                 155                 160

Lys Ser Ser Pro Ala Ala Asp
                165

<210> SEQ ID NO 75
<211> LENGTH: 167
<212> TYPE: PRT
<213> ORGANISM: Artificial Sequence
<220> FEATURE:
<223> OTHER INFORMATION: Description of Artificial Sequence: I-CreI variant

<400> SEQUENCE: 75

Met Ala Asn Thr Lys Tyr Asn Lys Glu Phe Leu Leu Tyr Leu Ala Gly
1               5                   10                  15

Phe Val Asp Ser Asp Gly Ser Ile Val Ala Gln Ile Lys Pro Asn Gln
            20                  25                  30

Ser Tyr Lys Phe Lys His Gln Leu Ser Leu Thr Phe Tyr Val Thr Gln
        35                  40                  45

Lys Thr Gln Arg Arg Trp Phe Leu Asp Lys Leu Val Asp Glu Ile Gly
    50                  55                  60

Val Gly Tyr Val Arg Asp Ser Gly Ser Val Ser Gln Tyr Ile Leu Ser
65                  70                  75                  80

Glu Ile Lys Pro Leu His Asn Phe Leu Thr Gln Leu Gln Pro Phe Leu
                85                  90                  95

Lys Leu Lys Gln Lys Gln Ala Asn Leu Val Leu Lys Ile Ile Glu Gln
            100                 105                 110

Leu Pro Ser Ala Lys Glu Ser Pro Asp Lys Phe Leu Glu Val Cys Thr
        115                 120                 125

Trp Val Asp Gln Ile Ala Ala Leu Asn Asp Ser Lys Thr Arg Lys Thr 130                 135                 140
Thr Ser Glu Thr Val Arg Ala Val Leu Asp Ser Leu Ser Glu Lys Lys
145                 150                 155                 160

Lys Ser Ser Pro Ala Ala Asp
                165

<210> SEQ ID NO 76
<211> LENGTH: 167
<212> TYPE: PRT
<213> ORGANISM: Artificial Sequence
<220> FEATURE:
<223> OTHER INFORMATION: Description of Artificial Sequence: I-CreI
      variant

<400> SEQUENCE: 76

Met Ala Asn Thr Lys Tyr Asn Lys Glu Phe Leu Leu Tyr Leu Ala Gly
1               5                   10                  15

Phe Val Asp Gly Asp Gly Ser Ile Val Ala Gln Ile Lys Pro Asn Gln
                20                  25                  30

Ser Tyr Lys Phe Lys His Gln Leu Ser Leu Thr Phe Tyr Val Thr Gln
            35                  40                  45

Lys Thr Gln Arg Arg Trp Phe Leu Asp Lys Leu Val Asp Glu Ile Gly
        50                  55                  60

Val Gly Tyr Val Ser Asp Ser Gly Ser Val Ser Arg Tyr Ile Leu Ser
65                  70                  75                  80

Glu Ile Lys Pro Leu His Asn Phe Leu Thr Gln Leu Gln Pro Phe Leu
                85                  90                  95

Lys Leu Lys Gln Lys Gln Ala Asn Leu Ala Leu Lys Ile Ile Glu Gln
            100                 105                 110

Leu Pro Ser Ala Lys Glu Ser Pro Asp Lys Phe Leu Glu Val Cys Thr
        115                 120                 125

Trp Val Asp Gln Ile Ala Ala Leu Asn Asp Ser Lys Thr Arg Lys Thr
    130                 135                 140

Thr Ser Glu Thr Val Arg Ala Val Leu Asp Ser Leu Ser Glu Lys Lys
145                 150                 155                 160

Lys Ser Ser Pro Ala Ala Asp
                165

<210> SEQ ID NO 77
<211> LENGTH: 167
<212> TYPE: PRT
<213> ORGANISM: Artificial Sequence
<220> FEATURE:
<223> OTHER INFORMATION: Description of Artificial Sequence: I-CreI
      variant

<400> SEQUENCE: 77

Met Ala Asn Thr Lys Tyr Asn Lys Glu Phe Leu Leu Tyr Leu Ala Gly
1               5                   10                  15

Phe Val Asp Gly Asp Gly Ser Ile Val Ala Gln Ile Lys Pro Asn Gln
                20                  25                  30

Ser Tyr Lys Phe Lys His Gln Leu Ser Leu Thr Phe Tyr Val Thr Gln
            35                  40                  45

Lys Thr Gln Arg Arg Trp Phe Leu Asp Lys Leu Val Asp Glu Ile Gly
        50                  55                  60

Val Gly Tyr Val Ser Asp Ser Gly Ser Val Ser Arg Tyr Ile Leu Gly
65                  70                  75                  80

Glu Ile Lys Pro Leu His Asn Phe Leu Thr Gln Leu Gln Pro Phe Leu
                85                  90                  95

Lys Leu Lys Gln Lys Gln Ala Asn Leu Val Leu Lys Ile Ile Glu Gln
            100                 105                 110

Leu Pro Ser Ala Lys Glu Ser Pro Asp Lys Phe Leu Glu Val Cys Thr
        115                 120                 125

Trp Val Asp Gln Ile Ala Ala Leu Asn Asp Ser Lys Thr Arg Lys Thr
    130                 135                 140

Thr Ser Glu Thr Val Arg Ala Val Leu Asp Ser Leu Ser Glu Lys Lys
145                 150                 155                 160

Lys Ser Ser Pro Ala Ala Asp
                165

<210> SEQ ID NO 78
<211> LENGTH: 77
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 78
ggggacaagt ttgtacaaaa aagcaggctt cgaaggagat agaaccatgg ccaataccaa    60
atataacaaa gagttcc                                                   77

<210> SEQ ID NO 79
<211> LENGTH: 64
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 79
ggggaccact ttgtacaaga aagctgggtt tagtcggccg ccggggagga tttcttcttc    60
tcgc                                                                 64

<210> SEQ ID NO 80
<211> LENGTH: 24
<212> TYPE: DNA
<213> ORGANISM: Artificial Sequence
<220> FEATURE:
<223> OTHER INFORMATION: Description of Artificial Sequence: I-CreI
      DNA target

<400> SEQUENCE: 80
tcaaaacgtc gtgagacagt ttgg                                           24

<210> SEQ ID NO 81
<211> LENGTH: 18
<212> TYPE: DNA
<213> ORGANISM: Artificial Sequence
<220> FEATURE:
<223> OTHER INFORMATION: Description of Artificial Sequence: I-SceI
      DNA target

<400> SEQUENCE: 81
tagggataac agggtaat                                                  18

<210> SEQ ID NO 82
<211> LENGTH: 167
<212> TYPE: PRT
<213> ORGANISM: Artificial Sequence
<220> FEATURE:
<223> OTHER INFORMATION: Description of Artificial Sequence: I-CreI
      variant

<400> SEQUENCE: 82

```
Met Ala Asn Thr Lys Tyr Asn Lys Glu Phe Leu Leu Tyr Leu Ala Gly
1               5                   10                  15

Phe Val Asp Gly Asp Gly Ser Ile Ile Ala Gln Ile Lys Pro His Gln
            20                  25                  30

Ser Ser Lys Phe Lys His Gln Leu Ser Leu Thr Phe Glu Val Thr Gln
        35                  40                  45

Lys Thr Gln Arg Arg Trp Phe Leu Asp Lys Leu Val Asp Glu Ile Gly
    50                  55                  60

Val Gly Tyr Val Cys Asp Ser Gly Ser Val Ser Asn Tyr Ile Leu Ser
65                  70                  75                  80

Glu Ile Lys Pro Leu His Asn Phe Leu Thr Gln Leu Gln Pro Phe Leu
                85                  90                  95

Lys Leu Lys Gln Lys Gln Ala Asn Leu Val Leu Lys Ile Ile Glu Gln
            100                 105                 110

Leu Pro Ser Ala Lys Glu Ser Pro Asp Lys Phe Leu Glu Val Cys Thr
        115                 120                 125

Trp Val Asp Gln Ile Ala Ala Leu Asn Asp Ser Lys Thr Arg Lys Thr
    130                 135                 140

Thr Ser Glu Thr Val Arg Ala Val Leu Asp Ser Leu Ser Glu Lys Lys
145                 150                 155                 160

Lys Ser Ser Pro Ala Ala Asp
                165
```

<210> SEQ ID NO 83
<211> LENGTH: 167
<212> TYPE: PRT
<213> ORGANISM: Artificial Sequence
<220> FEATURE:
<223> OTHER INFORMATION: Description of Artificial Sequence: I-CreI
      variant

<400> SEQUENCE: 83

```
Met Ala Asn Thr Lys Tyr Asn Lys Glu Phe Leu Leu Tyr Leu Ala Gly
1               5                   10                  15

Phe Val Asp Gly Asp Gly Ser Ile Ile Ala Gln Ile Lys Pro Asn Gln
            20                  25                  30

Asn Gly Lys Phe Lys His Gln Leu Ser Leu Thr Phe Lys Val Thr Gln
        35                  40                  45

Lys Thr Gln Arg Arg Trp Phe Leu Asp Lys Leu Val Asp Glu Ile Gly
    50                  55                  60

Val Gly Tyr Val Arg Asp Glu Gly Ser Val Ser Asn Tyr Ile Leu Ser
65                  70                  75                  80

Glu Ile Lys Pro Leu His Asn Phe Leu Thr Gln Leu Gln Pro Phe Leu
                85                  90                  95

Lys Leu Lys Gln Lys Gln Ala Asn Leu Val Leu Lys Ile Ile Glu Gln
            100                 105                 110

Leu Pro Ser Ala Lys Glu Ser Pro Asp Lys Phe Leu Glu Val Cys Thr
        115                 120                 125

Trp Val Asp Gln Ile Ala Ala Leu Asn Asp Ser Lys Thr Arg Lys Thr
    130                 135                 140

Thr Ser Glu Thr Val Arg Ala Val Leu Asp Ser Leu Ser Glu Lys Lys
145                 150                 155                 160

Lys Ser Ser Pro Ala Ala Asp
                165
```

<210> SEQ ID NO 84
<211> LENGTH: 167
<212> TYPE: PRT
<213> ORGANISM: Artificial Sequence
<220> FEATURE:
<223> OTHER INFORMATION: Description of Artificial Sequence: I-CreI variant

<400> SEQUENCE: 84

Met Ala Asn Thr Lys Tyr Asn Lys Glu Phe Leu Leu Tyr Leu Ala Gly
1               5                   10                  15

Phe Val Asp Gly Asp Gly Ser Ile Ile Ala Gln Ile Lys Pro Asn Gln
            20                  25                  30

Ser Arg Lys Phe Lys His Asn Leu Gln Leu Thr Phe Asn Val Thr Gln
        35                  40                  45

Lys Thr Gln Arg Arg Trp Phe Leu Asp Lys Leu Val Asp Glu Ile Gly
    50                  55                  60

Val Gly Tyr Val Arg Asp Ser Gly Ser Val Ser Arg Tyr Asp Leu Ser
65                  70                  75                  80

Glu Ile Lys Pro Leu His Asn Phe Leu Thr Gln Leu Gln Pro Phe Leu
                85                  90                  95

Lys Leu Lys Gln Lys Gln Ala Asn Leu Val Leu Lys Ile Ile Glu Gln
            100                 105                 110

Leu Pro Ser Ala Lys Glu Ser Pro Asp Lys Phe Leu Glu Val Cys Thr
        115                 120                 125

Trp Val Asp Gln Ile Ala Ala Leu Asn Asp Ser Lys Thr Arg Lys Thr
    130                 135                 140

Thr Ser Glu Thr Val Arg Ala Val Leu Asp Ser Leu Ser Glu Lys Lys
145                 150                 155                 160

Lys Ser Ser Pro Ala Ala Asp
                165

<210> SEQ ID NO 85
<211> LENGTH: 167
<212> TYPE: PRT
<213> ORGANISM: Artificial Sequence
<220> FEATURE:
<223> OTHER INFORMATION: Description of Artificial Sequence: I-CreI variant

<400> SEQUENCE: 85

Met Ala Asn Thr Lys Tyr Asn Lys Glu Phe Leu Leu Tyr Leu Ala Gly
1               5                   10                  15

Phe Val Asp Gly Asp Gly Ser Ile Ile Ala Gln Ile Ser Pro Asn Gln
            20                  25                  30

Ser Tyr Lys Phe Lys His Arg Leu Lys Leu Thr Phe Asp Val Thr Gln
        35                  40                  45

Lys Thr Gln Arg Arg Trp Phe Leu Asp Lys Leu Val Asp Glu Ile Gly
    50                  55                  60

Val Gly Tyr Val Tyr Asp Ser Gly Ser Val Ser Ser Tyr Arg Leu Ser
65                  70                  75                  80

Glu Ile Lys Pro Leu His Asn Phe Leu Thr Gln Leu Gln Pro Phe Leu
                85                  90                  95

Lys Leu Lys Gln Lys Gln Ala Asn Leu Val Leu Lys Ile Ile Glu Gln
            100                 105                 110

Leu Pro Ser Ala Lys Glu Ser Pro Asp Lys Phe Leu Glu Val Cys Thr
        115                 120                 125

Trp Val Asp Gln Ile Ala Ala Leu Asn Asp Ser Lys Thr Arg Lys Thr

```
                130                 135                 140
Thr Ser Glu Thr Val Arg Ala Val Leu Asp Ser Leu Ser Glu Lys Lys
145                 150                 155                 160

Lys Ser Ser Pro Ala Ala Asp
                165

<210> SEQ ID NO 86
<211> LENGTH: 167
<212> TYPE: PRT
<213> ORGANISM: Artificial Sequence
<220> FEATURE:
<223> OTHER INFORMATION: Description of Artificial Sequence: I-CreI
      variant

<400> SEQUENCE: 86

Met Ala Asn Thr Lys Tyr Asn Lys Glu Phe Leu Leu Tyr Leu Ala Gly
1               5                   10                  15

Phe Val Asp Gly Asp Gly Ser Ile Ile Ala Gln Ile Lys Pro Asn Gln
                20                  25                  30

Ser Cys Lys Phe Lys His Gln Leu Ser Leu Thr Phe Thr Val Thr Gln
            35                  40                  45

Lys Thr Gln Arg Arg Trp Phe Leu Asp Lys Leu Val Asp Glu Ile Gly
        50                  55                  60

Val Gly Tyr Val Arg Asp Ser Gly Ser Val Ser Tyr Tyr Ile Leu Ser
65                  70                  75                  80

Glu Ile Lys Pro Leu His Asn Phe Leu Thr Gln Leu Gln Pro Phe Leu
                85                  90                  95

Lys Leu Lys Gln Lys Gln Ala Asn Leu Val Leu Lys Ile Ile Glu Gln
            100                 105                 110

Leu Pro Ser Ala Lys Glu Ser Pro Asp Lys Phe Leu Glu Val Cys Thr
        115                 120                 125

Trp Val Asp Gln Ile Ala Ala Leu Asn Asp Ser Lys Thr Arg Lys Thr
    130                 135                 140

Thr Ser Glu Thr Val Arg Ala Val Leu Asp Ser Leu Ser Glu Lys Lys
145                 150                 155                 160

Lys Ser Ser Pro Ala Ala Asp
                165

<210> SEQ ID NO 87
<211> LENGTH: 167
<212> TYPE: PRT
<213> ORGANISM: Artificial Sequence
<220> FEATURE:
<223> OTHER INFORMATION: Description of Artificial Sequence: I-CreI
      variant

<400> SEQUENCE: 87

Met Ala Asn Thr Lys Tyr Asn Lys Glu Phe Leu Leu Tyr Leu Ala Gly
1               5                   10                  15

Phe Val Asp Gly Asp Gly Ser Ile Ile Ala Gln Ile Lys Pro Asn Gln
                20                  25                  30

Thr Cys Lys Phe Lys His Gln Leu Ser Leu Thr Phe Gln Val Thr Gln
            35                  40                  45

Lys Thr Gln Arg Arg Trp Phe Leu Asp Lys Leu Val Asp Glu Ile Gly
        50                  55                  60

Val Gly Tyr Val Thr Asp Asn Gly Ser Val Ser Asn Tyr Ile Leu Ser
65                  70                  75                  80

Glu Ile Lys Pro Leu His Asn Phe Leu Thr Gln Leu Gln Pro Phe Leu
                85                  90                  95
```

```
Lys Leu Lys Gln Lys Gln Ala Asn Leu Val Leu Lys Ile Ile Glu Gln
            100                 105                 110

Leu Pro Ser Ala Lys Glu Ser Pro Asp Lys Phe Leu Glu Val Cys Thr
        115                 120                 125

Trp Val Asp Gln Ile Ala Ala Leu Asn Asp Ser Lys Thr Arg Lys Thr
    130                 135                 140

Thr Ser Glu Thr Val Arg Ala Val Leu Asp Ser Leu Ser Glu Lys Lys
145                 150                 155                 160

Lys Ser Ser Pro Ala Ala Asp
                165

<210> SEQ ID NO 88
<211> LENGTH: 167
<212> TYPE: PRT
<213> ORGANISM: Artificial Sequence
<220> FEATURE:
<223> OTHER INFORMATION: Description of Artificial Sequence: I-CreI
      variant

<400> SEQUENCE: 88

Met Ala Asn Thr Lys Tyr Asn Lys Glu Phe Leu Leu Tyr Leu Ala Gly
1               5                   10                  15

Phe Val Asp Gly Asp Gly Ser Ile Ile Ala Gln Ile Lys Pro Asn Gln
            20                  25                  30

Ser Tyr Lys Phe Lys His Gln Leu Ser Leu Thr Phe Gln Val Thr Gln
        35                  40                  45

Lys Thr Gln Arg Arg Trp Phe Leu Asp Lys Leu Val Asp Glu Ile Gly
    50                  55                  60

Val Gly Tyr Val Arg Asp Ser Gly Ser Val Ser Arg Tyr Tyr Leu Ser
65                  70                  75                  80

Glu Ile Lys Pro Leu His Asn Phe Leu Thr Gln Leu Gln Pro Phe Leu
                85                  90                  95

Lys Leu Lys Gln Lys Gln Ala Asn Leu Val Leu Lys Ile Ile Glu Gln
            100                 105                 110

Leu Pro Ser Ala Lys Glu Ser Pro Asp Lys Phe Leu Glu Val Cys Thr
        115                 120                 125

Trp Val Asp Gln Ile Ala Ala Leu Asn Asp Ser Lys Thr Arg Lys Thr
    130                 135                 140

Thr Ser Glu Thr Val Arg Ala Val Leu Asp Ser Leu Ser Glu Lys Lys
145                 150                 155                 160

Lys Ser Ser Pro Ala Ala Asp
                165

<210> SEQ ID NO 89
<211> LENGTH: 167
<212> TYPE: PRT
<213> ORGANISM: Artificial Sequence
<220> FEATURE:
<223> OTHER INFORMATION: Description of Artificial Sequence: I-CreI
      variant

<400> SEQUENCE: 89

Met Ala Asn Thr Lys Tyr Asn Lys Glu Phe Leu Leu Tyr Leu Ala Gly
1               5                   10                  15

Phe Val Asp Gly Asp Gly Ser Ile Ile Ala Gln Ile Ser Pro Asn Gln
            20                  25                  30

Ser Tyr Lys Phe Lys His Arg Leu Lys Leu Thr Phe Thr Val Thr Gln
        35                  40                  45
```

```
Lys Thr Gln Arg Arg Trp Phe Leu Asp Lys Leu Val Asp Glu Ile Gly
         50                  55                  60

Val Gly Tyr Val Asn Asp Asn Gly Ser Val Ser Asn Tyr Ile Leu Ser
 65                  70                  75                  80

Glu Ile Lys Pro Leu His Asn Phe Leu Thr Gln Leu Gln Pro Phe Leu
                 85                  90                  95

Lys Leu Lys Gln Lys Gln Ala Asn Leu Val Leu Lys Ile Ile Glu Gln
            100                 105                 110

Leu Pro Ser Ala Lys Glu Ser Pro Asp Lys Phe Leu Glu Val Cys Thr
            115                 120                 125

Trp Val Asp Gln Ile Ala Ala Leu Asn Asp Ser Lys Thr Arg Lys Thr
        130                 135                 140

Thr Ser Glu Thr Val Arg Ala Val Leu Asp Ser Leu Ser Glu Lys Lys
145                 150                 155                 160

Lys Ser Ser Pro Ala Ala Asp
                165

<210> SEQ ID NO 90
<211> LENGTH: 167
<212> TYPE: PRT
<213> ORGANISM: Artificial Sequence
<220> FEATURE:
<223> OTHER INFORMATION: Description of Artificial Sequence: I-CreI
      variant

<400> SEQUENCE: 90

Met Ala Asn Thr Lys Tyr Asn Lys Glu Phe Leu Leu Tyr Leu Ala Gly
  1               5                  10                  15

Phe Val Asp Gly Asp Gly Ser Ile Ile Ala Gln Ile Ala Pro Asn Gln
                 20                  25                  30

Ser Ser Lys Phe Lys His Arg Leu Lys Leu Thr Phe Asn Val Thr Gln
            35                  40                  45

Lys Thr Gln Arg Arg Trp Phe Leu Asp Lys Leu Val Asp Glu Ile Gly
         50                  55                  60

Val Gly Tyr Val Tyr Asp Ser Gly Ser Val Ser Arg Tyr Val Leu Ser
 65                  70                  75                  80

Glu Ile Lys Pro Leu His Asn Phe Leu Thr Gln Leu Gln Pro Phe Leu
                 85                  90                  95

Lys Leu Lys Gln Lys Gln Ala Asn Leu Val Leu Lys Ile Ile Glu Gln
            100                 105                 110

Leu Pro Ser Ala Lys Glu Ser Pro Asp Lys Phe Leu Glu Val Cys Thr
            115                 120                 125

Trp Val Asp Gln Ile Ala Ala Leu Asn Asp Ser Lys Thr Arg Lys Thr
        130                 135                 140

Thr Ser Glu Thr Val Arg Ala Val Leu Asp Ser Leu Ser Glu Lys Lys
145                 150                 155                 160

Lys Ser Ser Pro Ala Ala Asp
                165

<210> SEQ ID NO 91
<211> LENGTH: 167
<212> TYPE: PRT
<213> ORGANISM: Artificial Sequence
<220> FEATURE:
<223> OTHER INFORMATION: Description of Artificial Sequence: I-CreI
      variant

<400> SEQUENCE: 91

Met Ala Asn Thr Lys Tyr Asn Lys Glu Phe Leu Leu Tyr Leu Ala Gly
```

-continued

```
               1               5                  10                 15
           Phe Val Asp Gly Asp Gly Ser Ile Ile Ala Gln Ile Lys Pro Asn Gln
                           20                 25                 30

Asp His Lys Phe Lys His Gln Leu Ser Leu Thr Phe Lys Val Thr Gln
                           35                 40                 45

Lys Thr Gln Arg Arg Trp Phe Leu Asp Lys Leu Val Asp Glu Ile Gly
                           50                 55                 60

Val Gly Tyr Val Glu Asp Ser Gly Ser Val Ser Asp Tyr Arg Leu Ser
            65                 70                 75                 80

Glu Ile Lys Pro Leu His Asn Phe Leu Thr Gln Leu Gln Pro Phe Leu
                           85                 90                 95

Lys Leu Lys Gln Lys Gln Ala Asn Leu Val Leu Lys Ile Ile Glu Gln
                           100                105                110

Leu Pro Ser Ala Lys Glu Ser Pro Asp Lys Phe Leu Glu Val Cys Thr
                           115                120                125

Trp Val Asp Gln Ile Ala Ala Leu Asn Asp Ser Lys Thr Arg Lys Thr
                           130                135                140

Thr Ser Glu Thr Val Arg Ala Val Leu Asp Ser Leu Ser Glu Lys Lys
           145                 150                155                160

Lys Ser Ser Pro Ala Ala Asp
                           165

<210> SEQ ID NO 92
<211> LENGTH: 167
<212> TYPE: PRT
<213> ORGANISM: Artificial Sequence
<220> FEATURE:
<223> OTHER INFORMATION: Description of Artificial Sequence: I-CreI
      variant

<400> SEQUENCE: 92

Met Ala Asn Thr Lys Tyr Asn Lys Glu Phe Leu Leu Tyr Leu Ala Gly
            1               5                  10                 15

Phe Val Asp Gly Asp Gly Ser Ile Ile Ala Gln Ile Lys Pro Arg Gln
                           20                 25                 30

Asp Tyr Lys Phe Lys His Gln Leu Ser Leu Thr Phe Gln Val Thr Gln
                           35                 40                 45

Lys Thr Gln Arg Arg Trp Phe Leu Asp Lys Leu Val Asp Glu Ile Gly
                           50                 55                 60

Val Gly Tyr Val Ser Asp Lys Gly Ser Val Ser Asn Tyr Ile Leu Ser
            65                 70                 75                 80

Glu Ile Lys Pro Leu His Asn Phe Leu Thr Gln Leu Gln Pro Phe Leu
                           85                 90                 95

Lys Leu Lys Gln Lys Gln Ala Asn Leu Val Leu Lys Ile Ile Glu Gln
                           100                105                110

Leu Pro Ser Ala Lys Glu Ser Pro Asp Lys Phe Leu Glu Val Cys Thr
                           115                120                125

Trp Val Asp Gln Ile Ala Ala Leu Asn Asp Ser Lys Thr Arg Lys Thr
                           130                135                140

Thr Ser Glu Thr Val Arg Ala Val Leu Asp Ser Leu Ser Glu Lys Lys
           145                 150                155                160

Lys Ser Ser Pro Ala Ala Asp
                           165

<210> SEQ ID NO 93
<211> LENGTH: 167
<212> TYPE: PRT
```

-continued

<213> ORGANISM: Artificial Sequence
<220> FEATURE:
<223> OTHER INFORMATION: Description of Artificial Sequence: I-CreI
      variant

<400> SEQUENCE: 93

Met Ala Asn Thr Lys Tyr Asn Lys Glu Phe Leu Leu Tyr Leu Ala Gly
1               5                   10                  15

Phe Val Asp Gly Asp Gly Ser Ile Ile Ala Gln Ile Arg Pro Asn Gln
            20                  25                  30

Ser Ala Lys Phe Lys His Tyr Leu Gln Leu Thr Phe Gln Val Thr Gln
        35                  40                  45

Lys Thr Gln Arg Arg Trp Phe Leu Asp Lys Leu Val Asp Glu Ile Gly
    50                  55                  60

Val Gly Tyr Val Tyr Asp Ser Gly Ser Val Ser Arg Tyr Gln Leu Ser
65                  70                  75                  80

Glu Ile Lys Pro Leu His Asn Phe Leu Thr Gln Leu Gln Pro Phe Leu
                85                  90                  95

Lys Leu Lys Gln Lys Gln Ala Asn Leu Val Leu Lys Ile Ile Glu Gln
            100                 105                 110

Leu Pro Ser Ala Lys Glu Ser Pro Asp Lys Phe Leu Glu Val Cys Thr
        115                 120                 125

Trp Val Asp Gln Ile Ala Ala Leu Asn Asp Ser Lys Thr Arg Lys Thr
    130                 135                 140

Thr Ser Glu Thr Val Arg Ala Val Leu Asp Ser Leu Ser Glu Lys Lys
145                 150                 155                 160

Lys Ser Ser Pro Ala Ala Asp
                165

<210> SEQ ID NO 94
<211> LENGTH: 167
<212> TYPE: PRT
<213> ORGANISM: Artificial Sequence
<220> FEATURE:
<223> OTHER INFORMATION: Description of Artificial Sequence: I-CreI
      variant

<400> SEQUENCE: 94

Met Ala Asn Thr Lys Tyr Asn Lys Glu Phe Leu Leu Tyr Leu Ala Gly
1               5                   10                  15

Phe Val Asp Gly Asp Gly Ser Ile Ile Ala Gln Ile Arg Pro Asp Gln
            20                  25                  30

Ser Tyr Lys Phe Lys His Gln Leu Ser Leu Thr Phe Gln Val Thr Gln
        35                  40                  45

Lys Thr Gln Arg Arg Trp Phe Leu Asp Lys Leu Val Asp Glu Ile Gly
    50                  55                  60

Val Gly Tyr Val Arg Asp Arg Gly Ser Val Ser Glu Tyr Arg Leu Ser
65                  70                  75                  80

Glu Ile Lys Pro Leu His Asn Phe Leu Thr Gln Leu Gln Pro Phe Leu
                85                  90                  95

Lys Leu Lys Gln Lys Gln Ala Asn Leu Val Leu Lys Ile Ile Glu Gln
            100                 105                 110

Leu Pro Ser Ala Lys Glu Ser Pro Asp Lys Phe Leu Glu Val Cys Thr
        115                 120                 125

Trp Val Asp Gln Ile Ala Ala Leu Asn Asp Ser Lys Thr Arg Lys Thr
    130                 135                 140

Thr Ser Glu Thr Val Arg Ala Val Leu Asp Ser Leu Ser Glu Lys Lys
145                 150                 155                 160

Lys Ser Ser Pro Ala Ala Asp
            165

<210> SEQ ID NO 95
<211> LENGTH: 167
<212> TYPE: PRT
<213> ORGANISM: Artificial Sequence
<220> FEATURE:
<223> OTHER INFORMATION: Description of Artificial Sequence: I-CreI
      variant

<400> SEQUENCE: 95

Met Ala Asn Thr Lys Tyr Asn Lys Glu Phe Leu Leu Tyr Leu Ala Gly
1               5                   10                  15

Phe Val Asp Gly Asp Gly Ser Ile Ile Ala Gln Ile Lys Pro Asn Gln
            20                  25                  30

Ser Arg Lys Phe Lys His Ala Leu Gln Leu Thr Phe Gln Val Thr Gln
        35                  40                  45

Lys Thr Gln Arg Arg Trp Phe Leu Asp Lys Leu Val Asp Glu Ile Gly
    50                  55                  60

Val Gly Tyr Val Arg Asp Ser Gly Ser Val Ser Asn Tyr Ile Leu Ser
65                  70                  75                  80

Glu Ile Lys Pro Leu His Asn Phe Leu Thr Gln Leu Gln Pro Phe Leu
                85                  90                  95

Lys Leu Lys Gln Lys Gln Ala Asn Leu Val Leu Lys Ile Ile Glu Gln
            100                 105                 110

Leu Pro Ser Ala Lys Glu Ser Pro Asp Lys Phe Leu Glu Val Cys Thr
        115                 120                 125

Trp Val Asp Gln Ile Ala Ala Leu Asn Asp Ser Lys Thr Arg Lys Thr
    130                 135                 140

Thr Ser Glu Thr Val Arg Ala Val Leu Asp Ser Leu Ser Glu Lys Lys
145                 150                 155                 160

Lys Ser Ser Pro Ala Ala Asp
            165

<210> SEQ ID NO 96
<211> LENGTH: 167
<212> TYPE: PRT
<213> ORGANISM: Artificial Sequence
<220> FEATURE:
<223> OTHER INFORMATION: Description of Artificial Sequence: I-CreI
      variant

<400> SEQUENCE: 96

Met Ala Asn Thr Lys Tyr Asn Lys Glu Phe Leu Leu Tyr Leu Ala Gly
1               5                   10                  15

Phe Val Asp Gly Asp Gly Ser Ile Ile Ala Gln Ile Lys Pro Asn Gln
            20                  25                  30

Ser Arg Lys Phe Lys His Ala Leu Gln Leu Thr Phe Asn Val Thr Gln
        35                  40                  45

Lys Thr Gln Arg Arg Trp Phe Leu Asp Lys Leu Val Asp Glu Ile Gly
    50                  55                  60

Val Gly Tyr Val Tyr Asp Ser Gly Ser Val Ser Arg Tyr Val Leu Ser
65                  70                  75                  80

Glu Ile Lys Pro Leu His Asn Phe Leu Thr Gln Leu Gln Pro Phe Leu
                85                  90                  95

Lys Leu Lys Gln Lys Gln Ala Asn Leu Val Leu Lys Ile Ile Glu Gln
            100                 105                 110

```
Leu Pro Ser Ala Lys Glu Ser Pro Asp Lys Phe Leu Glu Val Cys Thr
            115                 120                 125

Trp Val Asp Gln Ile Ala Ala Leu Asn Asp Ser Lys Thr Arg Lys Thr
    130                 135                 140

Thr Ser Glu Thr Val Arg Ala Val Leu Asp Ser Leu Ser Glu Lys Lys
145                 150                 155                 160

Lys Ser Ser Pro Ala Ala Asp
                165

<210> SEQ ID NO 97
<211> LENGTH: 167
<212> TYPE: PRT
<213> ORGANISM: Artificial Sequence
<220> FEATURE:
<223> OTHER INFORMATION: Description of Artificial Sequence: I-CreI
      variant

<400> SEQUENCE: 97

Met Ala Asn Thr Lys Tyr Asn Lys Glu Phe Leu Leu Tyr Leu Ala Gly
1               5                   10                  15

Phe Val Asp Gly Asp Gly Ser Ile Ile Ala Gln Ile Lys Pro Asn Gln
            20                  25                  30

Ser Pro Lys Phe Lys His Gln Leu Gln Leu Thr Phe Lys Val Thr Gln
        35                  40                  45

Lys Thr Gln Arg Arg Trp Phe Leu Asp Lys Leu Val Asp Glu Ile Gly
50                  55                  60

Val Gly Tyr Val Tyr Asp Ser Gly Ser Val Ser Gln Tyr Asn Leu Ser
65                  70                  75                  80

Glu Ile Lys Pro Leu His Asn Phe Leu Thr Gln Leu Gln Pro Phe Leu
                85                  90                  95

Lys Leu Lys Gln Lys Gln Ala Asn Leu Val Leu Lys Ile Ile Glu Gln
            100                 105                 110

Leu Pro Ser Ala Lys Glu Ser Pro Asp Lys Phe Leu Glu Val Cys Thr
            115                 120                 125

Trp Val Asp Gln Ile Ala Ala Leu Asn Asp Ser Lys Thr Arg Lys Thr
    130                 135                 140

Thr Ser Glu Thr Val Arg Ala Val Leu Asp Ser Leu Ser Glu Lys Lys
145                 150                 155                 160

Lys Ser Ser Pro Ala Ala Asp
                165

<210> SEQ ID NO 98
<211> LENGTH: 167
<212> TYPE: PRT
<213> ORGANISM: Artificial Sequence
<220> FEATURE:
<223> OTHER INFORMATION: Description of Artificial Sequence: I-CreI
      variant

<400> SEQUENCE: 98

Met Ala Asn Thr Lys Tyr Asn Lys Glu Phe Leu Leu Tyr Leu Ala Gly
1               5                   10                  15

Phe Val Asp Gly Asp Gly Ser Ile Ile Ala Gln Ile Ala Pro Asn Gln
            20                  25                  30

Ser Ser Lys Phe Lys His Arg Leu Lys Leu Thr Phe Gln Val Thr Gln
        35                  40                  45

Lys Thr Gln Arg Arg Trp Phe Leu Asp Lys Leu Val Asp Glu Ile Gly
50                  55                  60

Val Gly Tyr Val Asn Asp Ser Gly Ser Val Ser Asn Tyr Arg Leu Ser
```

```
                65                  70                  75                  80
Glu Ile Lys Pro Leu His Asn Phe Leu Thr Gln Leu Gln Pro Phe Leu
                    85                  90                  95

Lys Leu Lys Gln Lys Gln Ala Asn Leu Val Leu Lys Ile Ile Glu Gln
                100                 105                 110

Leu Pro Ser Ala Lys Glu Ser Pro Asp Lys Phe Leu Glu Val Cys Thr
            115                 120                 125

Trp Val Asp Gln Ile Ala Ala Leu Asn Asp Ser Lys Thr Arg Lys Thr
        130                 135                 140

Thr Ser Glu Thr Val Arg Ala Val Leu Asp Ser Leu Ser Glu Lys Lys
145                 150                 155                 160

Lys Ser Ser Pro Ala Ala Asp
                165

<210> SEQ ID NO 99
<211> LENGTH: 167
<212> TYPE: PRT
<213> ORGANISM: Artificial Sequence
<220> FEATURE:
<223> OTHER INFORMATION: Description of Artificial Sequence: I-CreI
      variant

<400> SEQUENCE: 99

Met Ala Asn Thr Lys Tyr Asn Lys Glu Phe Leu Leu Tyr Leu Ala Gly
1               5                   10                  15

Phe Val Asp Gly Asp Gly Ser Ile Ile Ala Gln Ile Lys Pro His Gln
            20                  25                  30

Ser Ser Lys Phe Lys His Gln Leu Ser Leu Thr Phe Tyr Val Thr Gln
        35                  40                  45

Lys Thr Gln Arg Arg Trp Phe Leu Asp Lys Leu Val Asp Glu Ile Gly
    50                  55                  60

Val Gly Tyr Val Arg Asp Ser Gly Ser Val Ser Asp Tyr Val Leu Ser
65                  70                  75                  80

Glu Ile Lys Pro Leu His Asn Phe Leu Thr Gln Leu Gln Pro Phe Leu
                    85                  90                  95

Lys Leu Lys Gln Lys Gln Ala Asn Leu Val Leu Lys Ile Ile Glu Gln
                100                 105                 110

Leu Pro Ser Ala Lys Glu Ser Pro Asp Lys Phe Leu Glu Val Cys Thr
            115                 120                 125

Trp Val Asp Gln Ile Ala Ala Leu Asn Asp Ser Lys Thr Arg Lys Thr
        130                 135                 140

Thr Ser Glu Thr Val Arg Ala Val Leu Asp Ser Leu Ser Glu Lys Lys
145                 150                 155                 160

Lys Ser Ser Pro Ala Ala Asp
                165

<210> SEQ ID NO 100
<211> LENGTH: 167
<212> TYPE: PRT
<213> ORGANISM: Artificial Sequence
<220> FEATURE:
<223> OTHER INFORMATION: Description of Artificial Sequence: I-CreI
      variant

<400> SEQUENCE: 100

Met Ala Asn Thr Lys Tyr Asn Lys Glu Phe Leu Leu Tyr Leu Ala Gly
1               5                   10                  15

Phe Val Asp Gly Asp Gly Ser Ile Ile Ala Gln Ile Lys Pro Asn Gln
            20                  25                  30
```

Asp His Lys Phe Lys His Gln Leu Ser Leu Thr Phe Gln Val Thr Gln
            35                  40                  45

Lys Thr Gln Arg Arg Trp Phe Leu Asp Lys Leu Val Asp Glu Ile Gly
 50                  55                  60

Val Gly Tyr Val Thr Asp Asn Gly Ser Val Ser Asn Tyr Ile Leu Ser
65                   70                  75                  80

Glu Ile Lys Pro Leu His Asn Phe Leu Thr Gln Leu Gln Pro Phe Leu
                 85                  90                  95

Lys Leu Lys Gln Lys Gln Ala Asn Leu Val Leu Lys Ile Ile Glu Gln
                100                 105                 110

Leu Pro Ser Ala Lys Glu Ser Pro Asp Lys Phe Leu Glu Val Cys Thr
                115                 120                 125

Trp Val Asp Gln Ile Ala Ala Leu Asn Asp Ser Lys Thr Arg Lys Thr
            130                 135                 140

Thr Ser Glu Thr Val Arg Ala Val Leu Asp Ser Leu Ser Glu Lys Lys
145                 150                 155                 160

Lys Ser Ser Pro Ala Ala Asp
                165

<210> SEQ ID NO 101
<211> LENGTH: 167
<212> TYPE: PRT
<213> ORGANISM: Artificial Sequence
<220> FEATURE:
<223> OTHER INFORMATION: Description of Artificial Sequence: I-CreI
      variant

<400> SEQUENCE: 101

Met Ala Asn Thr Lys Tyr Asn Lys Glu Phe Leu Leu Tyr Leu Ala Gly
1               5                   10                  15

Phe Val Asp Gly Asp Gly Ser Ile Ile Ala Gln Ile Lys Pro Asn Gln
            20                  25                  30

Arg Asp Lys Phe Lys His Gln Leu Ser Leu Thr Phe Ala Val Thr Gln
            35                  40                  45

Lys Thr Gln Arg Arg Trp Phe Leu Asp Lys Leu Val Asp Glu Ile Gly
 50                  55                  60

Val Gly Tyr Val Arg Asp Ser Gly Ser Val Ser Asn Tyr Ile Leu Ser
65                   70                  75                  80

Glu Ile Lys Pro Leu His Asn Phe Leu Thr Gln Leu Gln Pro Phe Leu
                 85                  90                  95

Lys Leu Lys Gln Lys Gln Ala Asn Leu Val Leu Lys Ile Ile Glu Gln
                100                 105                 110

Leu Pro Ser Ala Lys Glu Ser Pro Asp Lys Phe Leu Glu Val Cys Thr
                115                 120                 125

Trp Val Asp Gln Ile Ala Ala Leu Asn Asp Ser Lys Thr Arg Lys Thr
            130                 135                 140

Thr Ser Glu Thr Val Arg Ala Val Leu Asp Ser Leu Ser Glu Lys Lys
145                 150                 155                 160

Lys Ser Ser Pro Ala Ala Asp
                165

<210> SEQ ID NO 102
<211> LENGTH: 167
<212> TYPE: PRT
<213> ORGANISM: Artificial Sequence
<220> FEATURE:
<223> OTHER INFORMATION: Description of Artificial Sequence: I-CreI
      variant

<400> SEQUENCE: 102

```
Met Ala Asn Thr Lys Tyr Asn Lys Glu Phe Leu Leu Tyr Leu Ala Gly
1               5                   10                  15

Phe Val Asp Gly Asp Gly Ser Ile Ile Ala Gln Ile Lys Pro Asn Gln
            20                  25                  30

Ser Pro Lys Phe Lys His Gln Leu Gln Leu Thr Phe Lys Val Thr Gln
        35                  40                  45

Lys Thr Gln Arg Arg Trp Phe Leu Asp Lys Leu Val Asp Glu Ile Gly
    50                  55                  60

Val Gly Tyr Val Tyr Asp Ser Gly Ser Val Ser Gln Tyr Asn Leu Ser
65                  70                  75                  80

Glu Ile Lys Pro Leu His Asn Phe Leu Thr Gln Leu Gln Pro Phe Leu
                85                  90                  95

Lys Leu Lys Gln Lys Gln Ala Asn Leu Val Leu Lys Ile Ile Glu Gln
                100                 105                 110

Leu Pro Ser Ala Lys Glu Ser Pro Asp Lys Phe Leu Glu Val Cys Thr
            115                 120                 125

Trp Val Asp Gln Ile Ala Ala Leu Asn Asp Ser Lys Thr Arg Lys Thr
        130                 135                 140

Thr Ser Glu Thr Val Arg Ala Val Leu Asp Ser Leu Ser Glu Lys Lys
145                 150                 155                 160

Lys Ser Ser Pro Ala Ala Asp
                165
```

<210> SEQ ID NO 103
<211> LENGTH: 167
<212> TYPE: PRT
<213> ORGANISM: Artificial Sequence
<220> FEATURE:
<223> OTHER INFORMATION: Description of Artificial Sequence: I-CreI variant

<400> SEQUENCE: 103

```
Met Ala Asn Thr Lys Tyr Asn Lys Glu Phe Leu Leu Tyr Leu Ala Gly
1               5                   10                  15

Phe Val Asp Gly Asp Gly Ser Ile Ile Ala Gln Ile Gln Pro Asn Gln
            20                  25                  30

Ser Tyr Lys Phe Lys His Arg Leu Lys Leu Thr Phe Ala Val Thr Gln
        35                  40                  45

Lys Thr Gln Arg Arg Trp Phe Leu Asp Lys Leu Val Asp Glu Ile Gly
    50                  55                  60

Val Gly Tyr Val Arg Asp Ser Gly Ser Val Ser Glu Tyr Arg Leu Ser
65                  70                  75                  80

Glu Ile Lys Pro Leu His Asn Phe Leu Thr Gln Leu Gln Pro Phe Leu
                85                  90                  95

Lys Leu Lys Gln Lys Gln Ala Asn Leu Val Leu Lys Ile Ile Glu Gln
                100                 105                 110

Leu Pro Ser Ala Lys Glu Ser Pro Asp Lys Phe Leu Glu Val Cys Thr
            115                 120                 125

Trp Val Asp Gln Ile Ala Ala Leu Asn Asp Ser Lys Thr Arg Lys Thr
        130                 135                 140

Thr Ser Glu Thr Val Arg Ala Val Leu Asp Ser Leu Ser Glu Lys Lys
145                 150                 155                 160

Lys Ser Ser Pro Ala Ala Asp
                165
```

<210> SEQ ID NO 104
<211> LENGTH: 167
<212> TYPE: PRT
<213> ORGANISM: Artificial Sequence
<220> FEATURE:
<223> OTHER INFORMATION: Description of Artificial Sequence: I-CreI variant

<400> SEQUENCE: 104

Met Ala Asn Thr Lys Tyr Asn Lys Glu Phe Leu Leu Tyr Leu Ala Gly
1               5                   10                  15

Phe Val Asp Gly Asp Gly Ser Ile Ile Ala Gln Ile Lys Pro Asn Gln
            20                  25                  30

Ser Thr Lys Phe Lys His Ala Leu Ser Leu Thr Phe Gln Val Thr Gln
        35                  40                  45

Lys Thr Gln Arg Arg Trp Phe Leu Asp Lys Leu Val Asp Glu Ile Gly
    50                  55                  60

Val Gly Tyr Val His Asp His Gly Ser Val Ser Asn Tyr Ile Leu Ser
65                  70                  75                  80

Glu Ile Lys Pro Leu His Asn Phe Leu Thr Gln Leu Gln Pro Phe Leu
                85                  90                  95

Lys Leu Lys Gln Lys Gln Ala Asn Leu Val Leu Lys Ile Ile Glu Gln
            100                 105                 110

Leu Pro Ser Ala Lys Glu Ser Pro Asp Lys Phe Leu Glu Val Cys Thr
        115                 120                 125

Trp Val Asp Gln Ile Ala Ala Leu Asn Asp Ser Lys Thr Arg Lys Thr
    130                 135                 140

Thr Ser Glu Thr Val Arg Ala Val Leu Asp Ser Leu Ser Glu Lys Lys
145                 150                 155                 160

Lys Ser Ser Pro Ala Ala Asp
                165

<210> SEQ ID NO 105
<211> LENGTH: 167
<212> TYPE: PRT
<213> ORGANISM: Artificial Sequence
<220> FEATURE:
<223> OTHER INFORMATION: Description of Artificial Sequence: I-CreI variant

<400> SEQUENCE: 105

Met Ala Asn Thr Lys Tyr Asn Lys Glu Phe Leu Leu Tyr Leu Ala Gly
1               5                   10                  15

Phe Val Asp Gly Asp Gly Ser Ile Ile Ala Gln Ile Lys Pro Asn Gln
            20                  25                  30

Ser Thr Lys Phe Lys His Gln Leu Thr Leu Thr Phe Gln Val Thr Gln
        35                  40                  45

Lys Thr Gln Arg Arg Trp Phe Leu Asp Lys Leu Val Asp Glu Ile Gly
    50                  55                  60

Val Gly Tyr Val Ala Asp Lys Gly Ser Val Ser Asn Tyr Ile Leu Ser
65                  70                  75                  80

Glu Ile Lys Pro Leu His Asn Phe Leu Thr Gln Leu Gln Pro Phe Leu
                85                  90                  95

Lys Leu Lys Gln Lys Gln Ala Asn Leu Val Leu Lys Ile Ile Glu Gln
            100                 105                 110

Leu Pro Ser Ala Lys Glu Ser Pro Asp Lys Phe Leu Glu Val Cys Thr
        115                 120                 125

Trp Val Asp Gln Ile Ala Ala Leu Asn Asp Ser Lys Thr Arg Lys Thr

Thr Ser Glu Thr Val Arg Ala Val Leu Asp Ser Leu Ser Glu Lys Lys
145                 150                 155                 160

Lys Ser Ser Pro Ala Ala Asp
                165

<210> SEQ ID NO 106
<211> LENGTH: 167
<212> TYPE: PRT
<213> ORGANISM: Artificial Sequence
<220> FEATURE:
<223> OTHER INFORMATION: Description of Artificial Sequence: I-CreI
      variant

<400> SEQUENCE: 106

Met Ala Asn Thr Lys Tyr Asn Lys Glu Phe Leu Leu Tyr Leu Ala Gly
1               5                   10                  15

Phe Val Asp Gly Asp Gly Ser Ile Ile Ala Gln Ile Lys Pro Asn Gln
                20                  25                  30

Asp His Lys Phe Lys His Gln Leu Ser Leu Thr Phe Asn Val Thr Gln
            35                  40                  45

Lys Thr Gln Arg Arg Trp Phe Leu Asp Lys Leu Val Asp Glu Ile Gly
        50                  55                  60

Val Gly Tyr Val Arg Asp Ser Gly Ser Val Ser Arg Tyr Asp Leu Ser
65                  70                  75                  80

Glu Ile Lys Pro Leu His Asn Phe Leu Thr Gln Leu Gln Pro Phe Leu
                85                  90                  95

Lys Leu Lys Gln Lys Gln Ala Asn Leu Val Leu Lys Ile Ile Glu Gln
            100                 105                 110

Leu Pro Ser Ala Lys Glu Ser Pro Asp Lys Phe Leu Glu Val Cys Thr
        115                 120                 125

Trp Val Asp Gln Ile Ala Ala Leu Asn Asp Ser Lys Thr Arg Lys Thr
    130                 135                 140

Thr Ser Glu Thr Val Arg Ala Val Leu Asp Ser Leu Ser Glu Lys Lys
145                 150                 155                 160

Lys Ser Ser Pro Ala Ala Asp
                165

<210> SEQ ID NO 107
<211> LENGTH: 167
<212> TYPE: PRT
<213> ORGANISM: Artificial Sequence
<220> FEATURE:
<223> OTHER INFORMATION: Description of Artificial Sequence: I-CreI
      variant

<400> SEQUENCE: 107

Met Ala Asn Thr Lys Tyr Asn Lys Glu Phe Leu Leu Tyr Leu Ala Gly
1               5                   10                  15

Phe Val Asp Gly Asp Gly Ser Ile Ile Ala Gln Ile Lys Pro Asp Gln
                20                  25                  30

Ser Arg Lys Phe Lys His Thr Leu Ser Leu Thr Phe Lys Val Thr Gln
            35                  40                  45

Lys Thr Gln Arg Arg Trp Phe Leu Asp Lys Leu Val Asp Glu Ile Gly
        50                  55                  60

Val Gly Tyr Val Glu Asp Ser Gly Ser Val Ser Asp Tyr Arg Leu Ser
65                  70                  75                  80

Glu Ile Lys Pro Leu His Asn Phe Leu Thr Gln Leu Gln Pro Phe Leu
                85                  90                  95

```
Lys Leu Lys Gln Lys Gln Ala Asn Leu Val Leu Lys Ile Ile Glu Gln
            100                 105                 110

Leu Pro Ser Ala Lys Glu Ser Pro Asp Lys Phe Leu Glu Val Cys Thr
            115                 120                 125

Trp Val Asp Gln Ile Ala Ala Leu Asn Asp Ser Lys Thr Arg Lys Thr
        130                 135                 140

Thr Ser Glu Thr Val Arg Ala Val Leu Asp Ser Leu Ser Glu Lys Lys
145                 150                 155                 160

Lys Ser Ser Pro Ala Ala Asp
                165

<210> SEQ ID NO 108
<211> LENGTH: 167
<212> TYPE: PRT
<213> ORGANISM: Artificial Sequence
<220> FEATURE:
<223> OTHER INFORMATION: Description of Artificial Sequence: I-CreI
      variant

<400> SEQUENCE: 108

Met Ala Asn Thr Lys Tyr Asn Lys Glu Phe Leu Leu Tyr Leu Ala Gly
1               5                   10                  15

Phe Val Asp Gly Asp Gly Ser Ile Ile Ala Gln Ile Lys Pro Asn Gln
            20                  25                  30

Thr Tyr Lys Phe Lys His Trp Leu Ser Leu Thr Phe Lys Val Thr Gln
        35                  40                  45

Lys Thr Gln Arg Arg Trp Phe Leu Asp Lys Leu Val Asp Glu Ile Gly
50                  55                  60

Val Gly Tyr Val Glu Asp Ser Gly Ser Val Ser Asp Tyr Arg Leu Ser
65                  70                  75                  80

Glu Ile Lys Pro Leu His Asn Phe Leu Thr Gln Leu Gln Pro Phe Leu
                85                  90                  95

Lys Leu Lys Gln Lys Gln Ala Asn Leu Val Leu Lys Ile Ile Glu Gln
            100                 105                 110

Leu Pro Ser Ala Lys Glu Ser Pro Asp Lys Phe Leu Glu Val Cys Thr
            115                 120                 125

Trp Val Asp Gln Ile Ala Ala Leu Asn Asp Ser Lys Thr Arg Lys Thr
        130                 135                 140

Thr Ser Glu Thr Val Arg Ala Val Leu Asp Ser Leu Ser Glu Lys Lys
145                 150                 155                 160

Lys Ser Ser Pro Ala Ala Asp
                165

<210> SEQ ID NO 109
<211> LENGTH: 167
<212> TYPE: PRT
<213> ORGANISM: Artificial Sequence
<220> FEATURE:
<223> OTHER INFORMATION: Description of Artificial Sequence: I-CreI
      variant

<400> SEQUENCE: 109

Met Ala Asn Thr Lys Tyr Asn Lys Glu Phe Leu Leu Tyr Leu Ala Gly
1               5                   10                  15

Phe Val Asp Gly Asp Gly Ser Ile Ile Ala Gln Ile Lys Pro His Gln
            20                  25                  30

Ser Ser Lys Phe Lys His Gln Leu Ser Leu Thr Phe Ala Val Thr Gln
        35                  40                  45
```

```
Lys Thr Gln Arg Arg Trp Phe Leu Asp Lys Leu Val Asp Glu Ile Gly
         50                  55                  60

Val Gly Tyr Val Arg Asp Ser Gly Ser Val Ser Gln Tyr Glu Leu Ser
 65                  70                  75                  80

Glu Ile Lys Pro Leu His Asn Phe Leu Thr Gln Leu Gln Pro Phe Leu
                 85                  90                  95

Lys Leu Lys Gln Lys Gln Ala Asn Leu Val Leu Lys Ile Ile Glu Gln
                100                 105                 110

Leu Pro Ser Ala Lys Glu Ser Pro Asp Lys Phe Leu Glu Val Cys Thr
                115                 120                 125

Trp Val Asp Gln Ile Ala Ala Leu Asn Asp Ser Lys Thr Arg Lys Thr
        130                 135                 140

Thr Ser Glu Thr Val Arg Ala Val Leu Asp Ser Leu Ser Glu Lys Lys
145                 150                 155                 160

Lys Ser Ser Pro Ala Ala Asp
                165
```

<210> SEQ ID NO 110
<211> LENGTH: 167
<212> TYPE: PRT
<213> ORGANISM: Artificial Sequence
<220> FEATURE:
<223> OTHER INFORMATION: Description of Artificial Sequence: I-CreI variant

<400> SEQUENCE: 110

```
Met Ala Asn Thr Lys Tyr Asn Lys Glu Phe Leu Leu Tyr Leu Ala Gly
 1               5                  10                  15

Phe Val Asp Gly Asp Gly Ser Ile Ile Ala Gln Ile Lys Pro Asn Gln
                 20                  25                  30

Ser Cys Lys Phe Lys His Ala Leu Ser Leu Thr Phe Gln Val Thr Gln
                 35                  40                  45

Lys Thr Gln Arg Arg Trp Phe Leu Asp Lys Leu Val Asp Glu Ile Gly
         50                  55                  60

Val Gly Tyr Val Ala Asp Lys Gly Ser Val Ser Asn Tyr Ile Leu Ser
 65                  70                  75                  80

Glu Ile Lys Pro Leu His Asn Phe Leu Thr Gln Leu Gln Pro Phe Leu
                 85                  90                  95

Lys Leu Lys Gln Lys Gln Ala Asn Leu Val Leu Lys Ile Ile Glu Gln
                100                 105                 110

Leu Pro Ser Ala Lys Glu Ser Pro Asp Lys Phe Leu Glu Val Cys Thr
                115                 120                 125

Trp Val Asp Gln Ile Ala Ala Leu Asn Asp Ser Lys Thr Arg Lys Thr
        130                 135                 140

Thr Ser Glu Thr Val Arg Ala Val Leu Asp Ser Leu Ser Glu Lys Lys
145                 150                 155                 160

Lys Ser Ser Pro Ala Ala Asp
                165
```

<210> SEQ ID NO 111
<211> LENGTH: 167
<212> TYPE: PRT
<213> ORGANISM: Artificial Sequence
<220> FEATURE:
<223> OTHER INFORMATION: Description of Artificial Sequence: I-CreI variant

<400> SEQUENCE: 111

```
Met Ala Asn Thr Lys Tyr Asn Lys Glu Phe Leu Leu Tyr Leu Ala Gly
```

```
                1               5                  10                 15
Phe Val Asp Gly Asp Gly Ser Ile Ile Ala Gln Ile Lys Pro Asn Gln
                20                  25                 30

Asp Tyr Lys Phe Lys His Cys Leu Ser Leu Thr Phe Asp Val Thr Gln
                35                  40                 45

Lys Thr Gln Arg Arg Trp Phe Leu Asp Lys Leu Val Asp Glu Ile Gly
            50                  55                 60

Val Gly Tyr Val Tyr Asp Ser Gly Ser Val Ser Ser Tyr Arg Leu Ser
65                  70                  75                 80

Glu Ile Lys Pro Leu His Asn Phe Leu Thr Gln Leu Gln Pro Phe Leu
                85                  90                 95

Lys Leu Lys Gln Lys Gln Ala Asn Leu Val Leu Lys Ile Ile Glu Gln
                100                 105                110

Leu Pro Ser Ala Lys Glu Ser Pro Asp Lys Phe Leu Glu Val Cys Thr
                115                 120                125

Trp Val Asp Gln Ile Ala Ala Leu Asn Asp Ser Lys Thr Arg Lys Thr
            130                 135                140

Thr Ser Glu Thr Val Arg Ala Val Leu Asp Ser Leu Ser Glu Lys Lys
145                 150                 155                160

Lys Ser Ser Pro Ala Ala Asp
                165

<210> SEQ ID NO 112
<211> LENGTH: 167
<212> TYPE: PRT
<213> ORGANISM: Artificial Sequence
<220> FEATURE:
<223> OTHER INFORMATION: Description of Artificial Sequence: I-CreI
      variant

<400> SEQUENCE: 112

Met Ala Asn Thr Lys Tyr Asn Lys Glu Phe Leu Leu Tyr Leu Ala Gly
1               5                   10                 15

Phe Val Asp Gly Asp Gly Ser Ile Ile Ala Gln Ile Lys Pro Asn Gln
                20                  25                 30

Thr Tyr Lys Phe Lys His Trp Leu Ser Leu Thr Phe Lys Val Thr Gln
                35                  40                 45

Lys Thr Gln Arg Arg Trp Phe Leu Asp Lys Leu Val Asp Glu Ile Gly
            50                  55                 60

Val Gly Tyr Val Arg Asp Glu Gly Ser Val Ser Asn Tyr Ile Leu Ser
65                  70                  75                 80

Glu Ile Lys Pro Leu His Asn Phe Leu Thr Gln Leu Gln Pro Phe Leu
                85                  90                 95

Lys Leu Lys Gln Lys Gln Ala Asn Leu Val Leu Lys Ile Ile Glu Gln
                100                 105                110

Leu Pro Ser Ala Lys Glu Ser Pro Asp Lys Phe Leu Glu Val Cys Thr
                115                 120                125

Trp Val Asp Gln Ile Ala Ala Leu Asn Asp Ser Lys Thr Arg Lys Thr
            130                 135                140

Thr Ser Glu Thr Val Arg Ala Val Leu Asp Ser Leu Ser Glu Lys Lys
145                 150                 155                160

Lys Ser Ser Pro Ala Ala Asp
                165

<210> SEQ ID NO 113
<211> LENGTH: 167
<212> TYPE: PRT
```

<213> ORGANISM: Artificial Sequence
<220> FEATURE:
<223> OTHER INFORMATION: Description of Artificial Sequence: I-CreI
    variant

<400> SEQUENCE: 113

Met Ala Asn Thr Lys Tyr Asn Lys Glu Phe Leu Leu Tyr Leu Ala Gly
1               5                   10                  15

Phe Val Asp Gly Asp Gly Ser Ile Ile Ala Gln Ile Lys Pro Asn Gln
            20                  25                  30

Ser Arg Lys Phe Lys His Ala Leu Gln Leu Thr Phe Ala Val Thr Gln
        35                  40                  45

Lys Thr Gln Arg Arg Trp Phe Leu Asp Lys Leu Val Asp Glu Ile Gly
    50                  55                  60

Val Gly Tyr Val Arg Asp Ser Gly Ser Val Ser Asn Tyr Ile Leu Ser
65                  70                  75                  80

Glu Ile Lys Pro Leu His Asn Phe Leu Thr Gln Leu Gln Pro Phe Leu
                85                  90                  95

Lys Leu Lys Gln Lys Gln Ala Asn Leu Val Leu Lys Ile Ile Glu Gln
            100                 105                 110

Leu Pro Ser Ala Lys Glu Ser Pro Asp Lys Phe Leu Glu Val Cys Thr
        115                 120                 125

Trp Val Asp Gln Ile Ala Ala Leu Asn Asp Ser Lys Thr Arg Lys Thr
    130                 135                 140

Thr Ser Glu Thr Val Arg Ala Val Leu Asp Ser Leu Ser Glu Lys Lys
145                 150                 155                 160

Lys Ser Ser Pro Ala Ala Asp
                165

<210> SEQ ID NO 114
<211> LENGTH: 167
<212> TYPE: PRT
<213> ORGANISM: Artificial Sequence
<220> FEATURE:
<223> OTHER INFORMATION: Description of Artificial Sequence: I-CreI
    variant

<400> SEQUENCE: 114

Met Ala Asn Thr Lys Tyr Asn Lys Glu Phe Leu Leu Tyr Leu Ala Gly
1               5                   10                  15

Phe Val Asp Gly Asp Gly Ser Ile Ile Ala Gln Ile Lys Pro Asn Gln
            20                  25                  30

Ser His Lys Phe Lys His Ser Leu Ser Leu Thr Phe Lys Val Thr Gln
        35                  40                  45

Lys Thr Gln Arg Arg Trp Phe Leu Asp Lys Leu Val Asp Glu Ile Gly
    50                  55                  60

Val Gly Tyr Val Tyr Asp Ser Gly Ser Val Ser Gln Tyr Asn Leu Ser
65                  70                  75                  80

Glu Ile Lys Pro Leu His Asn Phe Leu Thr Gln Leu Gln Pro Phe Leu
                85                  90                  95

Lys Leu Lys Gln Lys Gln Ala Asn Leu Val Leu Lys Ile Ile Glu Gln
            100                 105                 110

Leu Pro Ser Ala Lys Glu Ser Pro Asp Lys Phe Leu Glu Val Cys Thr
        115                 120                 125

Trp Val Asp Gln Ile Ala Ala Leu Asn Asp Ser Lys Thr Arg Lys Thr
    130                 135                 140

Thr Ser Glu Thr Val Arg Ala Val Leu Asp Ser Leu Ser Glu Lys Lys
145                 150                 155                 160

Lys Ser Ser Pro Ala Ala Asp
            165

<210> SEQ ID NO 115
<211> LENGTH: 167
<212> TYPE: PRT
<213> ORGANISM: Artificial Sequence
<220> FEATURE:
<223> OTHER INFORMATION: Description of Artificial Sequence: I-CreI
      variant

<400> SEQUENCE: 115

Met Ala Asn Thr Lys Tyr Asn Lys Glu Phe Leu Leu Tyr Leu Ala Gly
1               5                   10                  15

Phe Val Asp Gly Asp Gly Ser Ile Ile Ala Gln Ile Lys Pro Asn Gln
            20                  25                  30

Thr Cys Lys Phe Lys His Gln Leu Ser Leu Thr Phe Ala Val Thr Gln
        35                  40                  45

Lys Thr Gln Arg Arg Trp Phe Leu Asp Lys Leu Val Asp Glu Ile Gly
    50                  55                  60

Val Gly Tyr Val Arg Asp Ser Gly Ser Val Ser Asn Tyr Ile Leu Ser
65                  70                  75                  80

Glu Ile Lys Pro Leu His Asn Phe Leu Thr Gln Leu Gln Pro Phe Leu
                85                  90                  95

Lys Leu Lys Gln Lys Gln Ala Asn Leu Val Leu Lys Ile Ile Glu Gln
            100                 105                 110

Leu Pro Ser Ala Lys Glu Ser Pro Asp Lys Phe Leu Glu Val Cys Thr
        115                 120                 125

Trp Val Asp Gln Ile Ala Ala Leu Asn Asp Ser Lys Thr Arg Lys Thr
    130                 135                 140

Thr Ser Glu Thr Val Arg Ala Val Leu Asp Ser Leu Ser Glu Lys Lys
145                 150                 155                 160

Lys Ser Ser Pro Ala Ala Asp
            165

<210> SEQ ID NO 116
<211> LENGTH: 167
<212> TYPE: PRT
<213> ORGANISM: Artificial Sequence
<220> FEATURE:
<223> OTHER INFORMATION: Description of Artificial Sequence: I-CreI
      variant

<400> SEQUENCE: 116

Met Ala Asn Thr Lys Tyr Asn Lys Glu Phe Leu Leu Tyr Leu Ala Gly
1               5                   10                  15

Phe Val Asp Gly Asp Gly Ser Ile Ile Ala Gln Ile Lys Pro Asn Gln
            20                  25                  30

Asp His Lys Phe Lys His Gln Leu Ser Leu Thr Phe Asp Val Thr Gln
        35                  40                  45

Lys Thr Gln Arg Arg Trp Phe Leu Asp Lys Leu Val Asp Glu Ile Gly
    50                  55                  60

Val Gly Tyr Val Asn Asp Ser Gly Ser Val Ser Asn Tyr Ile Leu Ser
65                  70                  75                  80

Glu Ile Lys Pro Leu His Asn Phe Leu Thr Gln Leu Gln Pro Phe Leu
                85                  90                  95

Lys Leu Lys Gln Lys Gln Ala Asn Leu Val Leu Lys Ile Ile Glu Gln
            100                 105                 110

```
Leu Pro Ser Ala Lys Glu Ser Pro Asp Lys Phe Leu Glu Val Cys Thr
        115                 120                 125
Trp Val Asp Gln Ile Ala Ala Leu Asn Asp Ser Lys Thr Arg Lys Thr
    130                 135                 140
Thr Ser Glu Thr Val Arg Ala Val Leu Asp Ser Leu Ser Glu Lys Lys
145                 150                 155                 160
Lys Ser Ser Pro Ala Ala Asp
                165

<210> SEQ ID NO 117
<211> LENGTH: 167
<212> TYPE: PRT
<213> ORGANISM: Artificial Sequence
<220> FEATURE:
<223> OTHER INFORMATION: Description of Artificial Sequence: I-CreI
      variant

<400> SEQUENCE: 117

Met Ala Asn Thr Lys Tyr Asn Lys Glu Phe Leu Leu Tyr Leu Ala Gly
1               5                   10                  15
Phe Val Asp Gly Asp Gly Ser Ile Ile Ala Gln Ile Lys Pro Asn Gln
            20                  25                  30
Ser Arg Lys Phe Lys His Ala Leu Gln Leu Thr Phe Gln Val Thr Gln
        35                  40                  45
Lys Thr Gln Arg Arg Trp Phe Leu Asp Lys Leu Val Asp Glu Ile Gly
    50                  55                  60
Val Gly Tyr Val Arg Asp Ser Gly Ser Val Ser Asp Tyr Lys Leu Ser
65                  70                  75                  80
Glu Ile Lys Pro Leu His Asn Phe Leu Thr Gln Leu Gln Pro Phe Leu
                85                  90                  95
Lys Leu Lys Gln Lys Gln Ala Asn Leu Val Leu Lys Ile Ile Glu Gln
            100                 105                 110
Leu Pro Ser Ala Lys Glu Ser Pro Asp Lys Phe Leu Glu Val Cys Thr
        115                 120                 125
Trp Val Asp Gln Ile Ala Ala Leu Asn Asp Ser Lys Thr Arg Lys Thr
    130                 135                 140
Thr Ser Glu Thr Val Arg Ala Val Leu Asp Ser Leu Ser Glu Lys Lys
145                 150                 155                 160
Lys Ser Ser Pro Ala Ala Asp
                165

<210> SEQ ID NO 118
<211> LENGTH: 167
<212> TYPE: PRT
<213> ORGANISM: Artificial Sequence
<220> FEATURE:
<223> OTHER INFORMATION: Description of Artificial Sequence: I-CreI
      variant

<400> SEQUENCE: 118

Met Ala Asn Thr Lys Tyr Asn Lys Glu Phe Leu Leu Tyr Leu Ala Gly
1               5                   10                  15
Phe Val Asp Gly Asp Gly Ser Ile Ile Ala Gln Ile Lys Pro Asn Gln
            20                  25                  30
Asp Tyr Lys Phe Lys His Cys Leu Ser Leu Thr Phe Ala Val Thr Gln
        35                  40                  45
Lys Thr Gln Arg Arg Trp Phe Leu Asp Lys Leu Val Asp Glu Ile Gly
    50                  55                  60
Val Gly Tyr Val Arg Asp Ser Gly Ser Val Ser Arg Tyr Tyr Leu Ser
```

```
                65                  70                  75                  80
Glu Ile Lys Pro Leu His Asn Phe Leu Thr Gln Leu Gln Pro Phe Leu
                85                  90                  95

Lys Leu Lys Gln Lys Gln Ala Asn Leu Val Leu Lys Ile Ile Glu Gln
            100                 105                 110

Leu Pro Ser Ala Lys Glu Ser Pro Asp Lys Phe Leu Glu Val Cys Thr
        115                 120                 125

Trp Val Asp Gln Ile Ala Ala Leu Asn Asp Ser Lys Thr Arg Lys Thr
    130                 135                 140

Thr Ser Glu Thr Val Arg Ala Val Leu Asp Ser Leu Ser Glu Lys Lys
145                 150                 155                 160

Lys Ser Ser Pro Ala Ala Asp
                165

<210> SEQ ID NO 119
<211> LENGTH: 167
<212> TYPE: PRT
<213> ORGANISM: Artificial Sequence
<220> FEATURE:
<223> OTHER INFORMATION: Description of Artificial Sequence: I-CreI
      variant

<400> SEQUENCE: 119

Met Ala Asn Thr Lys Tyr Asn Lys Glu Phe Leu Leu Tyr Leu Ala Gly
1               5                   10                  15

Phe Val Asp Gly Asp Gly Ser Ile Ile Ala Gln Ile Lys Pro Asn Gln
            20                  25                  30

Ser Tyr Lys Phe Lys His Gln Leu Ser Leu Thr Phe Gln Val Thr Gln
        35                  40                  45

Lys Thr Gln Arg Arg Trp Phe Leu Asp Lys Leu Val Asp Glu Ile Gly
    50                  55                  60

Val Gly Tyr Val Arg Asp Ser Gly Ser Val Ser Tyr Arg Leu Ser
65                  70                  75                  80

Glu Ile Lys Pro Leu His Asn Phe Leu Thr Gln Leu Gln Pro Phe Leu
                85                  90                  95

Lys Leu Lys Gln Lys Gln Ala Asn Leu Val Leu Lys Ile Ile Glu Gln
            100                 105                 110

Leu Pro Ser Ala Lys Glu Ser Pro Asp Lys Phe Leu Glu Val Cys Thr
        115                 120                 125

Trp Val Asp Gln Ile Ala Ala Leu Asn Asp Ser Lys Thr Arg Lys Thr
    130                 135                 140

Thr Ser Glu Thr Val Arg Ala Val Leu Asp Ser Leu Ser Glu Lys Lys
145                 150                 155                 160

Lys Ser Ser Pro Ala Ala Asp
                165

<210> SEQ ID NO 120
<211> LENGTH: 167
<212> TYPE: PRT
<213> ORGANISM: Artificial Sequence
<220> FEATURE:
<223> OTHER INFORMATION: Description of Artificial Sequence: I-CreI
      variant

<400> SEQUENCE: 120

Met Ala Asn Thr Lys Tyr Asn Lys Glu Phe Leu Leu Tyr Leu Ala Gly
1               5                   10                  15

Phe Val Asp Gly Asp Gly Ser Ile Ile Ala Gln Ile Lys Pro Arg Gln
            20                  25                  30
```

```
Asp Tyr Lys Phe Lys His Gln Leu Ser Leu Thr Phe Thr Val Thr Gln
            35                  40                  45

Lys Thr Gln Arg Arg Trp Phe Leu Asp Lys Leu Val Asp Glu Ile Gly
 50                  55                  60

Val Gly Tyr Val His Asp His Gly Ser Val Ser Asn Tyr Ile Leu Ser
 65                  70                  75                  80

Glu Ile Lys Pro Leu His Asn Phe Leu Thr Gln Leu Gln Pro Phe Leu
                 85                  90                  95

Lys Leu Lys Gln Lys Gln Ala Asn Leu Val Leu Lys Ile Ile Glu Gln
                100                 105                 110

Leu Pro Ser Ala Lys Glu Ser Pro Asp Lys Phe Leu Glu Val Cys Thr
            115                 120                 125

Trp Val Asp Gln Ile Ala Ala Leu Asn Asp Ser Lys Thr Arg Lys Thr
            130                 135                 140

Thr Ser Glu Thr Val Arg Ala Val Leu Asp Ser Leu Ser Glu Lys Lys
145                 150                 155                 160

Lys Ser Ser Pro Ala Ala Asp
                165

<210> SEQ ID NO 121
<211> LENGTH: 167
<212> TYPE: PRT
<213> ORGANISM: Artificial Sequence
<220> FEATURE:
<223> OTHER INFORMATION: Description of Artificial Sequence: I-CreI
      variant

<400> SEQUENCE: 121

Met Ala Asn Thr Lys Tyr Asn Lys Glu Phe Leu Leu Tyr Leu Ala Gly
 1               5                  10                  15

Phe Val Asp Gly Asp Gly Ser Ile Ile Ala Gln Ile Lys Pro Asn Gln
                20                  25                  30

Ala Cys Lys Phe Lys His Gln Leu Ser Leu Thr Phe Gln Val Thr Gln
            35                  40                  45

Lys Thr Gln Arg Arg Trp Phe Leu Asp Lys Leu Val Asp Glu Ile Gly
 50                  55                  60

Val Gly Tyr Val Tyr Asp Ser Gly Ser Val Ser Arg Tyr Gln Leu Ser
 65                  70                  75                  80

Glu Ile Lys Pro Leu His Asn Phe Leu Thr Gln Leu Gln Pro Phe Leu
                 85                  90                  95

Lys Leu Lys Gln Lys Gln Ala Asn Leu Val Leu Lys Ile Ile Glu Gln
                100                 105                 110

Leu Pro Ser Ala Lys Glu Ser Pro Asp Lys Phe Leu Glu Val Cys Thr
            115                 120                 125

Trp Val Asp Gln Ile Ala Ala Leu Asn Asp Ser Lys Thr Arg Lys Thr
            130                 135                 140

Thr Ser Glu Thr Val Arg Ala Val Leu Asp Ser Leu Ser Glu Lys Lys
145                 150                 155                 160

Lys Ser Ser Pro Ala Ala Asp
                165

<210> SEQ ID NO 122
<211> LENGTH: 167
<212> TYPE: PRT
<213> ORGANISM: Artificial Sequence
<220> FEATURE:
<223> OTHER INFORMATION: Description of Artificial Sequence: I-CreI
      variant
```

-continued

```
<400> SEQUENCE: 122

Met Ala Asn Thr Lys Tyr Asn Lys Glu Phe Leu Leu Tyr Leu Ala Gly
1               5                   10                  15

Phe Val Asp Gly Asp Gly Ser Ile Ile Ala Gln Ile Lys Pro Asn Gln
            20                  25                  30

Asn Gly Lys Phe Lys His Gln Leu Ser Leu Thr Phe Ala Val Thr Gln
        35                  40                  45

Lys Thr Gln Arg Arg Trp Phe Leu Asp Lys Leu Val Asp Glu Ile Gly
    50                  55                  60

Val Gly Tyr Val Ala Asp Lys Gly Ser Val Ser Asn Tyr Ile Leu Ser
65                  70                  75                  80

Glu Ile Lys Pro Leu His Asn Phe Leu Thr Gln Leu Gln Pro Phe Leu
                85                  90                  95

Lys Leu Lys Gln Lys Gln Ala Asn Leu Val Leu Lys Ile Ile Glu Gln
            100                 105                 110

Leu Pro Ser Ala Lys Glu Ser Pro Asp Lys Phe Leu Glu Val Cys Thr
        115                 120                 125

Trp Val Asp Gln Ile Ala Ala Leu Asn Asp Ser Lys Thr Arg Lys Thr
    130                 135                 140

Thr Ser Glu Thr Val Arg Ala Val Leu Asp Ser Leu Ser Glu Lys Lys
145                 150                 155                 160

Lys Ser Ser Pro Ala Ala Asp
                165

<210> SEQ ID NO 123
<211> LENGTH: 167
<212> TYPE: PRT
<213> ORGANISM: Artificial Sequence
<220> FEATURE:
<223> OTHER INFORMATION: Description of Artificial Sequence: I-CreI
      variant

<400> SEQUENCE: 123

Met Ala Asn Thr Lys Tyr Asn Lys Glu Phe Leu Leu Tyr Leu Ala Gly
1               5                   10                  15

Phe Val Asp Gly Asp Gly Ser Ile Ile Ala Gln Ile Lys Pro Asn Gln
            20                  25                  30

Ser Arg Lys Phe Lys His Gln Leu Gln Leu Thr Phe Ala Val Thr Gln
        35                  40                  45

Lys Thr Gln Arg Arg Trp Phe Leu Asp Lys Leu Val Asp Glu Ile Gly
    50                  55                  60

Val Gly Tyr Val Arg Asp Ser Gly Ser Val Ser Asn Tyr Ile Leu Ser
65                  70                  75                  80

Glu Ile Lys Pro Leu His Asn Phe Leu Thr Gln Leu Gln Pro Phe Leu
                85                  90                  95

Lys Leu Lys Gln Lys Gln Ala Asn Leu Val Leu Lys Ile Ile Glu Gln
            100                 105                 110

Leu Pro Ser Ala Lys Glu Ser Pro Asp Lys Phe Leu Glu Val Cys Thr
        115                 120                 125

Trp Val Asp Gln Ile Ala Ala Leu Asn Asp Ser Lys Thr Arg Lys Thr
    130                 135                 140

Thr Ser Glu Thr Val Arg Ala Val Leu Asp Ser Leu Ser Glu Lys Lys
145                 150                 155                 160

Lys Ser Ser Pro Ala Ala Asp
                165
```

<210> SEQ ID NO 124
<211> LENGTH: 167
<212> TYPE: PRT
<213> ORGANISM: Artificial Sequence
<220> FEATURE:
<223> OTHER INFORMATION: Description of Artificial Sequence: I-CreI variant

<400> SEQUENCE: 124

Met Ala Asn Thr Lys Tyr Asn Lys Glu Phe Leu Leu Tyr Leu Ala Gly
1               5                   10                  15

Phe Val Asp Gly Asp Gly Ser Ile Ile Ala Gln Ile Lys Pro Arg Gln
            20                  25                  30

Asp Tyr Lys Phe Lys His Gln Leu Ser Leu Thr Phe Thr Val Thr Gln
        35                  40                  45

Lys Thr Gln Arg Arg Trp Phe Leu Asp Lys Leu Val Asp Glu Ile Gly
    50                  55                  60

Val Gly Tyr Val Asn Asp Asn Gly Ser Val Ser Asn Tyr Ile Leu Ser
65                  70                  75                  80

Glu Ile Lys Pro Leu His Asn Phe Leu Thr Gln Leu Gln Pro Phe Leu
                85                  90                  95

Lys Leu Lys Gln Lys Gln Ala Asn Leu Val Leu Lys Ile Ile Glu Gln
            100                 105                 110

Leu Pro Ser Ala Lys Glu Ser Pro Asp Lys Phe Leu Glu Val Cys Thr
        115                 120                 125

Trp Val Asp Gln Ile Ala Ala Leu Asn Asp Ser Lys Thr Arg Lys Thr
    130                 135                 140

Thr Ser Glu Thr Val Arg Ala Val Leu Asp Ser Leu Ser Glu Lys Lys
145                 150                 155                 160

Lys Ser Ser Pro Ala Ala Asp
                165

<210> SEQ ID NO 125
<211> LENGTH: 167
<212> TYPE: PRT
<213> ORGANISM: Artificial Sequence
<220> FEATURE:
<223> OTHER INFORMATION: Description of Artificial Sequence: I-CreI variant

<400> SEQUENCE: 125

Met Ala Asn Thr Lys Tyr Asn Lys Glu Phe Leu Leu Tyr Leu Ala Gly
1               5                   10                  15

Phe Val Asp Gly Asp Gly Ser Ile Ile Ala Gln Ile Lys Pro Asn Gln
            20                  25                  30

Ser Ser Lys Phe Lys His Arg Leu His Leu Thr Phe Gln Val Thr Gln
        35                  40                  45

Lys Thr Gln Arg Arg Trp Phe Leu Asp Lys Leu Val Asp Glu Ile Gly
    50                  55                  60

Val Gly Tyr Val His Asp His Gly Ser Val Ser Asn Tyr Ile Leu Ser
65                  70                  75                  80

Glu Ile Lys Pro Leu His Asn Phe Leu Thr Gln Leu Gln Pro Phe Leu
                85                  90                  95

Lys Leu Lys Gln Lys Gln Ala Asn Leu Val Leu Lys Ile Ile Glu Gln
            100                 105                 110

Leu Pro Ser Ala Lys Glu Ser Pro Asp Lys Phe Leu Glu Val Cys Thr
        115                 120                 125

Trp Val Asp Gln Ile Ala Ala Leu Asn Asp Ser Lys Thr Arg Lys Thr

```
                130                 135                 140
Thr Ser Glu Thr Val Arg Ala Val Leu Asp Ser Leu Ser Glu Lys Lys
145                 150                 155                 160

Lys Ser Ser Pro Ala Ala Asp
                165

<210> SEQ ID NO 126
<211> LENGTH: 167
<212> TYPE: PRT
<213> ORGANISM: Artificial Sequence
<220> FEATURE:
<223> OTHER INFORMATION: Description of Artificial Sequence: I-CreI
      variant

<400> SEQUENCE: 126

Met Ala Asn Thr Lys Tyr Asn Lys Glu Phe Leu Leu Tyr Leu Ala Gly
1               5                   10                  15

Phe Val Asp Gly Asp Gly Ser Ile Ile Ala Gln Ile Arg Pro Asn Gln
            20                  25                  30

Ser Ala Lys Phe Lys His Tyr Leu Gln Leu Thr Phe Thr Val Thr Gln
        35                  40                  45

Lys Thr Gln Arg Arg Trp Phe Leu Asp Lys Leu Val Asp Glu Ile Gly
    50                  55                  60

Val Gly Tyr Val His Asp His Gly Ser Val Ser Asn Tyr Ile Leu Ser
65                  70                  75                  80

Glu Ile Lys Pro Leu His Asn Phe Leu Thr Gln Leu Gln Pro Phe Leu
                85                  90                  95

Lys Leu Lys Gln Lys Gln Ala Asn Leu Val Leu Lys Ile Ile Glu Gln
            100                 105                 110

Leu Pro Ser Ala Lys Glu Ser Pro Asp Lys Phe Leu Glu Val Cys Thr
        115                 120                 125

Trp Val Asp Gln Ile Ala Ala Leu Asn Asp Ser Lys Thr Arg Lys Thr
    130                 135                 140

Thr Ser Glu Thr Val Arg Ala Val Leu Asp Ser Leu Ser Glu Lys Lys
145                 150                 155                 160

Lys Ser Ser Pro Ala Ala Asp
                165

<210> SEQ ID NO 127
<211> LENGTH: 167
<212> TYPE: PRT
<213> ORGANISM: Artificial Sequence
<220> FEATURE:
<223> OTHER INFORMATION: Description of Artificial Sequence: I-CreI
      variant

<400> SEQUENCE: 127

Met Ala Asn Thr Lys Tyr Asn Lys Glu Phe Leu Leu Tyr Leu Ala Gly
1               5                   10                  15

Phe Val Asp Gly Asp Gly Ser Ile Ile Ala Gln Ile Lys Pro Arg Gln
            20                  25                  30

Asp Tyr Lys Phe Lys His Gln Leu Ser Leu Thr Phe Lys Val Thr Gln
        35                  40                  45

Lys Thr Gln Arg Arg Trp Phe Leu Asp Lys Leu Val Asp Glu Ile Gly
    50                  55                  60

Val Gly Tyr Val Tyr Asp Ser Gly Ser Val Ser Gln Tyr Asn Leu Ser
65                  70                  75                  80

Glu Ile Lys Pro Leu His Asn Phe Leu Thr Gln Leu Gln Pro Phe Leu
                85                  90                  95
```

-continued

```
Lys Leu Lys Gln Lys Gln Ala Asn Leu Val Leu Lys Ile Ile Glu Gln
                100                 105                 110

Leu Pro Ser Ala Lys Glu Ser Pro Asp Lys Phe Leu Glu Val Cys Thr
            115                 120                 125

Trp Val Asp Gln Ile Ala Ala Leu Asn Asp Ser Lys Thr Arg Lys Thr
    130                 135                 140

Thr Ser Glu Thr Val Arg Ala Val Leu Asp Ser Leu Ser Glu Lys Lys
145                 150                 155                 160

Lys Ser Ser Pro Ala Ala Asp
                165

<210> SEQ ID NO 128
<211> LENGTH: 167
<212> TYPE: PRT
<213> ORGANISM: Artificial Sequence
<220> FEATURE:
<223> OTHER INFORMATION: Description of Artificial Sequence: I-CreI
      variant

<400> SEQUENCE: 128

Met Ala Asn Thr Lys Tyr Asn Lys Glu Phe Leu Leu Tyr Leu Ala Gly
1               5                   10                  15

Phe Val Asp Gly Asp Gly Ser Ile Ile Ala Gln Ile Lys Pro His Gln
            20                  25                  30

Ser Ser Lys Phe Lys His Gln Leu Ser Leu Thr Phe Gln Val Thr Gln
        35                  40                  45

Lys Thr Gln Arg Arg Trp Phe Leu Asp Lys Leu Val Asp Glu Ile Gly
    50                  55                  60

Val Gly Tyr Val Arg Asp Ser Gly Ser Val Ser Asp Tyr Lys Leu Ser
65                  70                  75                  80

Glu Ile Lys Pro Leu His Asn Phe Leu Thr Gln Leu Gln Pro Phe Leu
                85                  90                  95

Lys Leu Lys Gln Lys Gln Ala Asn Leu Val Leu Lys Ile Ile Glu Gln
                100                 105                 110

Leu Pro Ser Ala Lys Glu Ser Pro Asp Lys Phe Leu Glu Val Cys Thr
            115                 120                 125

Trp Val Asp Gln Ile Ala Ala Leu Asn Asp Ser Lys Thr Arg Lys Thr
    130                 135                 140

Thr Ser Glu Thr Val Arg Ala Val Leu Asp Ser Leu Ser Glu Lys Lys
145                 150                 155                 160

Lys Ser Ser Pro Ala Ala Asp
                165

<210> SEQ ID NO 129
<211> LENGTH: 167
<212> TYPE: PRT
<213> ORGANISM: Artificial Sequence
<220> FEATURE:
<223> OTHER INFORMATION: Description of Artificial Sequence: I-CreI
      variant

<400> SEQUENCE: 129

Met Ala Asn Thr Lys Tyr Asn Lys Glu Phe Leu Leu Tyr Leu Ala Gly
1               5                   10                  15

Phe Val Asp Gly Asp Gly Ser Ile Ile Ala Gln Ile Arg Pro Asn Gln
            20                  25                  30

Ser Ala Lys Phe Lys His Tyr Leu Gln Leu Thr Phe Gln Val Thr Gln
        35                  40                  45
```

Lys Thr Gln Arg Arg Trp Phe Leu Asp Lys Leu Val Asp Glu Ile Gly
            50                  55                  60

Val Gly Tyr Val Arg Asp Ser Gly Ser Val Ser Asp Tyr Lys Leu Ser
 65                  70                  75                  80

Glu Ile Lys Pro Leu His Asn Phe Leu Thr Gln Leu Gln Pro Phe Leu
                 85                  90                  95

Lys Leu Lys Gln Lys Gln Ala Asn Leu Val Leu Lys Ile Ile Glu Gln
                100                 105                 110

Leu Pro Ser Ala Lys Glu Ser Pro Asp Lys Phe Leu Glu Val Cys Thr
            115                 120                 125

Trp Val Asp Gln Ile Ala Ala Leu Asn Asp Ser Lys Thr Arg Lys Thr
130                 135                 140

Thr Ser Glu Thr Val Arg Ala Val Leu Asp Ser Leu Ser Glu Lys Lys
145                 150                 155                 160

Lys Ser Ser Pro Ala Ala Asp
                165

<210> SEQ ID NO 130
<211> LENGTH: 167
<212> TYPE: PRT
<213> ORGANISM: Artificial Sequence
<220> FEATURE:
<223> OTHER INFORMATION: Description of Artificial Sequence: I-CreI
      variant

<400> SEQUENCE: 130

Met Ala Asn Thr Lys Tyr Asn Lys Glu Phe Leu Leu Tyr Leu Ala Gly
1               5                   10                  15

Phe Val Asp Gly Asp Gly Ser Ile Ile Ala Gln Ile Lys Pro Asn Gln
            20                  25                  30

Asp Tyr Lys Phe Lys His Cys Leu Ser Leu Thr Phe Gln Val Thr Gln
        35                  40                  45

Lys Thr Gln Arg Arg Trp Phe Leu Asp Lys Leu Val Asp Glu Ile Gly
    50                  55                  60

Val Gly Tyr Val Arg Asp Ser Gly Ser Val Ser Asp Tyr Lys Leu Ser
 65                  70                  75                  80

Glu Ile Lys Pro Leu His Asn Phe Leu Thr Gln Leu Gln Pro Phe Leu
                 85                  90                  95

Lys Leu Lys Gln Lys Gln Ala Asn Leu Val Leu Lys Ile Ile Glu Gln
                100                 105                 110

Leu Pro Ser Ala Lys Glu Ser Pro Asp Lys Phe Leu Glu Val Cys Thr
            115                 120                 125

Trp Val Asp Gln Ile Ala Ala Leu Asn Asp Ser Lys Thr Arg Lys Thr
130                 135                 140

Thr Ser Glu Thr Val Arg Ala Val Leu Asp Ser Leu Ser Glu Lys Lys
145                 150                 155                 160

Lys Ser Ser Pro Ala Ala Asp
                165

<210> SEQ ID NO 131
<211> LENGTH: 167
<212> TYPE: PRT
<213> ORGANISM: Artificial Sequence
<220> FEATURE:
<223> OTHER INFORMATION: Description of Artificial Sequence: I-CreI
      variant

<400> SEQUENCE: 131

Met Ala Asn Thr Lys Tyr Asn Lys Glu Phe Leu Leu Tyr Leu Ala Gly

```
                1               5                  10                 15
        Phe Val Asp Gly Asp Gly Ser Ile Ile Ala Gln Ile Lys Pro Asn Gln
                        20                  25                 30

Ser Tyr Lys Phe Lys His Gln Leu Ser Leu Thr Phe Val Thr Gln
                    35                  40                 45

Lys Thr Gln Arg Arg Trp Phe Leu Asp Lys Leu Val Asp Glu Ile Gly
                50                  55                  60

Val Gly Tyr Val Arg Asp Ala Gly Ser Val Ser Asn Tyr Ile Leu Ser
        65                  70                  75                  80

Glu Ile Lys Pro Leu His Asn Phe Leu Thr Gln Leu Gln Pro Phe Leu
                        85                  90                 95

Lys Leu Lys Gln Lys Gln Ala Asn Leu Val Leu Lys Ile Ile Glu Gln
                    100                 105                 110

Leu Pro Ser Ala Lys Glu Ser Pro Asp Lys Phe Leu Glu Val Cys Thr
                    115                 120                 125

Trp Val Asp Gln Ile Ala Ala Leu Asn Asp Ser Lys Thr Arg Lys Thr
                    130                 135                 140

Thr Ser Glu Thr Val Arg Ala Val Leu Asp Ser Leu Ser Glu Lys Lys
        145                 150                 155                 160

Lys Ser Ser Pro Ala Ala Asp
                        165

<210> SEQ ID NO 132
<211> LENGTH: 167
<212> TYPE: PRT
<213> ORGANISM: Artificial Sequence
<220> FEATURE:
<223> OTHER INFORMATION: Description of Artificial Sequence: I-CreI
      variant

<400> SEQUENCE: 132

Met Ala Asn Thr Lys Tyr Asn Lys Glu Phe Leu Leu Tyr Leu Ala Gly
        1               5                  10                 15

Phe Val Asp Gly Asp Gly Ser Ile Ile Ala Gln Ile Glu Pro Asn Gln
                        20                  25                 30

Ser Arg Lys Phe Lys His Arg Leu Arg Leu Thr Phe Gln Val Thr Gln
                    35                  40                 45

Lys Thr Gln Arg Arg Trp Phe Leu Asp Lys Leu Val Asp Glu Ile Gly
                50                  55                  60

Val Gly Tyr Val Arg Asp Arg Gly Ser Val Ser Asn Tyr Ile Leu Ser
        65                  70                  75                  80

Glu Ile Lys Pro Leu His Asn Phe Leu Thr Gln Leu Gln Pro Phe Leu
                        85                  90                 95

Lys Leu Lys Gln Lys Gln Ala Asn Leu Val Leu Lys Ile Ile Glu Gln
                    100                 105                 110

Leu Pro Ser Ala Lys Glu Ser Pro Asp Lys Phe Leu Glu Val Cys Thr
                    115                 120                 125

Trp Val Asp Gln Ile Ala Ala Leu Asn Asp Ser Lys Thr Arg Lys Thr
                    130                 135                 140

Thr Ser Glu Thr Val Arg Ala Val Leu Asp Ser Leu Ser Glu Lys Lys
        145                 150                 155                 160

Lys Ser Ser Pro Ala Ala Asp
                        165

<210> SEQ ID NO 133
<211> LENGTH: 163
<212> TYPE: PRT
```

<213> ORGANISM: Chlamydomonas reinhardtii

<400> SEQUENCE: 133

Met Asn Thr Lys Tyr Asn Lys Glu Phe Leu Leu Tyr Leu Ala Gly Phe
1               5                   10                  15

Val Asp Gly Asp Gly Ser Ile Ile Ala Gln Ile Lys Pro Asn Gln Ser
            20                  25                  30

Tyr Lys Phe Lys His Gln Leu Ser Leu Thr Phe Gln Val Thr Gln Lys
        35                  40                  45

Thr Gln Arg Arg Trp Phe Leu Asp Lys Leu Val Asp Glu Ile Gly Val
    50                  55                  60

Gly Tyr Val Arg Asp Arg Gly Ser Val Ser Asp Tyr Ile Leu Ser Glu
65                  70                  75                  80

Ile Lys Pro Leu His Asn Phe Leu Thr Gln Leu Gln Pro Phe Leu Lys
                85                  90                  95

Leu Lys Gln Lys Gln Ala Asn Leu Val Leu Lys Ile Ile Glu Gln Leu
            100                 105                 110

Pro Ser Ala Lys Glu Ser Pro Asp Lys Phe Leu Glu Val Cys Thr Trp
        115                 120                 125

Val Asp Gln Ile Ala Ala Leu Asn Asp Ser Lys Thr Arg Lys Thr Thr
    130                 135                 140

Ser Glu Thr Val Arg Ala Val Leu Asp Ser Leu Ser Glu Lys Lys Lys
145                 150                 155                 160

Ser Ser Pro

<210> SEQ ID NO 134
<211> LENGTH: 5
<212> TYPE: PRT
<213> ORGANISM: Artificial Sequence
<220> FEATURE:
<223> OTHER INFORMATION: Description of Artificial Sequence: NLS peptide

<400> SEQUENCE: 134

Lys Lys Lys Arg Lys
1               5

<210> SEQ ID NO 135
<211> LENGTH: 9
<212> TYPE: PRT
<213> ORGANISM: Artificial Sequence
<220> FEATURE:
<223> OTHER INFORMATION: Description of Artificial Sequence: HA-tag
      peptide

<400> SEQUENCE: 135

Tyr Pro Tyr Asp Val Pro Asp Tyr Ala
1               5

<210> SEQ ID NO 136
<211> LENGTH: 15
<212> TYPE: PRT
<213> ORGANISM: Artificial Sequence
<220> FEATURE:
<223> OTHER INFORMATION: Description of Artificial Sequence: S-tag
      peptide

<400> SEQUENCE: 136

Lys Glu Thr Ala Ala Ala Lys Phe Glu Arg Gln His Met Asp Ser
1               5                   10                  15

<210> SEQ ID NO 137
<211> LENGTH: 25

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 137
tagtatacag aaactgttgc atcgc                                           25

<210> SEQ ID NO 138
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 138
cgtctgctgc tccatacaag                                                 20

<210> SEQ ID NO 139
<211> LENGTH: 585
<212> TYPE: DNA
<213> ORGANISM: Artificial Sequence
<220> FEATURE:
<223> OTHER INFORMATION: Description of Artificial Sequence: IRES
      polynucleotide

<400> SEQUENCE: 139
gcccctctcc ctcccccccc cctaacgtta ctggccgaag ccgcttggaa taaggccggt      60
gtgcgtttgt ctatatgtta ttttccacca tattgccgtc ttttggcaat gtgagggccc    120
ggaaacctgg ccctgtcttc ttgacgagca ttcctagggg tctttcccct ctcgccaaag    180
gaatgcaagg tctgttgaat gtcgtgaagg aagcagttcc tctggaagct tcttgaagac    240
aaacaacgtc tgtagcgacc ctttgcaggc agcggaaccc cccacctggc gacaggtgcc    300
tctgcggcca aaagccacgt gtataagata cacctgcaaa ggcggcacaa ccccagtgcc    360
acgttgtgag ttggatagtt gtggaaagag tcaaatggct ctcctcaagc gtattcaaca    420
aggggctgaa ggatgcccag aaggtacccc attgtatggg atctgatctg gggcctcggt    480
gcacatgctt tacatgtgtt tagtcgaggt taaaaaaacg tctaggcccc ccgaaccacg    540
gggacgtggt tttcctttga aaaacacgat gataatatgg ccaca                    585

<210> SEQ ID NO 140
<400> SEQUENCE: 140

000

<210> SEQ ID NO 141
<211> LENGTH: 172
<212> TYPE: PRT
<213> ORGANISM: Artificial Sequence
<220> FEATURE:
<223> OTHER INFORMATION: Description of Artificial Sequence: MO_1 NLS
      polypeptide

<400> SEQUENCE: 141

Met Lys Lys Lys Arg Lys Ala Asn Thr Lys Tyr Asn Lys Glu Phe Leu
1               5                   10                  15

Leu Tyr Leu Ala Gly Phe Val Asp Gly Asp Gly Ser Ile Ile Ala Gln
            20                  25                  30

Ile Glu Pro Asn Gln Ser Arg Lys Phe Lys His Arg Leu Arg Leu Thr
        35                  40                  45
```

-continued

Phe Ala Val Thr Gln Lys Thr Gln Arg Arg Trp Phe Leu Asp Lys Leu
              50                  55                  60

Val Asp Glu Ile Gly Val Gly Tyr Val His Asp Gln Gly Ser Val Ser
 65                  70                  75                  80

Asn Tyr Ile Leu Ser Glu Ile Lys Pro Leu His Asn Phe Leu Thr Gln
                 85                  90                  95

Leu Gln Pro Phe Leu Lys Leu Lys Gln Lys Gln Ala Asn Leu Ala Leu
                100                 105                 110

Arg Ile Ile Glu Gln Leu Pro Ser Ala Lys Glu Ser Pro Asp Lys Phe
            115                 120                 125

Leu Glu Val Cys Thr Trp Val Asp Gln Ile Ala Ala Leu Asn Asp Ser
130                 135                 140

Lys Thr Arg Lys Thr Thr Ser Glu Thr Val Arg Ala Val Leu Asp Ser
145                 150                 155                 160

Leu Ser Glu Lys Lys Lys Ser Ser Pro Ala Ala Asp
                165                 170

<210> SEQ ID NO 142
<211> LENGTH: 175
<212> TYPE: PRT
<213> ORGANISM: Artificial Sequence
<220> FEATURE:
<223> OTHER INFORMATION: Description of Artificial Sequence: mO_2 TagHA
      polypeptide

<400> SEQUENCE: 142

Met Tyr Pro Tyr Asp Val Pro Asp Tyr Ala Asn Thr Lys Tyr Asn Lys
 1               5                  10                  15

Glu Phe Leu Leu Tyr Leu Ala Gly Phe Val Asp Ser Asp Gly Ser Ile
             20                  25                  30

Val Ala Gln Ile Lys Pro Asn Gln Ser Tyr Lys Phe Lys His Gln Leu
         35                  40                  45

Ser Leu Thr Phe Tyr Val Thr Gln Lys Thr Gln Arg Arg Trp Phe Leu
 50                  55                  60

Asp Lys Leu Val Asp Glu Ile Gly Val Gly Tyr Val Arg Asp Ser Gly
 65                  70                  75                  80

Ser Val Ser Gln Tyr Ile Leu Ser Glu Ile Lys Pro Leu His Asn Phe
                 85                  90                  95

Leu Thr Gln Leu Gln Pro Phe Leu Lys Leu Lys Gln Lys Gln Ala Asn
                100                 105                 110

Leu Val Leu Lys Ile Ile Glu Gln Leu Pro Ser Ala Lys Glu Ser Pro
            115                 120                 125

Asp Lys Phe Leu Glu Val Cys Thr Trp Val Asp Gln Ile Ala Ala Leu
130                 135                 140

Asn Asp Ser Lys Thr Arg Lys Thr Thr Ser Glu Thr Val Arg Ala Val
145                 150                 155                 160

Leu Asp Ser Leu Ser Glu Lys Lys Lys Ser Ser Pro Ala Ala Asp
                165                 170                 175

<210> SEQ ID NO 143
<211> LENGTH: 182
<212> TYPE: PRT
<213> ORGANISM: Artificial Sequence
<220> FEATURE:
<223> OTHER INFORMATION: Description of Artificial Sequence: MO_1 Stag
      polypeptide

<400> SEQUENCE: 143

```
Met Lys Glu Thr Ala Ala Ala Lys Phe Glu Arg Gln His Met Asp Ser
1               5                   10                  15

Ala Asn Thr Lys Tyr Asn Lys Glu Phe Leu Leu Tyr Leu Ala Gly Phe
            20                  25                  30

Val Asp Gly Asp Gly Ser Ile Ile Ala Gln Ile Glu Pro Asn Gln Ser
            35                  40                  45

Arg Lys Phe Lys His Arg Leu Arg Leu Thr Phe Ala Val Thr Gln Lys
50                  55                  60

Thr Gln Arg Arg Trp Phe Leu Asp Lys Leu Val Asp Glu Ile Gly Val
65                  70                  75                  80

Gly Tyr Val His Asp Gln Gly Ser Val Ser Asn Tyr Ile Leu Ser Glu
                85                  90                  95

Ile Lys Pro Leu His Asn Phe Leu Thr Gln Leu Gln Pro Phe Leu Lys
            100                 105                 110

Leu Lys Gln Lys Gln Ala Asn Leu Ala Leu Arg Ile Ile Glu Gln Leu
            115                 120                 125

Pro Ser Ala Lys Glu Ser Pro Asp Lys Phe Leu Glu Val Cys Thr Trp
130                 135                 140

Val Asp Gln Ile Ala Ala Leu Asn Asp Ser Lys Thr Arg Lys Thr Thr
145                 150                 155                 160

Ser Glu Thr Val Arg Ala Val Leu Asp Ser Leu Ser Glu Lys Lys Lys
                165                 170                 175

Ser Ser Pro Ala Ala Asp
            180

<210> SEQ ID NO 144
<211> LENGTH: 181
<212> TYPE: PRT
<213> ORGANISM: Artificial Sequence
<220> FEATURE:
<223> OTHER INFORMATION: Description of Artificial Sequence:
      MO_2NLS+TagHA polypeptide

<400> SEQUENCE: 144

Met Tyr Pro Tyr Asp Val Pro Asp Tyr Ala Lys Lys Arg Lys Ala
1               5                   10                  15

Asn Thr Lys Tyr Asn Lys Glu Phe Leu Leu Tyr Leu Ala Gly Phe Val
            20                  25                  30

Asp Ser Asp Gly Ser Ile Val Ala Gln Ile Lys Pro Asn Gln Ser Tyr
            35                  40                  45

Lys Phe Lys His Gln Leu Ser Leu Thr Phe Tyr Val Thr Gln Lys Thr
50                  55                  60

Gln Arg Arg Trp Phe Leu Asp Lys Leu Val Asp Glu Ile Gly Val Gly
65                  70                  75                  80

Tyr Val Arg Asp Ser Gly Ser Val Ser Gln Tyr Ile Leu Ser Glu Ile
                85                  90                  95

Lys Pro Leu His Asn Phe Leu Thr Gln Leu Gln Pro Phe Leu Lys Leu
            100                 105                 110

Lys Gln Lys Gln Ala Asn Leu Val Leu Lys Ile Ile Glu Gln Leu Pro
            115                 120                 125

Ser Ala Lys Glu Ser Pro Asp Lys Phe Leu Glu Val Cys Thr Trp Val
130                 135                 140

Asp Gln Ile Ala Ala Leu Asn Asp Ser Lys Thr Arg Lys Thr Thr Ser
145                 150                 155                 160

Glu Thr Val Arg Ala Val Leu Asp Ser Leu Ser Glu Lys Lys Lys Ser
                165                 170                 175
```

Ser Pro Ala Ala Asp
            180

<210> SEQ ID NO 145
<211> LENGTH: 187
<212> TYPE: PRT
<213> ORGANISM: Artificial Sequence
<220> FEATURE:
<223> OTHER INFORMATION: Description of Artificial Sequence:
      MO_1NLS+STag polypeptide

<400> SEQUENCE: 145

Met Lys Glu Thr Ala Ala Ala Lys Phe Glu Arg Gln His Met Asp Ser
1               5                   10                  15

Lys Lys Lys Arg Lys Ala Asn Thr Lys Tyr Asn Lys Glu Phe Leu Leu
            20                  25                  30

Tyr Leu Ala Gly Phe Val Asp Gly Asp Gly Ser Ile Ile Ala Gln Ile
        35                  40                  45

Glu Pro Asn Gln Ser Arg Lys Phe Lys His Arg Leu Arg Leu Thr Phe
    50                  55                  60

Ala Val Thr Gln Lys Thr Gln Arg Arg Trp Phe Leu Asp Lys Leu Val
65                  70                  75                  80

Asp Glu Ile Gly Val Gly Tyr Val His Asp Gln Gly Ser Val Ser Asn
                85                  90                  95

Tyr Ile Leu Ser Glu Ile Lys Pro Leu His Asn Phe Leu Thr Gln Leu
            100                 105                 110

Gln Pro Phe Leu Lys Leu Lys Gln Lys Gln Ala Asn Leu Ala Leu Arg
        115                 120                 125

Ile Ile Glu Gln Leu Pro Ser Ala Lys Glu Ser Pro Asp Lys Phe Leu
    130                 135                 140

Glu Val Cys Thr Trp Val Asp Gln Ile Ala Ala Leu Asn Asp Ser Lys
145                 150                 155                 160

Thr Arg Lys Thr Thr Ser Glu Thr Val Arg Ala Val Leu Asp Ser Leu
                165                 170                 175

Ser Glu Lys Lys Lys Ser Ser Pro Ala Ala Asp
            180                 185

<210> SEQ ID NO 146
<211> LENGTH: 354
<212> TYPE: PRT
<213> ORGANISM: Artificial Sequence
<220> FEATURE:
<223> OTHER INFORMATION: Description of Artificial Sequence:
      Single-chain MO_1/mO_2 polypeptide

<400> SEQUENCE: 146

Met Ala Asn Thr Lys Tyr Asn Lys Glu Phe Leu Leu Tyr Leu Ala Gly
1               5                   10                  15

Phe Val Asp Gly Asp Gly Ser Ile Ile Ala Gln Ile Glu Pro Asn Gln
            20                  25                  30

Ser Arg Lys Phe Lys His Arg Leu Arg Leu Thr Phe Ala Val Thr Gln
        35                  40                  45

Lys Thr Gln Arg Arg Trp Phe Leu Asp Lys Leu Val Asp Glu Ile Gly
    50                  55                  60

Val Gly Tyr Val His Asp Gln Gly Ser Val Ser Asn Tyr Ile Leu Ser
65                  70                  75                  80

Glu Ile Lys Pro Leu His Asn Phe Leu Thr Gln Leu Gln Pro Phe Leu
                85                  90                  95

Lys Leu Lys Gln Lys Gln Ala Asn Leu Ala Leu Arg Ile Ile Glu Gln

```
                    100                 105                 110
Leu Pro Ser Ala Lys Glu Ser Pro Asp Lys Phe Leu Glu Val Cys Thr
        115                 120                 125

Trp Val Asp Gln Ile Ala Ala Leu Asn Asp Ser Lys Thr Arg Lys Thr
130                 135                 140

Thr Ser Glu Thr Val Arg Ala Val Leu Asp Ser Leu Ser Glu Lys Lys
145                 150                 155                 160

Lys Ser Ser Pro Ala Ala Gly Gly Ser Asp Lys Tyr Asn Gln Ala Leu
                165                 170                 175

Ser Lys Tyr Asn Gln Ala Leu Ser Lys Tyr Asn Gln Ala Leu Ser Gly
                180                 185                 190

Gly Gly Gly Ser Asn Lys Glu Phe Leu Leu Tyr Leu Ala Gly Phe Val
                195                 200                 205

Asp Ser Asp Gly Ser Ile Val Ala Gln Ile Lys Pro Asn Gln Ser Tyr
                210                 215                 220

Lys Phe Lys His Gln Leu Ser Leu Thr Phe Tyr Val Thr Gln Lys Thr
225                 230                 235                 240

Gln Arg Arg Trp Phe Leu Asp Lys Leu Val Asp Glu Ile Gly Val Gly
                245                 250                 255

Tyr Val Arg Asp Ser Gly Ser Val Ser Gln Tyr Ile Leu Ser Glu Ile
                260                 265                 270

Lys Pro Leu His Asn Phe Leu Thr Gln Leu Gln Pro Phe Leu Lys Leu
                275                 280                 285

Lys Gln Lys Gln Ala Asn Leu Val Leu Lys Ile Ile Glu Gln Leu Pro
                290                 295                 300

Ser Ala Lys Glu Ser Pro Asp Lys Phe Leu Glu Val Cys Thr Trp Val
305                 310                 315                 320

Asp Gln Ile Ala Ala Leu Asn Asp Ser Lys Thr Arg Lys Thr Thr Ser
                325                 330                 335

Glu Thr Val Arg Ala Val Leu Asp Ser Leu Ser Glu Lys Lys Lys Ser
                340                 345                 350

Ser Pro

<210> SEQ ID NO 147
<211> LENGTH: 167
<212> TYPE: PRT
<213> ORGANISM: Artificial Sequence
<220> FEATURE:
<223> OTHER INFORMATION: Description of Artificial Sequence: MO_2
      E8K+E61R polypeptide

<400> SEQUENCE: 147

Met Ala Asn Thr Lys Tyr Asn Lys Lys Phe Leu Leu Tyr Leu Ala Gly
1               5                   10                  15

Phe Val Asp Ser Asp Gly Ser Ile Val Ala Gln Ile Lys Pro Asn Gln
                20                  25                  30

Ser Tyr Lys Phe Lys His Gln Leu Ser Leu Thr Phe Tyr Val Thr Gln
            35                  40                  45

Lys Thr Gln Arg Arg Trp Phe Leu Asp Lys Leu Val Asp Arg Ile Gly
50                  55                  60

Val Gly Tyr Val Arg Asp Ser Gly Ser Val Ser Gln Tyr Ile Leu Ser
65                  70                  75                  80

Glu Ile Lys Pro Leu His Asn Phe Leu Thr Gln Leu Gln Pro Phe Leu
                85                  90                  95

Lys Leu Lys Gln Lys Gln Ala Asn Leu Val Leu Lys Ile Ile Glu Gln
                100                 105                 110
```

```
Leu Pro Ser Ala Lys Glu Ser Pro Asp Lys Phe Leu Glu Val Cys Thr
        115                 120                 125

Trp Val Asp Gln Ile Ala Ala Leu Asn Asp Ser Lys Thr Arg Lys Thr
    130                 135                 140

Thr Ser Glu Thr Val Arg Ala Val Leu Asp Ser Leu Ser Glu Lys Lys
145                 150                 155                 160

Lys Ser Ser Pro Ala Ala Asp
                165

<210> SEQ ID NO 148
<211> LENGTH: 167
<212> TYPE: PRT
<213> ORGANISM: Artificial Sequence
<220> FEATURE:
<223> OTHER INFORMATION: Description of Artificial Sequence: MO_1
      K7E+K96E polypeptide

<400> SEQUENCE: 148

Met Ala Asn Thr Lys Tyr Asn Glu Glu Phe Leu Leu Tyr Leu Ala Gly
1               5                   10                  15

Phe Val Asp Gly Asp Gly Ser Ile Ile Ala Gln Ile Glu Pro Asn Gln
            20                  25                  30

Ser Arg Lys Phe Lys His Arg Leu Arg Leu Thr Phe Ala Val Thr Gln
        35                  40                  45

Lys Thr Gln Arg Arg Trp Phe Leu Asp Lys Leu Val Asp Glu Ile Gly
    50                  55                  60

Val Gly Tyr Val His Asp Gln Gly Ser Val Ser Asn Tyr Ile Leu Ser
65                  70                  75                  80

Glu Ile Lys Pro Leu His Asn Phe Leu Thr Gln Leu Gln Pro Phe Leu
                85                  90                  95

Glu Leu Lys Gln Lys Gln Ala Asn Leu Ala Leu Arg Ile Ile Glu Gln
            100                 105                 110

Leu Pro Ser Ala Lys Glu Ser Pro Asp Lys Phe Leu Glu Val Cys Thr
        115                 120                 125

Trp Val Asp Gln Ile Ala Ala Leu Asn Asp Ser Lys Thr Arg Lys Thr
    130                 135                 140

Thr Ser Glu Thr Val Arg Ala Val Leu Asp Ser Leu Ser Glu Lys Lys
145                 150                 155                 160

Lys Ser Ser Pro Ala Ala Asp
                165

<210> SEQ ID NO 149
<211> LENGTH: 30
<212> TYPE: PRT
<213> ORGANISM: Artificial Sequence
<220> FEATURE:
<223> OTHER INFORMATION: Description of Artificial Sequence:
      Single-chain meganuclease linker

<400> SEQUENCE: 149

Gly Gly Ser Asp Lys Tyr Asn Gln Ala Leu Ser Lys Tyr Asn Gln Ala
1               5                   10                  15

Leu Ser Lys Tyr Asn Gln Ala Leu Ser Gly Gly Gly Ser
            20                  25                  30

<210> SEQ ID NO 150
<211> LENGTH: 9
<212> TYPE: PRT
<213> ORGANISM: Artificial Sequence
<220> FEATURE:
```

-continued

```
<223> OTHER INFORMATION: Description of Artificial Sequence: I-CreI
      variant

<400> SEQUENCE: 150

Leu Ala Gly Leu Ile Asp Ala Asp Gly
1               5
```